(12) United States Patent
Stoltz et al.

(10) Patent No.: US 10,526,334 B2
(45) Date of Patent: Jan. 7, 2020

(54) METHODS FOR PREPARING BIS-TETRAHYDROISOQUINOLINE-CONTAINING COMPOUNDS

(71) Applicant: California Institute of Technology, Pasadena, CA (US)

(72) Inventors: Brian M. Stoltz, San Marino, CA (US); Eric R. Welin, Pasadena, CA (US); Scott C. Virgil, Pasadena, CA (US); Pamela Tadross, Natick, MA (US); Gerit Maria Pototschnig, San Diego, CA (US); Aurapat (Fa) Ngamnithiporn, Pasadena, CA (US); Kenji Negoro, Ibaraki (JP); Guillaume Lapointe, San Francisco, CA (US); Max Klatte, Loerrach (DE); Christopher Haley, Boston, MA (US); Christian Gruenanger, Mannheim (DE); Emil Glibstrup, Copenhagen (DK); Christopher Gilmore, Natick, MA (US); Kevin McCormack Allan, Belmont, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/038,968

(22) Filed: Jul. 18, 2018

(65) Prior Publication Data

US 2019/0048009 A1 Feb. 14, 2019

Related U.S. Application Data

(60) Provisional application No. 62/534,493, filed on Jul. 19, 2017.

(51) Int. Cl.
| | | |
|---|---|---|
| *C07D 471/18* | (2006.01) | |
| *A61P 35/00* | (2006.01) | |
| *C07D 401/04* | (2006.01) | |

(52) U.S. Cl.
CPC ............ *C07D 471/18* (2013.01); *A61P 35/00* (2018.01); *C07D 401/04* (2013.01)

(58) Field of Classification Search
CPC ............................. C09B 17/06; C07D 471/18
See application file for complete search history.

(56) References Cited

U.S. PATENT DOCUMENTS

| | | |
|---|---|---|
| 2003/0008873 A1 | 1/2003 | Myers et al. |
| 2004/0127709 A1 | 7/2004 | Danishefsky et al. |
| 2009/0076016 A1 | 3/2009 | Calvo Salve et al. |

FOREIGN PATENT DOCUMENTS

| | | |
|---|---|---|
| WO | WO-02064843 A1 | 8/2002 |
| WO | WO-200666183 A2 | 6/2006 |
| WO | WO-2019/018539 A1 | 1/2019 |

OTHER PUBLICATIONS

Dong et al., "Asymmetric total synthesis of (−)-saframycin A from L-tyrosine," The Journal of Organic Chemistry, 76(13):5363-5368 (2011).
International Search Report and Written Opinion for International Application No. PCT.US2018/042710 dated Oct. 29, 2018.
Klatte, M. et al. Progress Toward the Total Synthesis of Jorumycin. Bayer Postdoc Workshop, May 21, 2016.
Koketsu et al., "The Pictet-Spengler mechanism involved in the biosynthesis of tetrahydrisoquinoline antitumor antibiotics: a novel function for a nonribosomal peptide synthetase," Methods in Enzymology, 79-98 (2012).
Lane et al., "Asymmetric Total Syntheses of (−)-Jorumycin,(−)-Renieramycin G, 3-e pi-Jorumycin, and 3-e pi-Renieramycin G," J. Am Chem Soc, 127(36):12684-12690 (2005).
Schipper et al., "Direct arylation of arylation of azine N-oxides with aryl triflates," Tetrahedron, 65(26):4977-4983 (2009).
Shi et al., "Enantioselective Iridium-Catalyzed Hydrogenation of 3, 4-Disubstituted Isoquinolines," Angewandte Chemie International Edition, 51(33):8286-8289 (2012).

*Primary Examiner* — Rei Tsang Shiao
(74) *Attorney, Agent, or Firm* — David P. Halstead; Foley Hoag LLP

(57) ABSTRACT

(−)-Jorumycin, ecteinascidin 743, saframycin A and related compounds, methods of preparing the same, formulations comprising the compounds, and methods of treating proliferative diseases with the same are provided.

13 Claims, No Drawings

METHODS FOR PREPARING BIS-TETRAHYDROISOQUINOLINE-CONTAINING COMPOUNDS

RELATED APPLICATIONS

This application claims the benefit of U.S. Provisional Application No. 62/534,493, filed Jul. 19, 2017, the entire contents of which are incorporated herein by reference.

GOVERNMENT SUPPORT

This invention was made with government support under Grant No. GM080269 and GM127972 awarded by the National Institutes of Health and Grant No. CHE1205646 awarded by the National Science Foundation. The government has certain rights in the invention.

BACKGROUND

The bis-tetrahydroisoquinoline (bis-THIQ) family of natural products has been studied intensively in the 40 years since their initial discovery. This family of molecules is highlighted by exceptionally potent anticancer activity in addition to strong gram-positive and gram-negative antibiotic character. Jorumycin is considered the minimum pharmacophore of this natural product family, possessing a pentacyclic core, polyoxygenated termini, and carbinolamine functionality that lend these natural products their marked biological activity. To date, existing synthetic strategies toward the bis-THIQ natural products have relied heavily on electrophilic aromatic chemistry, such as the Pictet-Spengler reaction, which has limited the synthesis of non-natural analogs to highly electron-rich species that facilitate this reactivity. Accordingly, there is a need to develop new routes to access jorumycin and related analogs in the bis-THIQ family of natural products which have a full range of electrophilicity in substituents on the pentacyclic core, including electron deficient analogs.

SUMMARY

The present disclosure relates in part to the synthesis of jorumycin and structurally-related compounds, e.g., using a concise and convergent cross-coupling/enantioselective isoquinoline hydrogenation strategy, providing bis-THIQ compounds, including electron-deficient bis-THIQ variants.

Accordingly, in some embodiments, the present disclosure provides a method for preparing a compound of Formula (I):

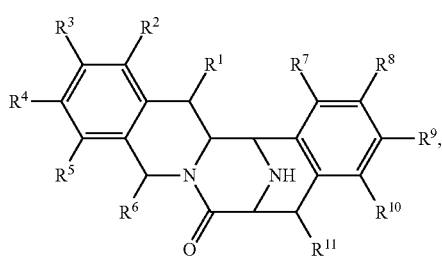

comprising contacting a compound of Formula (II):

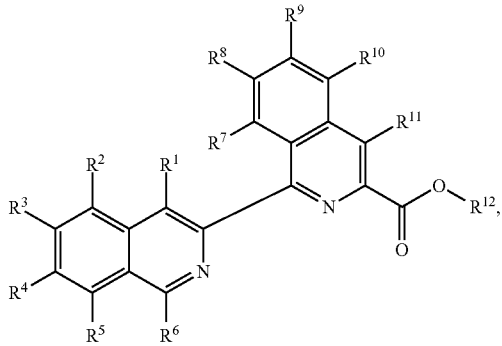

with a transition metal catalyst (preferably a chiral transition metal catalyst) under hydrogenation conditions, wherein, as valence and stability permit:

$R^1$ and $R^7$ are each independently hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, trialkylsilyloxy, or acylamino;

each instance of $R^2$, $R^3$, $R^4$, $R^5$, $R^8$, $R^9$, $R^{10}$, and $R^{11}$ is independently hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, trialkylsilyloxy, acylamino, aryl, heteroaryl, carbocyclyl, heterocyclyl aralkyl, aralkyloxy, hetaralkyl, carbocyclylalkyl, or heterocyclylalkyl;

$R^6$ is hydrogen, hydroxyl, halogen, nitro, cyano, carboxyl, sulfate, alkyl, alkenyl, alkynyl, amino, alkoxy, alkylamino, alkylthio, ether, thioether, ester, amide, thioester, carbonate, carbamate, urea, sulfonate, sulfone, sulfoxide, sulfonamide, acyl, acyloxy, trialkylsilyloxy, or acylamino; or any two of $R^1$, $R^2$, $R^3$, $R^4$, $R^5$, and $R^6$, together with the carbon atoms to which they are attached, form an aryl, heteroaryl, carbocyclyl, or heterocyclyl; or any two of $R^7$, $R^8$, $R^9$, $R^{10}$, and $R^{11}$, together with the carbon atoms to which they are attached, form an aryl, heteroaryl, carbocyclyl, or heterocyclyl; and $R^{12}$ is H, alkyl or aralkyl.

In other embodiments, the present disclosure provides a method of preparing a compound of Formula (II):

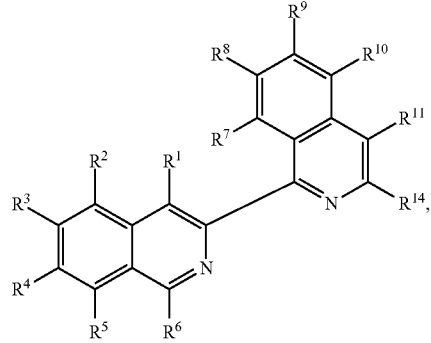

comprising combining a compound of Formula (III):

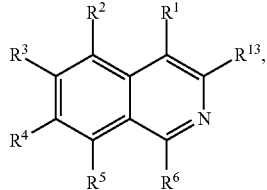
(III)

a compound of Formula (IV):

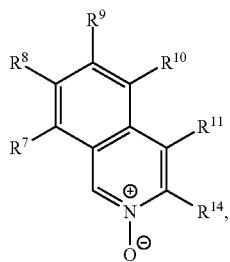
(IV)

and a transition metal catalyst under cross-coupling conditions, wherein, as valence and stability permit:

$R^1$ and $R^7$ are each independently hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, or acylamino;

each instance of $R^2$, $R^3$, $R^4$, $R^5$, $R^8$, $R^9$, $R^{10}$, and $R^{11}$ is independently hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, acylamino, aryl, heteroaryl, carbocyclyl, or heterocyclyl;

$R^6$ is hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, or acylamino; or any two of $R^1$, $R^2$, $R^3$, $R^4$, $R^5$, and $R^6$, together with the carbon atoms to which they are attached, form an aryl, heteroaryl, carbocyclyl, or heterocyclyl; or any two of $R^7$, $R^8$, $R^9$, $R^{10}$, and $R^{11}$, together with the carbon atoms to which they are attached, form an aryl, heteroaryl, carbocyclyl, or heterocyclyl; and $R^{13}$ and $R^{14}$ are each independently hydroxyl, nitro, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, or acylamino.

In other embodiments, the present disclosure provides a method of preparing a compound of Formula (VIII):

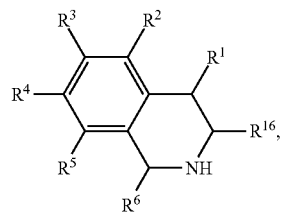
(VIII)

comprising contacting a compound of Formula (VII):

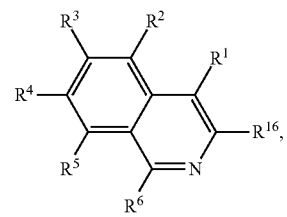
(VII)

with a transition metal catalyst under hydrogenation conditions, wherein, as valence and stability permit:

$R^6$ and $R^{16}$ are each independently hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, or acylamino;

each instance of $R^1$, $R^2$, $R^3$, $R^4$, and $R^5$ is independently hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, trialkylsilyloxy, acylamino, aryl, heteroaryl, carbocyclyl, or heterocyclyl; or any two of $R^1$, $R^2$, $R^3$, $R^4$, and $R^5$, together with the carbon atoms to which they are attached, form an aryl, heteroaryl, carbocyclyl, or heterocyclyl.

In other embodiments, the present disclosure provides a compound of Formula (V):

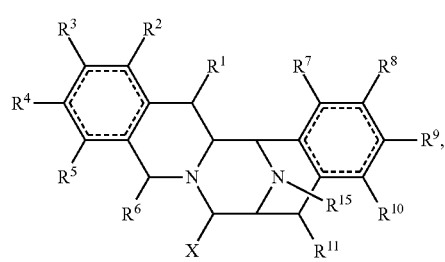
(V)

wherein:

$R^1$ and $R^7$ are each independently hydrogen, carbonyl, thiocarbonyl, imine, oxime, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, or acylamino;

each instance of $R^2$, $R^3$, $R^4$, and $R^5$ is independently hydrogen, carbonyl, thiocarbonyl, imine, oxime, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, acylamino, aryl, heteroaryl, carbocyclyl, or heterocyclyl;

each instance of $R^8$, $R^9$, $R^{10}$, and $R^{11}$ is independently hydrogen, carbonyl, thiocarbonyl, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, acylamino, aryl, heteroaryl, carbocyclyl, or heterocyclyl;

$R^6$ is hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, or acylamino; or any two of $R^1$, $R^2$, $R^3$, $R^4$, $R^5$, and $R^6$, together with the carbon atoms to which they are attached, form an aryl, heteroaryl, carbocyclyl, or heterocyclyl; or any two of $R^7$, $R^8$, $R^9$, $R^{10}$, and $R^{11}$, together with the carbon atoms to which they are attached, form an aryl, heteroaryl, carbocyclyl, or heterocyclyl;

$R^{15}$ is hydrogen, hydroxyl, alkyl, alkenyl, alkynyl, carboxyl, sulfate, amino, alkoxy, alkylamino, alkylthio, sulfonate, sulfone, sulfoxide, acyl, acylamino, aryl, heteroaryl, carbocyclyl, heterocyclyl, aralkyl, aralkyloxy, hetaralkyl, carbocyclylalkyl, or heterocyclylalkyl; and X is hydrogen, oxo (=O), =S, =NH, =N-alkyl, =NOH, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, acylamino, aryl, heteroaryl, carbocyclyl, heterocyclyl, aralkyl, aralkyloxy, hetaralkyl, carbocyclylalkyl, or heterocyclylalkyl; or a pharmaceutically acceptable salt thereof.

In certain embodiments, the present disclosure provides pharmaceutical compositions comprising a compound of formula V, VA, VB, VI, VIA, or VIB, or a pharmaceutically acceptable salt thereof. In certain embodiments, the present disclosure provides a method of treating a proliferative disorder, comprising administering to a patient in need thereof a therapeutic amount of a compound of formula V, VA, VB, VI, VIA, or VIB, or a pharmaceutically acceptable salt thereof. These, and other embodiments, will be described in more detail herein.

DETAILED DESCRIPTION

As significantly as knowledge of cancer biology has grown over the past half-century, so too has reliance on natural products as a major source of inspiration for the development of novel chemotherapeutic agents. Indeed, more than 60% of anticancer agents developed between 1981-2014 were either natural products themselves or were derived from a natural product.[1]

One set of molecules that has contributed to this endeavor is the bis-tetrahydroisoquinoline (bis-THIQ) family of natural products, featuring jorumycin (1), ecteinascidin 743 (Et 743, 2), and saframycin A (3).[2-4] For example, Et 743 (Yondelis®, trabectidin) has been approved in the US, Europe, and elsewhere for the treatment of a variety of drug resistant and unresectable soft-tissue sarcomas and ovarian cancer. Although 2 is available from nature, isolation of one gram of material would require in excess of one ton of biological material.[5] For this reason, the successful application of 2 as an anti-tumor agent has necessitated its large-scale chemical synthesis, a daunting task for a molecule of such immense complexity.[6]

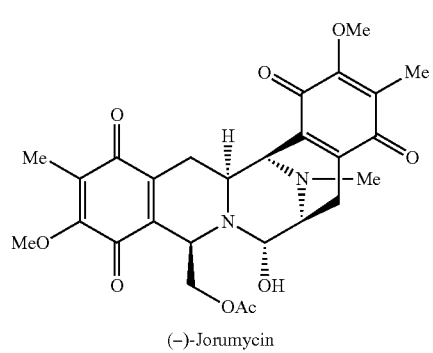

(−)-Jorumycin

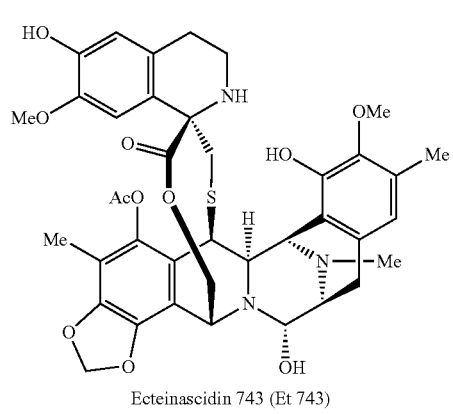

Ecteinascidin 743 (Et 743)

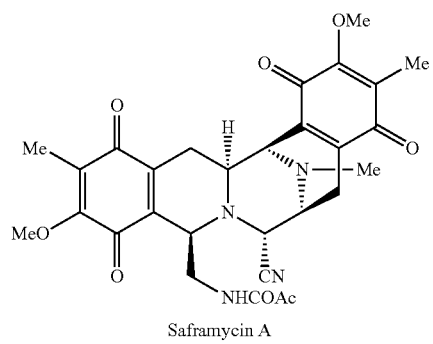

Saframycin A

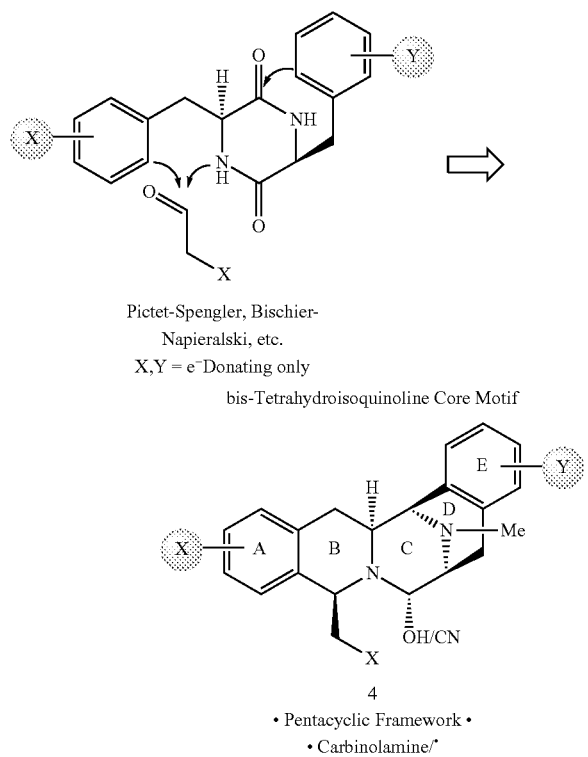

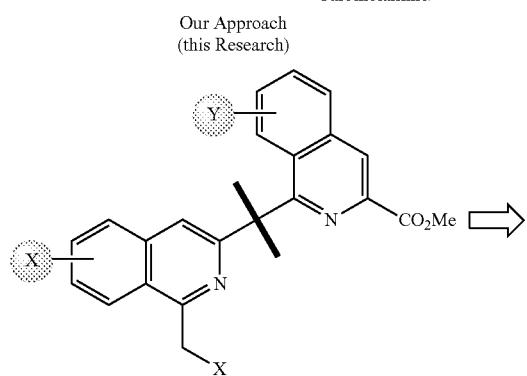

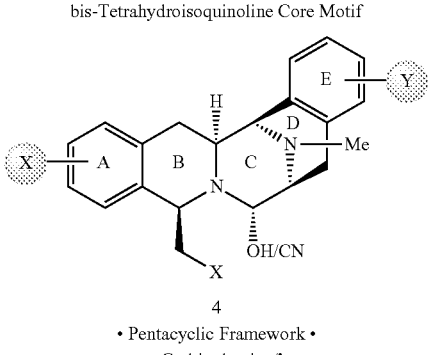

Due to their unique chemical structures, exceedingly potent biological activity, and unique mechanism of action[2-4] the bis-THIQ natural products have been studied intensively by chemists and biologists alike during the 40+ years since their initial discovery. From a synthetic standpoint, Corey and coworkers' synthesis of Et 743[7] and Myers and coworkers' synthesis of saframycin A[8] are considered landmark syntheses due to their brevity, efficiency, and creative applications of both novel and traditional chemical technology. In particular, these syntheses relied on classical electrophilic aromatic substitution (EAS) chemistry, such as the Pictet-Spengler and Bischler-Napieralski reactions, for the construction of the THIQ motifs in their respective natural products. Recent studies on the biosynthesis of compounds 2 and 3 have found that a number of non-ribosomal peptide synthetases perform nearly identical transformations in nature; these enzymes are referred to as Pictet-Spenglerases as a result.[9,10]

The highly oxygenated aromatic termini of the pentacyclic bis-THIQ core has led to a strong reliance on EAS-based strategies for the construction of the requisite THIQ subunits found in the natural products. Such approaches have allowed for the successful development of non-natural bis-THIQ analogs that possess similar levels of potency to the natural products but with greatly simplified molecular structures, most notably a quinaldic acid derivative (5)[11], phthalascidin 650[12,13], and PM-00104/50 (Zalypsis®).[14]

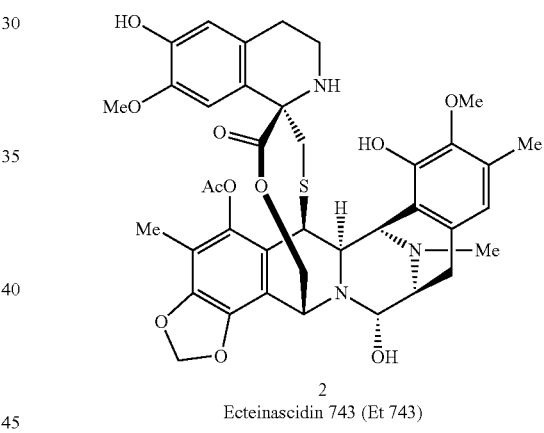

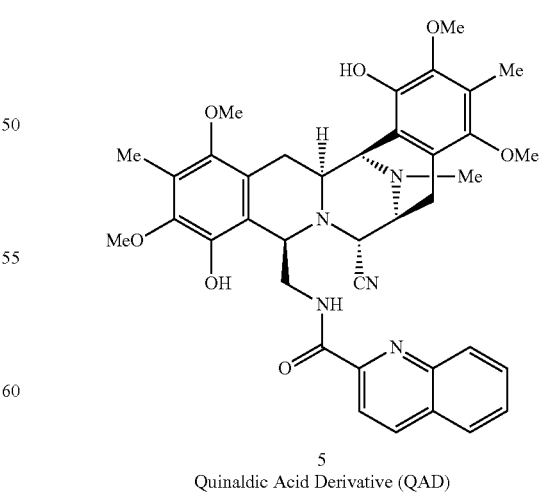

| | | |
|---|---|---|
| IC$_{50}$ (A375 melanoma) | 0.15 nM | 1.3 nM |
| IC$_{50}$ (A549 lung cancer) | 1.0 nM | 4.4 nM |
| t$_{1/2}$ (rodent) | 20 hr | 17 min |
| t$_{1/2}$ (human) | 96-180 hr | (NA) |
| EAS chemistry precludes the synthesis of electron-deficient analogs | | |
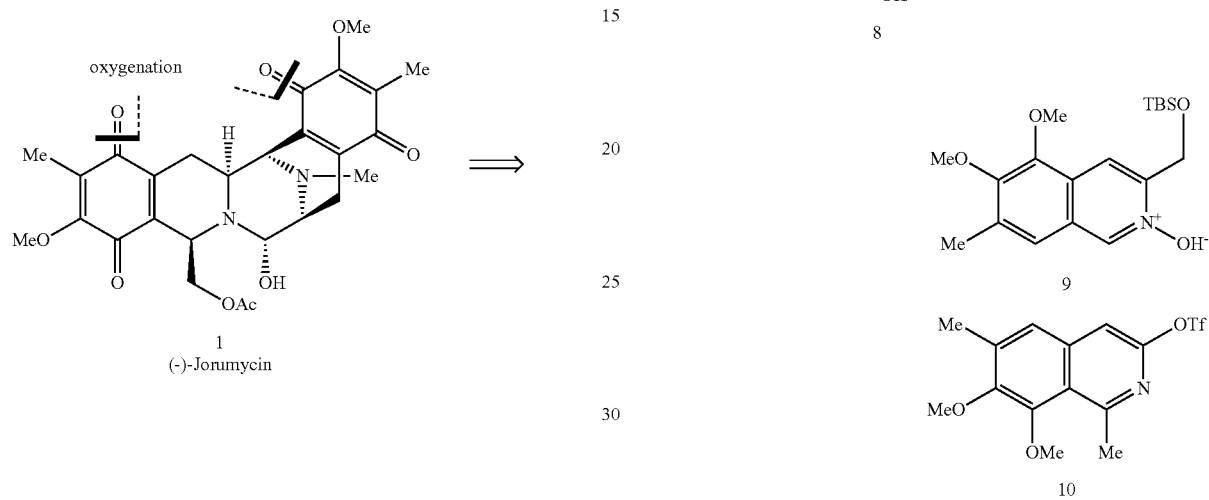
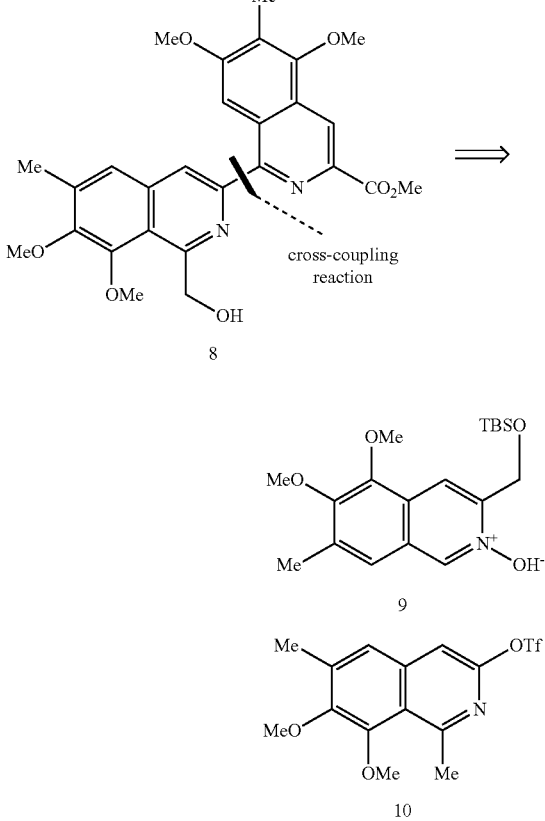
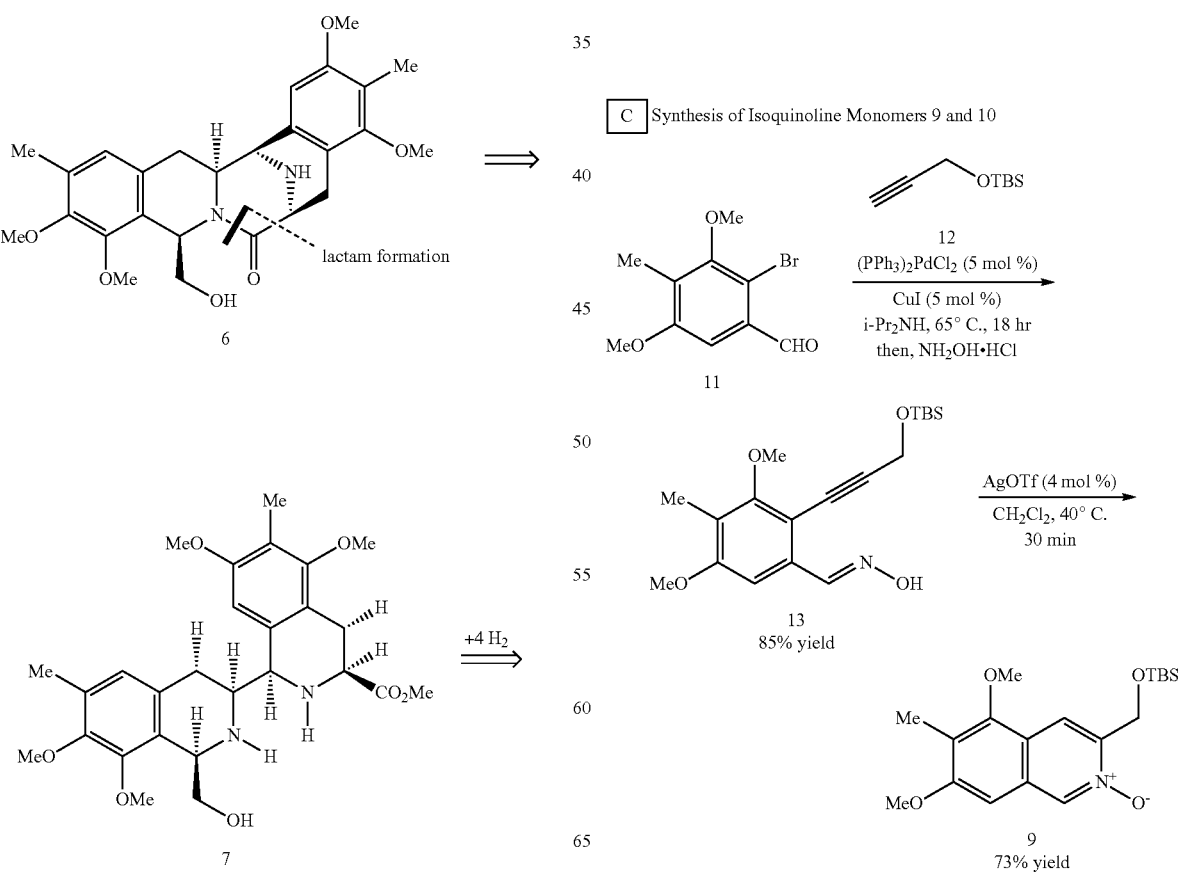

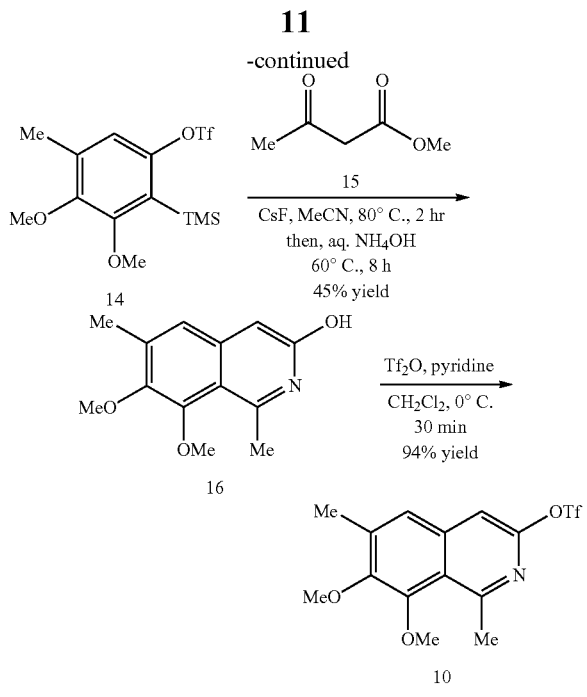

Since its isolation in 2000,[15] jorumycin been the target of a number of synthetic endeavors, including four total syntheses[16-19] and two semi-syntheses.[20,21] Similar to the strategies discussed above, EAS-based reactions have been heavily utilized in these studies. Jorumycin possesses all of the defining features of the bis-THIQ natural products—the pentacyclic carbon skeleton, the polyoxygenated ring termini, and the central carbinolamine—that together provide the marked bio-logical activity of this natural product family.[22] Furthermore, the oxygen substitution appended to the B-ring (4, X=OH) is an excellent starting point for the diversification of jorumycin to the ecteinascidin, saframycin, and renieramycin scaffolds.[2-4] Jorumycin exhibits an $IC_{50}$ of 0.24 nM vs. A549 lung cancer, 0.49 nM vs. DU145 prostate cancer, and 0.57 nM vs. HCT116 colon cancer,[15,19,20] thus offering immense therapeutic potential.

In selecting jorumycin as a target of synthetic endeavors, derivatization studies were considered.[11-14] While these studies have succeeded in producing analogs with similar potency, none has successfully navigated clinical trials to achieve approval for use in humans, whether in the US or elsewhere. One potential reason for this is a significant difference in metabolic stability. For instance, Et 743, which is a currently marketed drug, has an in vivo half-life ($t_{1/2}$) of 96-180 hours in humans and 20 hours in rodents.[23,24] In contrast, quinaldic acid saframycin A derivative 5 has a rodent in vivo half-life of just 17 minutes.[25]

It has been shown through interaction with both human and mouse liver microsomes that the bis-THIQ natural products undergo oxidation by cytochrome P450 isoform 3A4, resulting in oxidative molecular bifurcation.[26] It is important to note that although jorumycin and saframycin A possess quinone rings, these portions of the natural products are rapidly reduced in vivo through a glutathione- or NADPH-mediated pathway, resulting in the fully aromatic and very electron-rich hydroquinone forms.[22]

In view of this information, it was posited that an ideal research program directed at synthesizing new bis-THIQ analogs should aim to (1) improve or maintain potency, (2) simplify the structure of the active pharmaceutical ingredient, and (3) extend metabolic stability.

Typically, extending a drug candidate's half-life involves blocking enzymatic oxidation of the compound through the synthesis of electron-deficient analogs. For this reason, the present synthetic methodology is dissonant with conventional methods for the construction of the bis-THIQ natural products, since preparing electron-deficient analogs would be very challenging if one were to utilize a synthesis built upon EAS-based strategies. These approaches fundamentally rely on the special reactivity of electron-rich, it-nucleophilic aromatic rings, and electron-withdrawing groups tend to fully deactivate this type of chemistry. Thus, the present inventors set out to develop an orthogonal synthesis aimed at allowing access to this class of electron-deficient bis-THIQ analogs.

Compounds

In some embodiments, the present disclosure provides a method for preparing a compound of Formula (I):

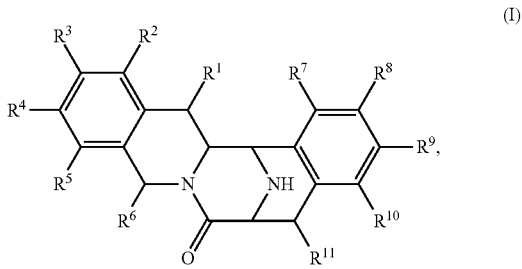

comprising contacting a compound for Formula (II):

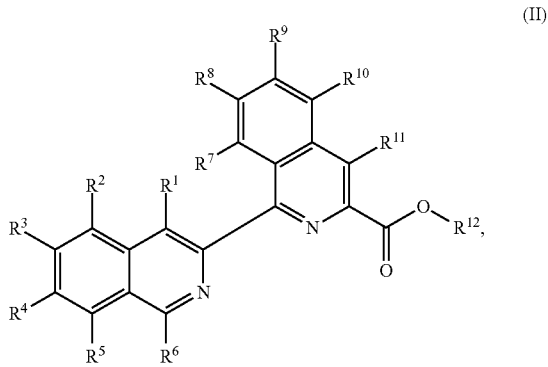

with a transition metal catalyst (preferably a chiral transition metal catalyst) under hydrogenation conditions, wherein, as valence and stability permit:

$R^1$ and $R^7$ are each independently hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, trialkylsilyloxy, or acylamino;

each instance of $R^2$, $R^3$, $R^4$, $R^5$, $R^8$, $R^9$, $R^{10}$, and $R^{11}$ is independently hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, trialkylsilyloxy, acylamino, aryl, heteroaryl, carbocyclyl, heterocyclyl aralkyl, aralkyloxy, hetaralkyl, carbocyclylalkyl, or heterocyclylalkyl;

R⁶ is hydrogen, hydroxyl, halogen, nitro, cyano, carboxyl, sulfate, alkyl, alkenyl, alkynyl, amino, alkoxy, alkylamino, alkylthio, ether, thioether, ester, amide, thioester, carbonate, carbamate, urea, sulfonate, sulfone, sulfoxide, sulfonamide, acyl, acyloxy, trialkylsilyloxy, or acylamino; or any two of R¹, R², R³, R⁴, R⁵, and R⁶, together with the carbon atoms to which they are attached, form an aryl, heteroaryl, carbocyclyl, or heterocyclyl; or any two of R⁷, R⁸, R⁹, R¹⁰, and R¹¹, together with the carbon atoms to which they are attached, form an aryl, heteroaryl, carbocyclyl, or heterocyclyl; and R¹² is H, alkyl or aralkyl.

In some embodiments, each instance of R¹, R², R³, R⁴, and R⁵ is independently unsubstituted alkyl or alkyl substituted with one or more substituents selected from hydroxy, alkoxy, acyloxy, amino, and thio.

In some embodiments, the compound has a structure of formula IA:

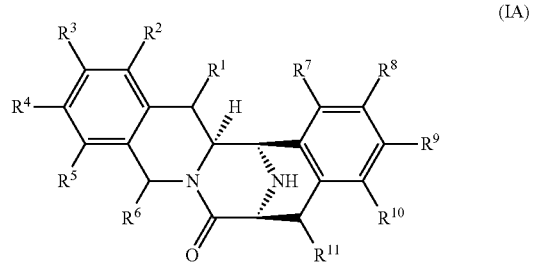

In other embodiments, the compound has a structure of formula IB:

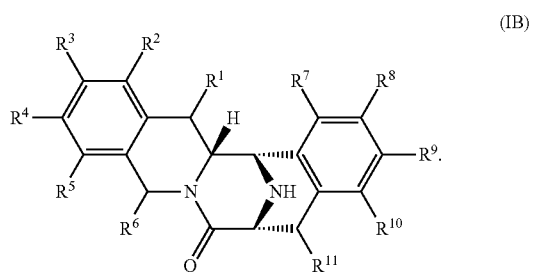

In some embodiments, the transition metal catalyst comprises an iridium complex, e.g., a catalyst prepared by combining an iridium source and a ligand (e.g., a chiral ligand). In some embodiments, the iridium source is selected from (acetylacetonato)(1,5-cyclooctadiene)iridium(I), (acetylacetonato)(1,5-cyclooctadiene)iridium(I), (acetylacetonato)dicarbonyliridium(I), bis[1,2-bis(diphenylphosphino)ethane]carbonyl chloroiridium(I), bis(1,5-cyclooctadiene)diiridium(I) dichloride, bis(1,5-cyclooctadiene)iridium(I) tetrafluoroborate, bis(cyclooctadiene)iridium(I) tetrakis(3,5-bis(trifluoromethyl)phenyl)borate, chlorobis(cyclooctene)iridium(I)dimer, (1,5-cyclooctadiene)bis(methyldiphenylphosphine)iridium(I) hexafluorophosphate, (1,5-cyclooctadiene)(hexafluoroacetylacetonato)iridium(I), (1,5-cyclooctadiene)-f 5-indenyl)iridium(I), (1,5-cyclooctadiene)(methoxy)iridium(I) dimer, (1,5-cyclooctadiene)(pyridine)(tricyclohexylphosphine)-iridium(I) hexafluorophosphate, (1,5-cyclooctadiene)(pyridine)(tricyclohexylphosphine)-iridium(I) hexafluorophosphate, and (1,5-cyclooctadiene)(pyridine)(tricyclohexylphosphine)iridium(I) tetrakis[3,5-bis(trifluoromethyl)phenyl]borate. In certain preferred embodiments, the iridium source is bis(1,5-cyclooctadiene)diiridium(I) dichloride.

In some embodiments, the chiral ligand comprises a diphosphine ligand, preferably a ferrocenyl diphosphine ligand. In some embodiments, the diphosphine ligand is selected from S—(CF₃)-t-BuPHOX, S,S-Et-FerroTANE, S,R$_p$-xyliphos, or S,R$_p$-BTFM-xyliphos, R—(CF₃)-t-BuPHOX, R,R-Et-FerroTANE, R,S$_p$-xyliphos, and R,S$_p$-BTFM-xyliphos. In certain preferred embodiments, the chiral ligand is S,R$_p$-BTFM-xyliphos or R,S$_p$-BTFM-xyliphos.

In some embodiments, the transition metal catalyst is a chiral transition metal catalyst and is used in an amount from about 0.1 mol % to about 100 mol % relative to the compound of formula (II) or (VII). In other embodiments, the transition metal catalyst is a chiral transition metal catalyst and is used in an amount from about 5 mol % to about 30 mol % relative to the compound of formula (II) or (VII). In certain embodiments, the iridium catalyst is used in an amount of about 20 mol % relative to the compound of formula (II) or (VII).

In some embodiments, the compound of formula (I) or (VIII) has about 70% ee or greater, about 80% ee or greater, about 85% ee or greater, about 88% ee or greater, about 90% ee or greater, about 91% ee or greater, about 92% ee or greater, about 93% ee or greater, about 94% ee or greater, about 95% ee or greater, about 96% ee or greater, about 97% ee or greater, about 98% ee or greater, or about 99% ee or greater.

In another aspect, the present disclosure provides a method of preparing a compound of Formula (II):

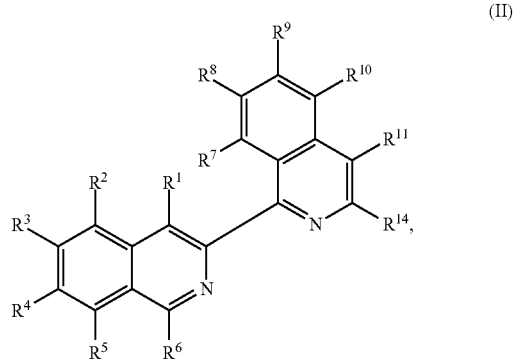

comprising reacting a compound of Formula (III):

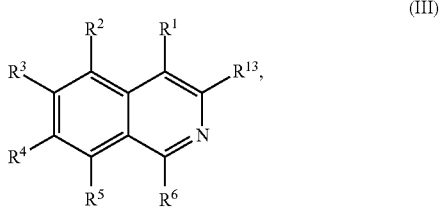

a compound of Formula (IV):

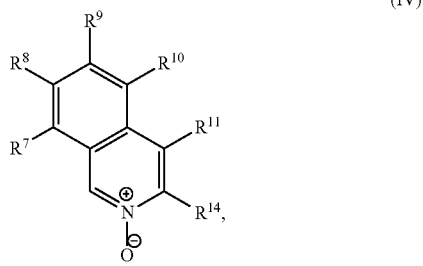

a transition metal catalyst under cross-coupling conditions, wherein, as valence and stability permit:
$R^1$ and $R^7$ are each independently hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, or acylamino;
each instance of $R^2$, $R^3$, $R^4$, $R^5$, $R^8$, $R^9$, $R^{10}$, and $R^{11}$ is independently hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, acylamino, aryl, heteroaryl, carbocyclyl, or heterocyclyl;
$R^6$ is hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, or acylamino; or
any two of $R^1$, $R^2$, $R^3$, $R^4$, $R^5$, and $R^6$, together with the carbon atoms to which they are attached, form an aryl, heteroaryl, carbocyclyl, or heterocyclyl; or
any two of $R^7$, $R^8$, $R^9$, $R^{10}$, and $R^{11}$, together with the carbon atoms to which they are attached, form an aryl, heteroaryl, carbocyclyl, or heterocyclyl; and
$R^{13}$ and $R^{14}$ are each independently hydroxyl, nitro, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, or acylamino.

In some embodiments, $R^{13}$ and $R^{14}$ are each independently unsubstituted alkyl or alkyl substituted with one or more substituents selected from hydroxy, alkoxy, acyloxy, amino and thio. In certain embodiments, $R^{14}$ is hydroxyalkyl.

In some embodiments, the transition metal catalyst comprises a nickel (e.g., Ni(COD)$_2$), palladium, or platinum catalyst. In certain embodiments, the transition metal catalyst comprises a palladium catalyst. In some embodiments, the palladium catalyst is selected from Pd/C, Pd$_2$(DBA)$_3$, Pd(PPh$_3$)$_4$, Pd(OC(O)R$^C$)$_2$, Pd(OAc)$_2$, PdCl$_2$, Pd(PhCN)$_2$Cl$_2$, Pd(CH$_3$CN)$_2$Cl$_2$, PdBr$_2$, Pd(acac)$_2$, [Pd(allyl)Cl]$_2$, Pd(TFA)$_2$, Pd$_2$(pmdba)$_3$, Pd(P(t-Bu)$_2$Me)$_2$, and pre-formed Pd(II)-ligand complexes; wherein R$^C$ is optionally substituted alkyl, alkenyl, alkynyl, aryl, heteroaryl, aralkyl, heteroaralkyl, cycloalkyl, heterocycloalkyl, (cycloalkyl)alkyl, or (heterocycloalkyl)alkyl. In certain preferred embodiments, the palladium catalyst is Pd(P(t-Bu)$_2$Me)$_2$. In some embodiments, the transition metal catalyst is used in an amount from about 0.5 mol % to about 50 mol % relative to the compound of formula (III) or (IV).

In some embodiments, $R^1$ is hydrogen. In other embodiments, $R^1$ is unsubstituted alkyl or alkyl substituted with one or more substituents selected from hydroxy, alkoxy, acyloxy, amino, and thio. In some embodiments, $R^2$ is selected from H, halo and hydroxy. In some embodiments, $R^3$ is alkyl. In other embodiments, $R^5$ is hydroxy or alkoxy. In some embodiments, $R^6$ is unsubstituted alkyl or alkyl substituted with one or more substituents selected from hydroxy, alkoxy, acyloxy, amino and thio. In some embodiments, $R^6$ is hydroxyalkyl or acyloxyalkyl, preferably CH$_2$OH.

In some embodiments, $R^7$ is unsubstituted alkyl or alkyl substituted with one or more substituents selected from hydroxy, alkoxy, acyloxy, amino, and thio. In other embodiments, $R^7$ is H, halo or hydroxy. In some embodiments, $R^8$ is alkoxy. In some embodiments, $R^9$ is alkyl. In certain embodiments, $R^{10}$ is hydroxy or alkoxy. In some embodiments, $R^{11}$ is H.

In some embodiments, each instance of $R^2$, $R^3$, $R^4$, $R^5$, $R^8$, $R^9$, $R^{10}$, and $R^{11}$ is independently unsubstituted alkyl or alkyl substituted with one or more substituents selected from hydroxy, alkoxy, acyloxy, amino, and thio.

In other embodiments, the present disclosure provides a compound of Formula (V):

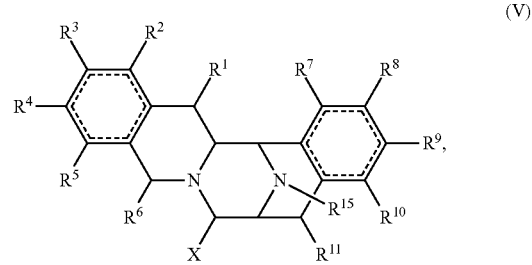

wherein:
$R^1$ and $R^7$ are each independently hydrogen, carbonyl, thiocarbonyl, imine, oxime, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, or acylamino;
each instance of $R^2$, $R^3$, $R^4$, and $R^5$ is independently hydrogen, carbonyl, thiocarbonyl, imine, oxime, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, acylamino, aryl, heteroaryl, carbocyclyl, or heterocyclyl;
each instance of $R^8$, $R^9$, $R^{10}$, and $R^{11}$ is independently hydrogen, carbonyl, thiocarbonyl, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, acylamino, aryl, heteroaryl, carbocyclyl, or heterocyclyl;
$R^6$ is hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, or acylamino; or any two of $R^1$, $R^2$, $R^3$, $R^4$, $R^5$, and $R^6$, together with the carbon atoms to which they are attached, form an aryl, heteroaryl, carbocyclyl, or heterocyclyl; or any two of $R^7$, $R^8$, $R^9$, $R^{10}$, and $R^{11}$, together with the carbon atoms to which they are attached, form an aryl, heteroaryl, carbocyclyl, or heterocyclyl;

$R^{15}$ is hydrogen, hydroxyl, alkyl, alkenyl, alkynyl, carboxyl, sulfate, amino, alkoxy, alkylamino, alkylthio, sulfonate, sulfone, sulfoxide, acyl, acylamino, aryl, heteroaryl, carbocyclyl, heterocyclyl, aralkyl, aralkyloxy, hetaralkyl, carbocyclylalkyl, or heterocyclylalkyl; and X is hydrogen, oxo (═O), ═S, ═NH, ═N-alkyl, ═NOH, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, alkylsilyloxy, acylamino, aryl, heteroaryl, carbocyclyl, heterocyclyl, aralkyl, aralkyloxy, hetaralkyl, carbocyclylalkyl, or heterocyclylalkyl;

or a pharmaceutically acceptable salt thereof.

In some embodiments, the compound has the formula (VA):

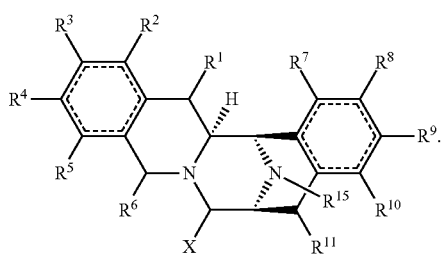

(VA)

In other embodiments, the compound has the formula (VB):

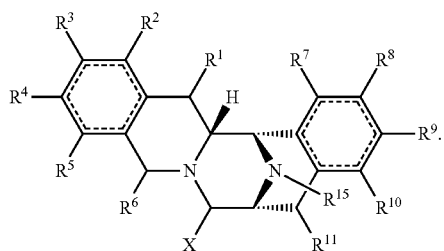

(VB)

In still other embodiments, the compound has the Formula (VI):

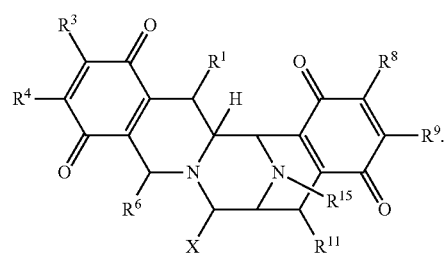

(VI)

In yet other embodiments, the compound has the Formula (VIA):

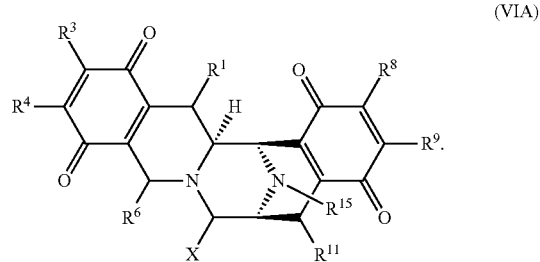

(VIA)

In other embodiments, the compound has the Formula (VIB):

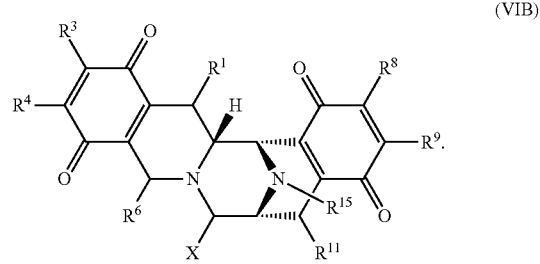

(VIB)

In some embodiments, $R^1$, $R^6$, and $R^7$ are each unsubstituted alkyl or alkyl substituted with one or more substituents selected from hydroxy, alkoxy, acyloxy, amino, and thio. In some embodiments, each instance of $R^2$, $R^3$, $R^4$, $R^5$, $R^8$, $R^9$, $R^{10}$, and $R^{11}$ is independently unsubstituted alkyl or alkyl substituted with one or more substituents selected from hydroxy, alkoxy, acyloxy, amino, and thio.

In some embodiments, $R^{15}$ is H or alkyl. In certain embodiments, $R^{15}$ is unsubstituted alkyl or alkyl substituted with one or more substituents selected from hydroxy, alkoxy, acyloxy, amino, and thio. In preferred embodiments, $R^{15}$ is methyl. In some embodiments, X is unsubstituted alkyl or alkyl substituted with one or more substituents selected from hydroxy, alkoxy, acyloxy, amino, and thio.

In some embodiments, each $R^3$, $R^4$, $R^8$, or $R^9$ is independently carbonyl, halogen, nitro, cyano, carboxyl, sulfate, amino, alkoxy, alkylamino, ester, sulfonate, sulfone, sulfoxide, acyl, haloalkyl or acyloxy. In certain embodiments, each $R^3$, $R^4$, $R^8$, or $R^9$ is independently carbonyl, halogen, nitro, cyano, carboxyl, ester, acyl, haloalkyl or acyloxy.

In certain embodiments, the compound may be a prodrug, e.g., wherein a hydroxyl in the parent compound is presented as an ester or a carbonate, a carboxylic acid present in the parent compound is presented as an ester, or an amino group is presented as an amide. In certain such embodiments, the prodrug is metabolized to the active parent compound in vivo (e.g., the ester is hydrolyzed to the corresponding hydroxyl or carboxylic acid).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, 95% ee, 96% ee, 97% ee, 98% ee, 99% or greater ee. The compounds of the invention have more than one stereocenter.

Accordingly, the compounds of the invention may be enriched in one or more diastereomers. For example, a compound of the invention may have greater than 30% de, 40% de, 50% de, 60% de, 70% de, 80% de, 90% de, 95% de, 96% de, 97% de, 98% de, 99% or greater de. In certain embodiments, the compounds of the invention have substantially one isomeric configuration at one or more stereogenic centers, and have multiple isomeric configurations at the remaining stereogenic centers.

In certain embodiments, a therapeutic preparation of the compound of the invention may be enriched to provide predominantly one enantiomer of a compound. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer. In certain embodiments, a therapeutic preparation may be enriched to provide predominantly one diastereomer of the compound of the invention. A diastereomerically enriched mixture may comprise, for example, at least 60 mol percent of one diastereomer, or more preferably at least 75, 90, 95, or even 99 mol percent.

In certain embodiments, the bis-THIQ compounds of the invention exhibit an improved pharmacokinetic profile relative to existing bis-THIQs.

In certain embodiments, the bis-THIQ compounds of the invention exhibit improved bioavailability relative to existing bis-THIQs.

Transition Metal Catalysts

Preferred transition metal catalysts of the invention are complexes of iridium. In some embodiments, the transition metal catalyst is an iridium catalyst.

In some embodiments, the iridium catalyst is prepared by combining an iridium source and a chiral ligand. In preferred embodiments the iridium catalyst is prepared by combining an iridium source and a chiral ligand.

Exemplary iridium sources that may be used in the methods of the invention include, but are not limited to, (acetylacetonato)(1,5-cyclooctadiene)iridium(I), (acetylacetonato)(1,5-cyclooctadiene)iridium(I), (acetylacetonato)dicarbonyliridium(I), bis[1,2-bis(diphenylphosphino)ethane] carbonyl chloroiridium(I), bis(1,5-cyclooctadiene)diiridium(I) dichloride, bis(1,5-cyclooctadiene)iridium(I) tetrafluoroborate, bis(cyclooctadiene)iridium(I) tetrakis(3,5-bis(trifluoromethyl)phenyl)borate, chlorobis(cyclooctene)iridium(I)dimer, (1,5-cyclooctadiene)bis(methyldiphenylphosphine)iridium(I) hexafluorophosphate, (1,5-cyclooctadiene)(hexafluoroacetylacetonato)iridium(I), (1,5-cyclooctadiene)-15-indenyl)iridium(I), (1,5-cyclooctadiene)(methoxy)iridium(I) dimer, (1,5-cyclooctadiene)(pyridine)(tricyclohexylphosphine)-iridium(I) hexafluorophosphate, (1,5-cyclooctadiene)(pyridine)(tricyclohexylphosphine)-iridium(I) hexafluorophosphate, and (1,5-cyclooctadiene)(pyridine)(tricyclohexylphosphine)iridium(I) tetrakis[3,5-bis(trifluoromethyl)phenyl]borate. In preferred embodiments, the iridium source is bis(1,5-cyclooctadiene) diiridium(I) dichloride.

Accordingly, when describing the amount of transition metal catalyst used in the methods of the invention, the following terminology applies. The amount of transition metal catalyst present in a reaction is alternatively referred to herein as "catalyst loading". Catalyst loading may be expressed as a percentage that is calculated by dividing the moles of catalyst complex by the moles of the substrate present in a given reaction. Catalyst loading is alternatively expressed as a percentage that is calculated by dividing the moles of total transition metal (for example, iridium) by the moles of the substrate present in a given reaction.

In certain embodiments, the transition metal catalyst is present under the conditions of the reaction from an amount of about 0.01 mol % to about 30 mol % total iridium relative to the substrate, such as the compound of formula (II) or (VII). In certain embodiments, the catalyst loading is from about 0.05 mol % to about 25 mol % total iridium relative to the substrate. In certain embodiments, the catalyst loading is from about 0.1 mol % to about 25 mol %, about 1 mol % to about 25 mol % about 5 mol % to about 22 mol % about 10 mol % to about 20 mol %, about 15 mol % to about 20 mol total iridium relative to the substrate. In preferred embodiments, the catalyst loading is about 20 mol % total iridium.

Chiral Ligands

One aspect of the invention relates to the enantioselectivity of the methods. Enantioselectivity results from the use of chiral ligands during the hydrogenation reaction. Accordingly, the iridium catalyst comprises a chiral ligand. Without being bound by theory, the asymmetric environment that is created around the metal center by the presence of chiral ligands produces an enantioselective reaction. The chiral ligand forms a complex with the transition metal (i.e., iridium), thereby occupying one or more of the coordination sites on the metal and creating an asymmetric environment around the metal center. This complexation may or may not involve the displacement of achiral ligands already complexed to the metal. When displacement of one or more achiral ligands occurs, the displacement may proceed in a concerted fashion, i.e., with both the achiral ligand decomplexing from the metal and the chiral ligand complexing to the metal in a single step. Alternatively, the displacement may proceed in a stepwise fashion, i.e., with decomplexing of the achiral ligand and complexing of the chiral ligand occurring in distinct steps. Complexation of the chiral ligand to the transition metal may be allowed to occur in situ, i.e., by admixing the ligand and metal before adding the substrate. Alternatively, the ligand-metal complex can be formed separately, and the complex isolated before use in the alkylation reactions of the present invention.

Once coordinated to the transition metal center, the chiral ligand influences the orientation of other molecules as they interact with the transition metal catalyst. Coordination of the metal center with a π-allyl group and reaction of the substrate with the π-allyl-metal complex are dictated by the presence of the chiral ligand. The orientation of the reacting species determines the stereochemistry of the products.

Chiral ligands of the invention may be bidentate or monodentate or, alternatively, ligands with higher denticity (e.g., tridentate, tetradentate, etc.) can be used. In preferred embodiments, the ligand is a bidentate ligand. Additionally, it is preferred that the ligand be substantially enantiopure. By "enantiopure" is meant that only a single enantiomer is present. In many cases, substantially enantiopure ligands (e.g., ee >99%, preferably ee >99.5%, even more preferably ee >99.9%) can be purchased from commercial sources, obtained by successive recrystallizations of an enantioenriched substance, or by other suitable means for separating enantiomers.

Exemplary chiral ligands may be found in U.S. Pat. No. 7,863,443 and CN Patent No. 105524111B, the entireties of which are incorporated herein by reference. In certain embodiments, the chiral ligand is an enantioenriched phosphine ligand. In certain embodiments, the enantioenriched phosphorus-based ligand is a phosphoramidite ligand. In certain such embodiments, the transition metal complex with the ligand comprises S—($CF_3$)-t-BuPHOX, S,S-Et-FerroTANE, S,$R_p$-Xyliphos, or S,$R_p$-BTFM-xyliphos. In other embodiments, the transition metal complex with the ligand comprises R—($CF_3$)-t-BuPHOX, R,R-Et-FerroTANE, R,$S_p$-Xyliphos, or R,$S_p$-BTFM-xyliphos.

Generally, the chiral ligand is present in an amount in the range of about 1 equivalent to about 20 equivalents relative to the amount of total metal from the catalyst, preferably in the range of about 1 to about 15 equivalents relative to the amount of total metal from the catalyst, and most preferably about 1 equivalent relative to the amount of total metal from the catalyst. Alternatively, the amount of the chiral ligand can be measured relative to the amount of the substrate.

In certain embodiments, the ligand is present under the conditions of the reaction from an amount of about 5 mol % to about 80 mol % relative to the substrate, e.g., the compound of formula (II) or formula (VII). The amount of the chiral ligand present in the reaction is alternatively referred to herein as "ligand loading" and is expressed as a percentage that is calculated by dividing the moles of ligand by the moles of the substrate present in a given reaction. In certain embodiments, the ligand loading is from about 5 mol %, about 6 mol %, about 7 mol %, about 10 mol %, about 12 mol %, about 14 mol %, about 16 mol %, about 18 mol %, about 19 mol %, about 19.5 mol %, about 19.8 mol %, about 20 mol %, about 20.2 mol %, about 20.5 mol %, about 20.8 mol %, about 21 mol %, about 21.2 mol %, about 21.4 mol %, about 21.8 mol %, about 22 mol %, about 25 mol %, about 28 mol %, about 30 mol %, about 35 mol %, about 40 mol %, about 45 mol %, about 50 mol %, about 55 mol %, about 58 mol %, about 60 mol %, or about 70 mol %. In preferred embodiments, the ligand loading is 21 mol %.

Where a chiral ligand is used, the reactions of the invention may create multiple stereocenters in the product compound, such as the compound of Formula (I), (V) or (VI), in a high degree of enantiomeric excess (ee). The ee of a compound may be measured by dividing the difference in the fractions of the enantiomers by the sum of the fractions of the enantiomers. For example, if a compound is found to comprise 98% (S)-enantiomer, and 2% (R) enantiomer, then the ee of the compound is (98−2)/(98+2), or 96%. In certain embodiments, the compound of formula (I), (V) or (VI) has about 30% ee or greater, about 40% ee or greater, about 50% ee or greater, 60% ee or greater, about 70% ee or greater, about 80% ee or greater, about 85% ee or greater, about 88% ee or greater, about 90% ee or greater, about 91% ee or greater, about 92% ee or greater, about 93% ee or greater, about 94% ee or greater, about 95% ee or greater, about 96% ee or greater, about 97% ee or greater, about 98% ee or greater, or about 99% ee or greater, even where this % ee is greater than the % ee of the starting material, such as 0% ee (racemic).

Methods of Treatment

In certain embodiments, the present disclosure provides methods for treating or preventing cancer, comprising administering to a subject in need thereof a therapeutically effective amount of a compound of the invention (e.g., a compound of Formula V, VA, VB, VI, VIA, or VIB), or a pharmaceutical composition comprising said compound.

In certain embodiments, the cancer that is treated by the methods of the invention is Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Extracranial Germ Cell Tumor, Extragonadal Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CML), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Renal Pelvis Cancer, Ureter Cancer, Transitional Cell Cancer, Retinoblastoma, Rhabdomyosarcoma, Salivary Gland Cancer, Sarcoma, Sezary Syndrome, Skin Cancer, Small Cell Lung Cancer, Small Intestine Cancer, Soft Tissue Sarcoma, Squamous Cell Carcinoma, Squamous Neck Cancer with Occult Primary, Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Gestational Trophoblastic Tumor, Unknown Primary, Unusual Cancer of Childhood, Urethral Cancer, Uterine Cancer, Uterine Sarcoma, Waldenström Macroglobulinemia, or Wilms Tumor.

In certain embodiments, the cancer that is treated by the methods of the invention is a variety of acute myeloid leukemia (AML), bladder cancer, breast cancer, colorectal cancer, chronic myelogenous leukemia (CML), esophageal cancer, gastric cancer, lung cancer, melanoma, mesothelioma, non-small cell lung carcinoma (NSCLC), ovarian cancer, pancreatic cancer, prostate cancer, renal cancer, or skin cancer.

In certain embodiments, the cancer that is treated by the methods of the invention is a variety of acute myeloid leukemia (AML), breast cancer, colorectal cancer, chronic myelogenous leukemia (CML), esophageal cancer, gastric cancer, lung cancer, melanoma, non-small cell lung carcinoma (NSCLC), pancreatic cancer, prostate cancer, or renal cancer.

In certain embodiments, the cancer is selected from bladder cancer, breast cancer (including TNBC), cervical cancer, colorectal cancer, chronic lymphocytic leukemia (CLL), diffuse large B-cell lymphoma (DLBCL), esophageal adenocarcinoma, glioblastoma, head and neck cancer, leukemia (acute and chronic), low-grade glioma, lung cancer (including adenocarcinoma, non-small cell lung cancer, and squamous cell carcinoma), Hodgkin's lymphoma, non-Hodgkin lymphoma (NHL), melanoma, multiple myeloma (MM), ovarian cancer, pancreatic cancer, prostate cancer, renal cancer (including renal clear cell carcinoma and kidney papillary cell carcinoma), and stomach cancer.

Combination therapy is an important treatment modality in many disease settings, such as cancer. Recent scientific advances have increased our understanding of the pathophysiological processes that underlie these and other complex diseases. This increased understanding has provided impetus to develop new therapeutic approaches using combinations of drugs directed at multiple therapeutic targets to improve treatment response, minimize development of resistance, or minimize adverse events. In settings in which combination therapy provides significant therapeutic advantages, there is growing interest in the development of combinations with new investigational drugs, such as bis-THIQs.

When considering the administration of multiple therapeutic agents together, one must be concerned about what sort of drug interactions will be observed. This action can be positive (when the drug's effect is increased) or antagonistic (when the drug's effect is decreased) or a new side effect can be produced that neither produces on its own.

When the interaction causes an increase in the effects of one or both of the drugs the interaction, the degree to which the final effect of the combined drugs is greater than administering either drug alone can be calculated resulting in what is called the "combination index" (CI) (see, e.g., Chou and Talalay, 1984). A combination index at or around 1 is considered "additive"; whereas a value greater than 1 is considered "synergistic".

The present invention provides methods for combination therapy in treating or preventing cancer comprising an bis-THIQ (e.g., a compound of the invention) and one or more additional chemotherapeutic agents.

Certain embodiments of the invention relate to treating cancer comprising conjointly administering a chemotherapeutic agent and a compound of the invention.

In certain embodiments, the chemotherapeutic is an immune-stimulating agent. For example, the immune-stimulating agent may be a pro-inflammatory agent.

The chemotherapeutic agent that may be conjointly administered with the bis-THIQs described herein in the methods of the invention include aminoglutethimide, amsacrine, anastrozole, asparaginase, AZD5363, Bacillus Calmette-Guérin vaccine (bcg), bicalutamide, bleomycin, bortezomib, buserelin, busulfan, campothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epacadostat, epirubicin, erlotinib, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, nilutamide, nocodazole, octreotide, olaparib, oxaliplatin, paclitaxel, pamidronate, pazopanib, pentostatin, perifosine, plicamycin, pomalidomide, porfimer, procarbazine, raltitrexed, rituximab, rucaparib, selumetinib, sorafenib, streptozocin, sunitinib, suramin, talazoparib, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, or vinorelbine.

In certain embodiments, the chemotherapeutic agent that may be administered with the bis-THIQs described herein in the methods of the invention include abagovomab, adecatumumab, afutuzumab, anatumomab mafenatox, apolizumab, atezolizumab, blinatumomab, catumaxomab, durvalumab, epacadostat, epratuzumab, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, or tremelimumab.

In certain embodiments, the chemotherapeutic agent is ipilimumab, nivolumab, pembrolizumab, or pidilizumab.

Many combination therapies have been developed for the treatment of cancer. In certain embodiments, compounds of the invention may be conjointly administered with a combination therapy. Examples of combination therapies with which compounds of the invention may be conjointly administered are included in Table 1.

TABLE 1

Exemplary combinatorial therapies for the treatment of cancer.

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |

TABLE 1-continued

Exemplary combinatorial therapies for the treatment of cancer.

| Name | Therapeutic agents |
|---|---|
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |

TABLE 1-continued

Exemplary combinatorial therapies for the treatment of cancer.

| Name | Therapeutic agents |
|---|---|
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/ cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Flourouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

Immune-targeted agents (also known as immuno-oncology agents) act against tumors by modulating immune cells. The field of cancer immunotherapy is rapidly growing, with new targets constantly being identified (Chen and Mellman, 2013; Morrissey et al., 2016; Kohrt et al., 2016).

Examples of immuno-oncology agents comprise agents that modulate immune checkpoints such as 2B4, 4-1BB (CD137), AaR, B7-H3, B7-H4, BAFFR, BTLA, CD2, CD7, CD27, CD28, CD30, CD40, CD80, CD83 ligand, CD86, CD160, CD200, CDS, CEACAM, CTLA-4, GITR, HVEM, ICAM-1, KIR, LAG-3, LAIR1, LFA-1 (CD11a/CD18), LIGHT, NKG2C, NKp80, OX40, PD-1, PD-L1, PD-L2, SLAMF7, TGFRβ, TIGIT, Tim3 and VISTA. Immuno-oncology agents may be in the form of antibodies, peptides, small molecules or viruses.

In some embodiments, the conjointly administered chemotherapeutic agent is an immuno-oncology therapeutic agent, such as an inhibitor of arginase, CTLA-4, indoleamine 2,3-dioxygenase, and/or PD-1/PD-L1. In certain embodiments, the immuno-oncology therapeutic agent is abagovomab, adecatumumab, afutuzumab, alemtuzumab, anatumomab mafenatox, apolizumab, atezolizumab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, ocaratuzumab, ofatumumab, olatatumab, pembrolizumab, pidilizumab, rituximab, ticilimumab, samalizumab, or tremelimumab. Alternatively, the immuno-oncology therapeutic agent is abagovomab, adecatumumab, afutuzumab, anatumomab mafenatox, apolizumab, atezolizumab, blinatumomab, catumaxomab, durvalumab, epacadostat, epratuzumab, indoximod, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, or tremelimumab.

Exemplary immuno-oncology agents are disclosed in Adams, J. L. et al. "Big Opportunities for Small Molecules in Immuno-Oncology" *Nature Reviews Drug Discovery* 2015, 14, page 603-621, the contents of which are hereby incorporated by reference.

In certain embodiments, the conjointly administered chemotherapeutic agent is a pro-inflammatory agent. In certain embodiments, the pro-inflammatory agent administered with the bis-THIQs of the invention is a cytokine or a chemokine.

Pro-inflammatory cytokines are produced predominantly by activated macrophages and are involved in the up-regulation of inflammatory reactions. Exemplary pro-inflammatory cytokines include IL-1, IL-113, IL-6, IL-8, TNF-α, and IFN-γ.

Chemokines are a group of small cytokines. Pro-inflammatory chemokines promote recruitment and activation of multiple lineages of leukocytes (e.g., lymphocytes, macrophages). Chemokines are related in primary structure and share several conserved amino acid residues. In particular, chemokines typically include two or four cysteine residues that contribute to the three-dimensional structure via formation of disulfide bonds. Chemokines may be classified in one of four groups: C—C chemokines, C—X—C chemokines, C chemokines, and C—$X_3$—C chemokines. C—X—C chemokines include a number of potent chemoattractants and activators of neutrophils, such as interleukin 8 (IL-8), PF4 and neutrophil-activating peptide-2 (NAP-2). The C—C chemokines include, for example, RANTES (Regulated on Activation, Normal T Expressed and Secreted), macrophage inflammatory proteins 1-alpha and 1-beta (MIP-1α and MIP-1β), eotaxin and human monocyte chemotactic proteins 1 to 3 (MCP-1, MCP-2, MCP-3), which have been characterized as chemoattractants and activators of monocytes or lymphocytes. Accordingly, exemplary pro-inflammatory chemokines include MIP-1α, MIP-1β, MIP-1γ, MCP-1, MCP-2, MCP-3, IL-8, PF4, NAP-2, RANTES, CCL2, CCL3, CCL4, CCL5, CCL11, CXCL2, CXCL8, and CXCL10.

In certain embodiments, the method of treating or preventing cancer further comprises administering one or more non-chemical methods of cancer treatment, such as radiation therapy, surgery, thermoablation, focused ultrasound therapy, cryotherapy, or a combination of the foregoing.

In certain embodiments of the invention, the chemotherapeutic agent is administered simultaneously with the bis-THIQ. In certain embodiments, the chemotherapeutic agent is administered within about 5 minutes to within about 168 hours prior or after of the bis-THIQ.

In certain embodiments, the step of administering comprises oral administration of the therapeutic agent. Alternatively, the step of administering can comprise parenteral administration of the therapeutic agent. Further methods of administration are discussed herein.

In certain embodiments, the subject is a human.

In certain embodiments, the therapeutic agent is a compound of Formula V, VA, VB, VI, VIA, or VIB. Exemplary compounds are described herein.

The present invention also provides a method for treating or preventing cancer, comprising conjointly administering to a subject in need thereof a therapeutically effective amount of a compound of Formula V, VA, VB, VI, VIA, or VIB and one or more additional chemotherapeutic agents.

In certain embodiments, the combination therapy regimen is more efficacious than a therapy regimen of the bis-THIQ agent (e.g., a compound of Formula V, VA, VB, VI, VIA, or VIB) as a single agent, or a therapy regimen of the additional chemotherapeutic agent as a single agent.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing one or more hydrogens on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a guanidino, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. Co alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

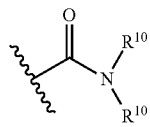

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

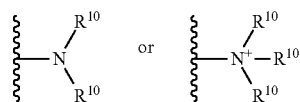

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

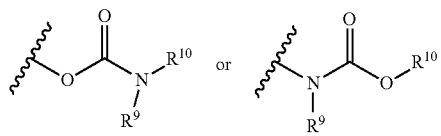

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "(cycloalkyl)alkyl", as used herein, refers to an alkyl group substituted with a cycloalkyl group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —C(O)O$R^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The term "heteroaralkyl", as used herein, refers to an alkyl group substituted with a heteroaryl group.

The term "heteroalkyl", as used herein, refers to a saturated or unsaturated chain of carbon atoms and at least one heteroatom, wherein no two heteroatoms are adjacent.

The term "heteroaryl" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocycloalkyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocycloalkyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocycloalkyl groups include, for example, piperidine, piperazine, pyrrolidine, morpholine, lactones, lactams, and the like.

The term "(heterocycloalkyl)alkyl", as used herein, refers to an alkyl group substituted with a heterocycloalkyl group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

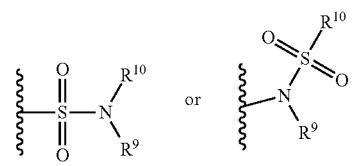

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

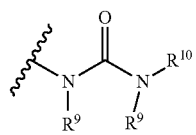

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of Formula V, VA, VB, VI, VIA, or VIB). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. Alternatively, amides (e.g., an amide of an amino group) may be a prodrug of the invention. In certain embodiments, some or all of the active compounds in a formulation represented above can be replaced with the corresponding suitable prodrug, e.g., wherein a hydroxyl in the parent compound is presented as an ester or a carbonate or carboxylic acid present in the parent compound is presented as an ester.

Pharmaceutical Compositions

In certain embodiments, the invention provides a pharmaceutical composition comprising a compound of the invention (e.g., a compound of Formula V, VA, VB, VI, VIA, or VIB), or a pharmaceutically acceptable salt thereof; and a pharmaceutically acceptable carrier.

In certain embodiments, the present invention provides a pharmaceutical preparation suitable for use in a human patient, comprising any compound of the invention (e.g., a compound of Formula V, VA, VB, VI, VIA, or VIB), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

One embodiment of the present invention provides a pharmaceutical kit comprising a compound of the invention (e.g., a compound of Formula V, VA, VB, VI, VIA, or VIB), or a pharmaceutically acceptable salt thereof, and optionally directions on how to administer the compound.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In certain preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ (e.g., wheat germ), olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., a compound of Formula V, VA, VB, VI, VIA, or VIB) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, oxalic, mandelic and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of formula V, VA, VB, VI, VIA, or VIB. As another example, the salt may comprise less than one inorganic or organic acid molecule per molecule of base, such as two molecules of compound of Formula V, VA, VB, VI, VIA, or VIB per molecule of tartaric acid.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benethamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.
Retrosynthetic Analysis and Synthetic Methodology To achieve the synthesis of jorumycin and related compounds, the retrosynthetic strategy shown above was developed. As shown, a late stage oxygenation event would provide jorumycin and would greatly simplify the construction of starting materials, providing pentacycle 6. We then disconnected the central C-ring through cleavage of the lactam moiety in 6, providing bis-THIQ compound 7, which we believed could be synthesized through the enantioselective hydrogenation of bis-isoquinoline 8. The biaryl nature of 8 naturally suggests that it be formed through a cross-coupling reaction, leading to isoquinoline monomers 9 and 10. As a key advantage, isoquinolines 9 and 10 could be synthesized through known methods, not limited to those utilizing highly electron-rich and it-nucleophilic species. Crucially, this approach would allow access to the natural products themselves, as well as electron-rich, -neutral, or -deficient non-natural analogs.

To initiate our synthetic studies we focused our attention on the construction of isoquinoline monomer 9. Sonagashira coupling of aryl bromide 11, available in two steps from 3,5-dimethoxy-benzaldehyde, with tert-butyldimethylsilyl propargyl alcohol[12] proceeded smoothly; simply adding solid hydroxylamine hydrochloride to the reaction mixture after the coupling provided oxime-bearing alkyne 13 in 85% yield. Catalytic silver(I) triflate served to activate the alkyne toward nucleophilic attack by the oxime, directly generating isoquinoline N-oxide 9 in 73% yield on up to a 12-gram scale in a single pass.[27]

Next, we began our synthesis of isoquinoline triflate 10 by using aryne-based technology developed in our laboratories.[28-30] Silyl aryl triflate 14, available in 3-steps from 2,3-dimethoxytoluene, was treated with cesium fluoride to provide the corresponding aryne intermediate (not shown), which under-went aryne acyl-alkylation with in situ condensation to provide 3-hydroxyisoquinoline 16 in 81% yield. Reaction with trifluo-romethanesulfonic anhydride provides electrophilic coupling partner 10 in 94% yield.

With working routes to both iso-quinoline monomers in hand, we turned our attention to the cross-coupling reaction which would be used to construct the carbon skeleton of jorumycin. We were pleased to find that isoquinolines 9 and 10 were efficiently coupled under the conditions developed by Fagnou and coworkers to provide bis-isoquinoline 18 in 94% yield on a seven gram scale.[31] This large-scale application of C—H activation proceeds through transition state 17 and allows for the direct construction of 18 without need for prefuctionalization. Importantly, while an excess of N-oxide 9 is required to achieve the maximum efficiency, this appears to be necessary only for kinetic reasons, as all excess 9 is recovered after the reaction.

At this stage, we recognized that the Boekelheide rearrangement[33,34] would be particularly well suited for the advance-ment of our synthesis, utilizing the oxidation already present in the molecule. Prior to implementing of this rearrange-ment, we oxidized the remaining azine using methyltrioxorhenium(VII) and hydrogen peroxide[35] to provide bis-N-oxide 19 in 98% yield with no purification necessary. This species can then undergo a double Boekelheide rearrangement in refluxing acetic anhydride, transmuting the N-oxides to the benzylic acetates. This provides triacetoxy compound 20, which undergoes partial hydrolysis under the reaction conditions to aldehyde 21; subsequent treatment with aqueous lithium hydroxide converges all material to 21 in 34% yield. Oxidation with silver(I) oxide provides the methyl ester, and the addition of thionyl chloride induces methanolysis of the primary acetate to provide hydro-genation precursor 22 in just three steps.

We were now ready to explore the key hydrogenation event that would form eight new C—H and N—H bonds, including four of the five necessary stereocenters, as well as close the C-ring lactam after full hydro-genation. While the enantioselective hy-drogenation of nitrogen-based heterocycles is a well-studied field, isoquinolines are perhaps the most challenging substrates for this transformation.[36] One reason for this is that the products of reduction are highly basic and are known to poison most homogeneous transition metal catalysts. Indeed, to our knowledge only four reports exist which describe enantioselective iso-quinoline hydrogenation protocols, only one of which is applicable to 1,3-disub-stituted systems.[37-40]
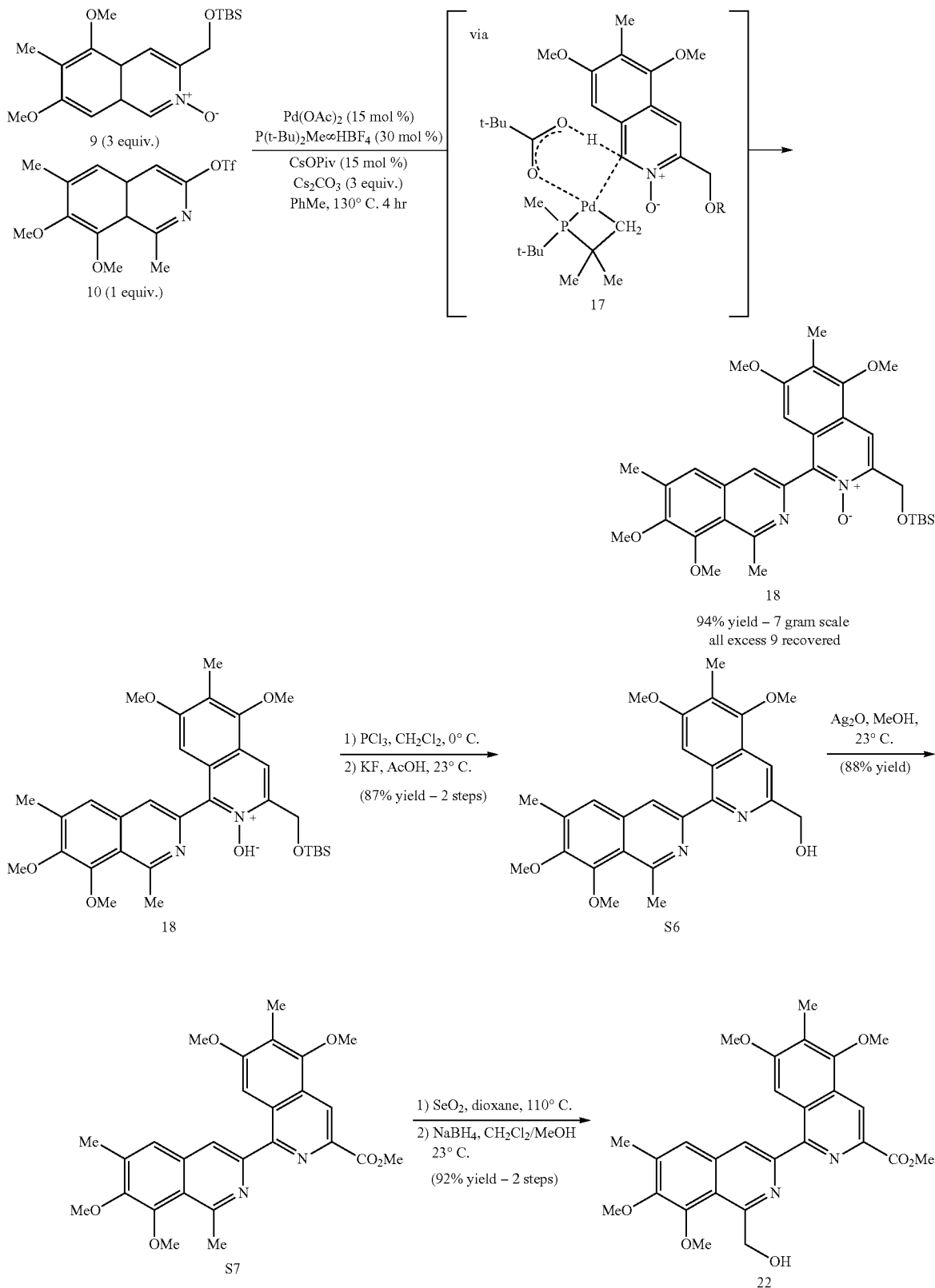

B. Stereochemical Rationale for the Hydrogenation of 22

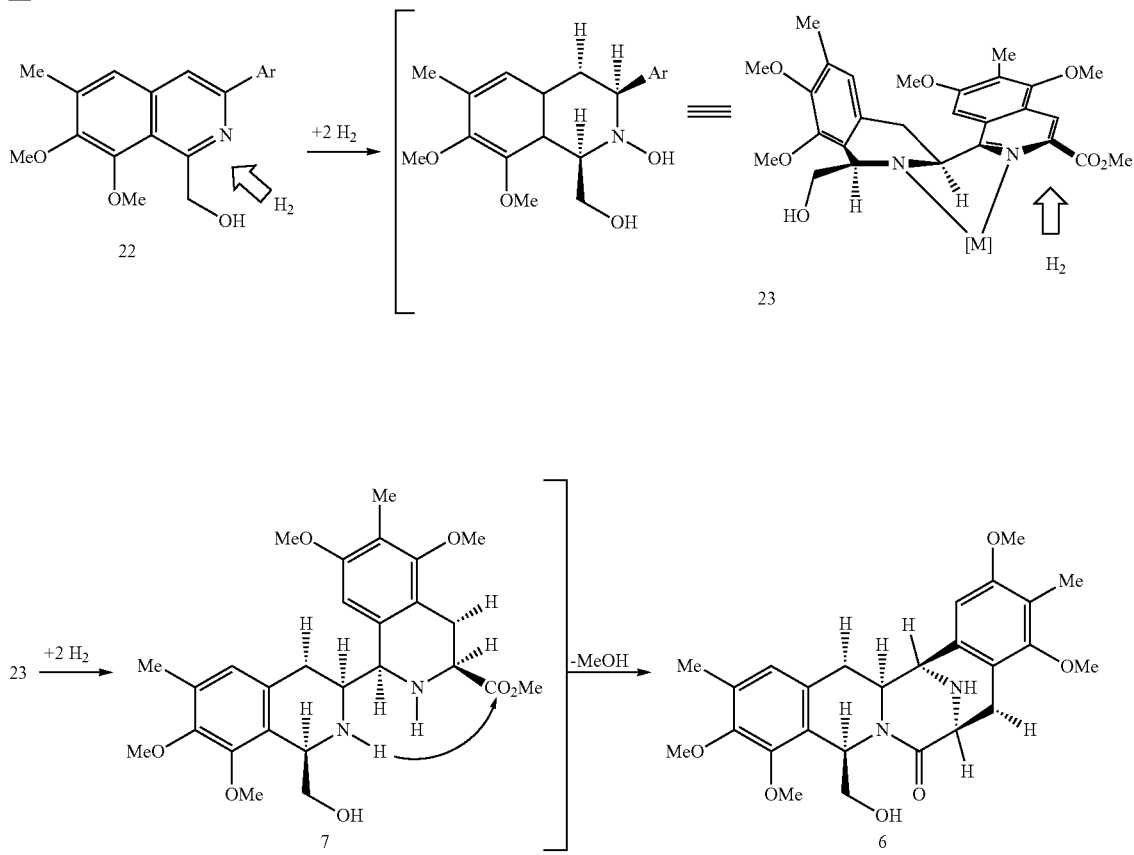

Our stereochemical rationale for this transformation is depicted above. We predicted that the hydroxyl directing group would serve to both accelerate the reduction of the B-ring relative to the D-ring (cf 4) and to serve as a scaffold to direct a chiral catalyst to only a single face of the aromatic system. Reduction of 1,3-disubstituted isoquinolines is known to proceed with high syn diastereoselectivity, so we anticipate the major product after the first two additions of dihydrogen to be cis-mono-THIQ 23.[36-40] We believed that 23 could act as a bidentate ligand for the metal catalyst, the three-dimensional structure of which would direct D-ring hydrogenation from the same face. This form of substrate-reinforced diastereoselectivity predicts the addition of all four molecules of hydrogen from the same face. Finally, the all-syn nature of 7 places it in close proximity to the amine in the B-ring, and we expected lactamization to be rapid.

Development of Enantioselective Hydrogenation

TABLE 1

Development of Enantioselective Hydrogenation.

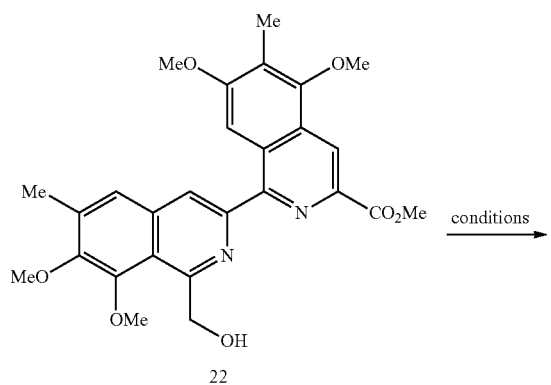 [SMILES: COC(=O)c1cc2c(OC)c(C)c(OC)cc2c(-c2cc3cc(C)c(OC)c(OC)c3c(CO)n2)n1]

conditions

TABLE 1-continued

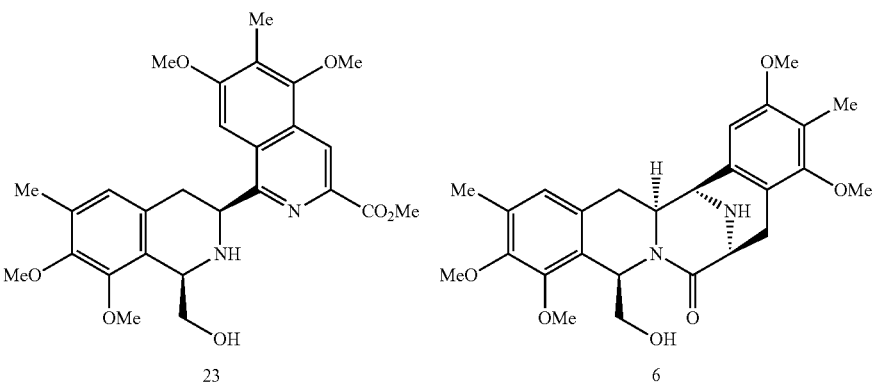 [SMILES: COC(=O)c1cc2c(OC)c(C)c(OC)cc2c([C@@H]2Cc3cc(C)c(OC)c(OC)c3[C@H](CO)N2)n1 ; COc1cc2c(c(OC)c1C)C[C@@H]1N[C@H]2[C@@H]2Cc3cc(C)c(OC)c(OC)c3[C@H](CO)N2C1=O]

| entry | catalyst | loading | ligand[d] | temperature | yield 23 | yield 6[a] | dr[b] | ee 6[c] |
|---|---|---|---|---|---|---|---|---|
| 1 | [Ir(cod)Cl]$_2$ | 5 mol % | 26 | 23° C. | 2% | 0% | ND | ND |
| 2 | [Ir(cod)Cl]$_2$ | 5 mol % | 24 | 60° C. | 22% | 0% | >20:1 | −82% |
| 3 | [Ir(cod)Cl]$_2$ | 5 mol % | 25 | 60° C. | 26% | 0% | >20:1 | −87% |
| 4 | [Ir(cod)Cl]$_2$ | 5 mol % | 26 | 60° C. | 30% | 0% | >20:1 | 80% |
| 5 | [Ir(cod)Cl]$_2$ | 5 mol % | 27 | 60° C. | 83% | 10% | >20:1 | 94% |
| 6 | [Ir(cod)Cl]$_2$ | 5 mol % | 27 | 80° C. | 31% | 43% | >20:1 | 87% |
| 7 | [Ir(cod)Cl]$_2$ | 5 mol % | 27 | 60° C.<br>80° C.[e] | 7% | 51%[f] | >20:1 | 94%[g] |
| 8 | [Ir(cod)Cl]$_2$ | 10 mol % | 27 | 60° C.<br>80° C.[e] | 3% | 63%[f] | >20:1 | 94%[g] |

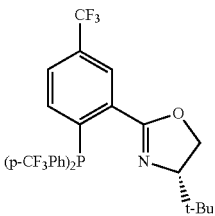

24: S—(CF$_3$)-t-BuPHOX

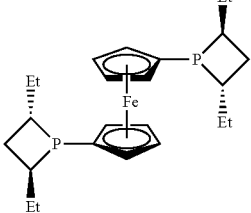

25: S,S—Et-FerroTANE

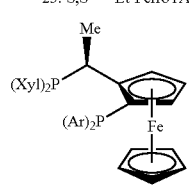

26: S,R$_p$-Xyliphos (Ar = Ph)
27: S,R$_p$—BTFM-Xyliphos
[Ar = 3,5-(CF$_3$)$_2$Ph]

TABLE 1-continued

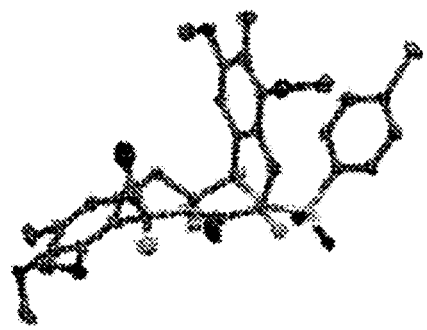

27: p-BrPhSO$_2$-6

Table 1 above reports the results of the development of the enantioselective hydrogenation. Unless otherwise noted, all reac-tions were run in 9:1 toluene:acetic acid (0.02 M) in the presence of tetra-n-butylammonium iodide (an iodide-to-iridium ratio of 3:1 was maintained in all cases) under a pressurized (60 bar) hydro-gen atmosphere for 18 hr. [a]Measured by absorption at 230 nm on UHPLC-MS vs. 1,2,4,5-tetrachlorobenzene internal standard unless otherwise noted. [b]Measured by $^1$H-NMR analysis of the crude reaction mixture. Measured for compound 23 for entries 1-4; measured for compound 6 for entries 5-8. [c]Measured on N-acetyl 23 after treating the crude reaction mixture with Ac2O and isolating the product via thin-layer chromatography. [d]A ligand-to-catalyst ratio of 1.2:1 was maintained in all cases. [e]Reaction performed at 60° C. for 18 hr, then the temperature was raised to 80° C. and maintained at that temperature for 24 hr. [f]Yield of isolated product. [g]Measured on compound 6 after its isolation. Dr is diastereomeric ratio (e.g., desired isomer vs. all other isomers); ee is enantiomeric excess; cod is 1,5-cyclooctadiene; TBAI is tetra-n-butylammonium iodide; ND is not determined; BTFM is bis-trifluoromethyl.

Upon beginning our enantioselective hydrogenation studies, we found that we could achieve trace amounts of mono-THIQ 23 by utilizing a catalyst mixture composed of [Ir(cod)Cl]2 (cod=1,5-cyclooctadiene), Xyliphos, and tetra-n-butylammonium iodide in a solvent mixture of 9:1 toluene:acetic acid (Table 1, Entry 1, 2% yield),[41] thus confirming the accelerating effects of hydroxyl direction. Utilizing these general conditions, we performed a very broad evaluation of more than 60 chiral ligands commonly used in enantioselective catalysis protocols.

From this survey, we initially identified three ligands that provided 23 in at least 80% enantiomeric excess (ee) and with uniformly excellent diastereoselectivity (all >20:1 dr): S—(CF$_3$)-t-BuPHOX (24, Entry 2, 22% yield, 82% ee), S,S-Et-FerroTANE (25, Entry 3, 26% yield, −87% ee), and S,R$_p$-Xyliphos (26, Entry 4, 30% yield, 80% ee). After evaluating each of these ligand classes further, we identified S,R$_p$-BTFM-Xyliphos (42) as a strongly activating ligand that provided mono-THIQ 23 in 83% yield, >20:1 dr, and in a remarkable 94% ee (Entry 5), thus confirming the stereochemical rationale presented above. Moreover, we were pleased to find that ligand 26 formed a catalyst that provided pentacycle 6 in 10% yield. Further evaluation of the reaction parameters revealed that increasing temperature provided higher levels of reactivity, albeit at the expense of enantioselectivity (Entry 6, 31% yield of 23, 43% yield of 6, >20:1 dr, 87% ee). Ultimately, the best results were achieved by performing the reaction at 60° C. for 18 hours followed by increasing the temperature to 80° C. for 24 hours.

Utilizing these conditions, 6 was isolated in 51% yield with >20:1 dr and 94% ee (Entry 7). In the end, doubling the catalyst loading allowed us to isolate 6 in 63% yield, also with >20:1 dr and 94% ee (Entry 8). Within the context of this synthesis, the relatively high catalyst loading (20 mol % Ir) is mitigated to a great extent by the substantial amount of complexity generated in this single trans-formation.

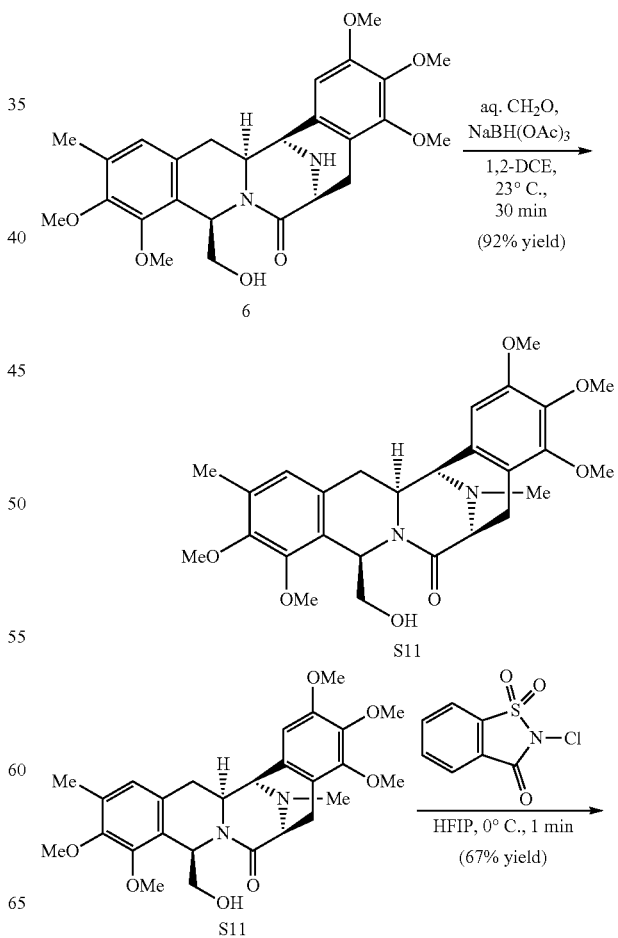

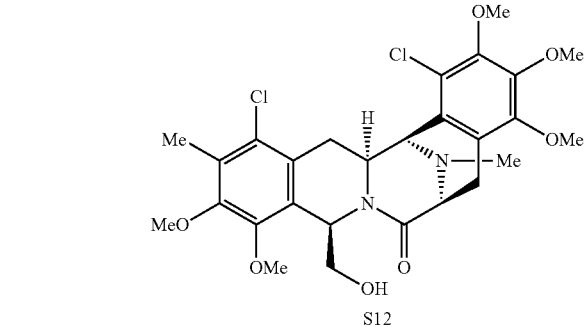

S12

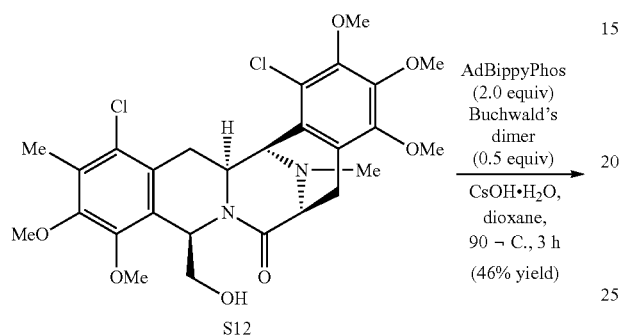

S12

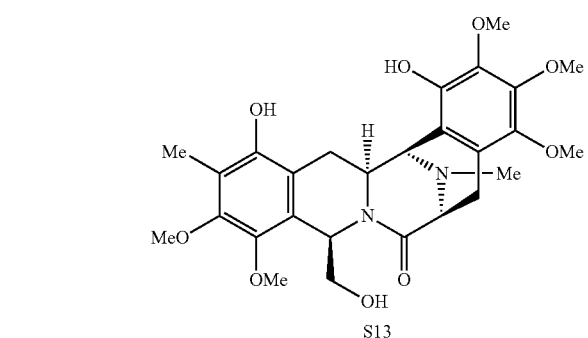

S13

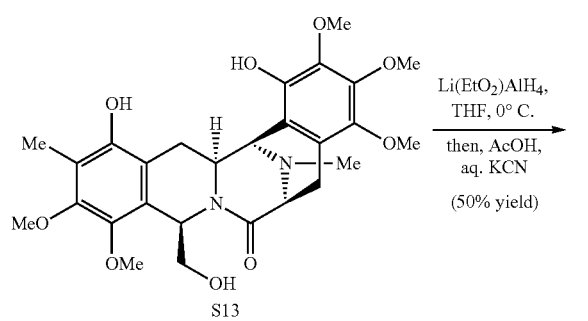

S13

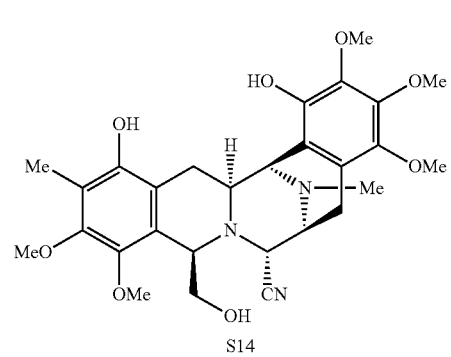

S14

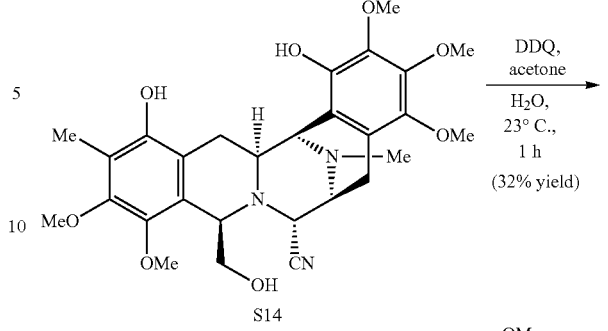

S14

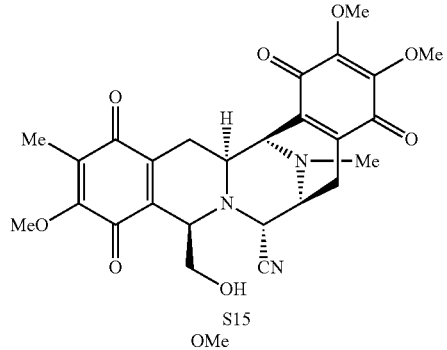

S15

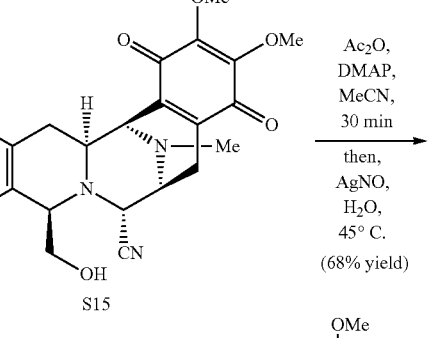

S15

1

The final steps of our total synthesis of jorumycin are shown above. Reductive methylation and dibromination of the ar-omatic termini proceeded smoothly in 89% and 88% yield, respectively. Lithiation of this species was achieved in THF at −78° C., and quenching this dianion with trimethylborate yielded an intermediate bis-boronic ester (not shown) which was not stable to isolation; however, oxidation of this species occurred upon the addition water and sodium perborate to the crude reaction mixture, directly providing bis-phenol 29. Exposure of 29 to lithium diethoxyaluminum hydride (43) cleanly reduced the lactam to the desired carbinolamine. Due to the known instability of this species,[16-19] the reaction was quenched with hydro-gen cyanide, affording the corresponding α-cyanoamine in 63% yield. Oxidation of the arenes proceeded in 69% yield (17)

to deliver bisquinone 30, a natural product known as Jorunnamycin A. Our synthesis was completed using a known two-step sequence for acylation and hydrolysis of the α-cyanoamine, providing (−)-jorumycin (1) in 53% yield.[16-19] In total, our synthesis requires 17 linear steps (21 total) in 0.7% overall yield.

In conclusion, we have developed a synthesis of (−)-jorumycin (1) that is orthogonal to existing bis-THIQ syntheses in that it is not reliant on highly electron-rich and π-nucleophilic aromatic rings. This will allow for the development of electron-deficient analogs that could be more metabolically stable than the natural products themselves. These analogs will have the potential to extend the still-largely untapped therapeutic potential of the bis-THIQ family of natural products.

EXAMPLES

General Information

Unless stated otherwise, reactions were performed at ambient temperature (23° C.) in flame-dried glassware under an argon atmosphere using dry, deoxygenated solvents (distilled or passed over a column of activated alumina). Commercially available reagents were used as received. Reactions requiring external heat were modulated to the specified temperatures using an IKAmag temperature controller. Thin-layer chromatography (TLC) was performed using E. Merck silica gel 60 F254 pre-coated plates (250 nm) and visualized by UV fluorescence quenching or potassium permanganate staining. Silicycle SiliaFlash P60 Academic Silica gel (particle size 40-63 nm) was used for flash chromatography. Purified water was obtained using a Barnstead NANOpure Infinity UV/UF system. $^1$H and $^{13}$C NMR spectra were recorded on a Varian Inova 500 (500 MHz and 126 MHz, respectively) and a Bruker AV III HD spectrometer equipped with a Prodigy liquid nitrogen temperature cryoprobe (400 MHz and 101 MHz, respectively) and are reported in terms of chemical shift relative to CHCl$_3$ (δ 7.26 and 77.16, respectively). $^{19}$F and $^{31}$P NMR spectra were recorded on a Varian Inova 300 (282 MHz and 121 MHz, respectively). Data for $^1$H NMR spectra are reported as follows: chemical shift (δ ppm) (multiplicity, coupling constant, integration). Infrared (IR) spectra were recorded on a Perkin Elmer Paragon 1000 Spectrometer and are reported in frequency of absorption (cm$^{-1}$). Analytical chiral SFC was performed with a Mettler SFC supercritical CO$_2$ analytical chromatography system with Chiralpak (AD-H) or Chiracel (OD-H) columns obtained from Daicel Chemical Industries, Ltd. High resolution mass spectra (HRMS) were obtained from the Caltech Center for Catalysis and Chemical Synthesis using an Agilent 6200 series TOF with an Agilent G1978A Multimode source in mixed (Multimode ESI/APCI) ionization mode. Optical rotations were measured on a Jasco P-2000 polarimeter using a 100 mm path-length cell at 589 nm.

Example 1: Synthesis of Isoquinoline-N-Oxide 9

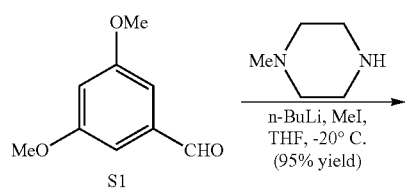

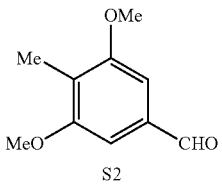

3,5-dimethoxy-4-methylbenzaldehyde (S2)

The procedure was adapted from the method of Comins et al.[i] N-methylpiperazine (670 μL, 6.6 mmol, 1.1 equiv) was dissolved in 20 mL THF and cooled to −20° C. n-Butyllithium (2.4 M, 2.65 mL, 6.3 mmol, 1.05 equiv) was added in a dropwise fashion, resulting in an orange solution. The solution was stirred at this temperature 15 min before a solution of 3,5-dimethoxybenzaldehyde (S1, 1.00 g, 6.0 mmol, 1 equiv) in 3 mL THF was added in a dropwise fashion, causing a color change to yellow. The solution was stirred at this temperature 30 min before a second portion of n-butyllithium (2.4 M, 7.5 mL, 18.1 mmol, 3 equiv) was added in a dropwise fashion. At this the flask was stored in a −20° C. freezer for 24 h. The flask was re-submerged in a −20° C. bath, and freshly distilled methyl iodide (2.25 mL, 36.1 mmol, 6 equiv) was added in a dropwise fashion, resulting in a mild exotherm. The solution was stirred 30 min at −20° C. and was removed from its bath, warming to room temperature. After 30 min the reaction was quenched by the addition of 20 mL 0.5 M HCl, and the solution was stirred 30 min without a cap. The layers were separated and the aqueous phase was saturated with sodium chloride. The aqueous phase was extracted with Et$_2$O, dried over MgSO$_4$ and concentrated. The product was purified by column chromatography (10% EtOAc/hex). Colorless solid, 1.03 g, 5.72 mmol, 95% yield. NMR spectra were identical to the previously reported compound.[2] $^1$H NMR (400 MHz, CDCl$_3$) δ 9.88 (s, 1H), 7.03 (s, 2H), 3.87 (s, 6H), 2.14 (s, 3H); $^{13}$C NMR (101 MHz, CDCl$_3$) δ 192.0, 158.7, 135.1, 122.5, 104.7, 55.9, 9.0.

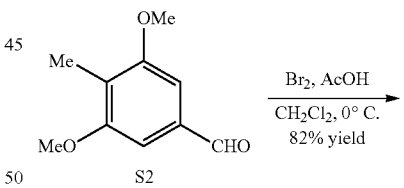

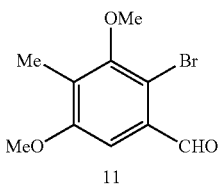

2-Bromo-3,5-dimethoxy-4-methylbenzaldehyde (11)

Aldehyde S1 (8.62 g, 47.8 mmol, 1 equiv) was dissolved in CH$_2$Cl$_2$ (100 mL, 0.5 M) and acetic acid (30 μL, 0.5 mmol, 0.01 equiv) was added. The solution was cooled to 0° C. before bromine was added in a slow, dropwise fashion. The solution was stirred 30 min after complete addition at 0° C., at which time TLC (10% EtOAc/hex) showed complete conversion. The reaction was quenched by the addition of 10% aqueous sodium thiosulfate and saturated NaHCO$_3$ solution. The layers were separated and the aqueous phase was extracted with CHCl$_3$. The combined organic phases were washed with water, dried over MgSO$_4$ and concentrated. The product was purified by dissolving in 50 mL boiling hexanes, under which conditions the trace amounts of dibromide are insoluble. The solution was filtered while boiling, providing the pure product. Colorless solid, 10.13 g, 39.1 mmol, 82% yield. NMR spectra were identical to the previously reported compound.[ii] $^1$H NMR (400 MHz, CDCl$_3$) δ 10.33 (s, 1H), 7.21 (s, 1H), 3.87 (s, 3H), 3.81 (s, 3H), 2.25 (s, 3H); $^{13}$C NMR (101 MHz, CDCl$_3$) δ 191.8, 158.2, 156.2, 132.2, 129.5, 114.9, 106.0, 60.8, 56.1, 10.6.

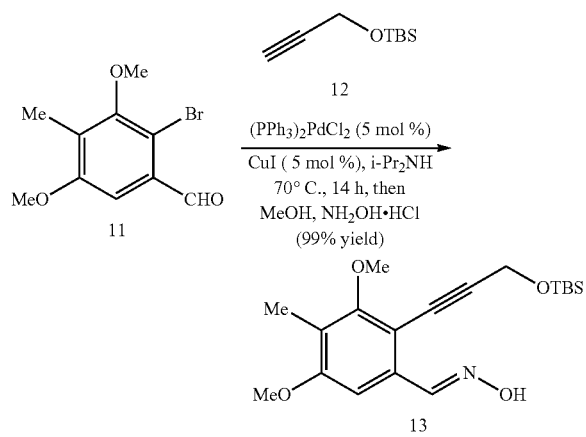

(E)-2-3-((tert-butyldimethylsilyl)oxy)prop-1-yn-1-yl)-3,6-dimethoxy-4-ethylbenzaldehyde oxime (13)

Bromide 11 (19.4 g, 74.9 mmol, 1 equiv), (PPh$_3$)$_2$PdCl$_2$ (2.6 g, 3.70 mmol, 0.05 equiv), and CuI (714 mg, 3.75 mmol, 0.05 equiv) were slurried in diisopropylamine (300 mL, 0.25 M, freshly distilled from CaH$_2$) in a 2 liter 3-necked roundbottom flask, and the orange suspension was sparged with N$_2$ for 10 min. O-tert-butyldimethylsilyl propargyl alcohol[iii] (12, 17.3 g, 101 mmol, 1.35 equiv) was added in one portion, causing the suspension to darken as the palladium catalyst was reduced. The suspension was sparged with N$_2$ for a further 1 min, then heated to 70° C. for 24 h. At this stage, TLC and LCMS indicated complete conversion of bromide 11, so the suspension was cooled to 50° C. and 200 mL MeOH was added. Hydroxylamine hydrochloride (6.24 g, 89.8 mmol, 1.2 equiv) was added in one portion and the solution was heated to reflux (85° C.) for 2 h. At this stage, TLC and LCMS indicated complete conversion to the product. The solution was cooled to room temperature and Celite (~100 g) was added. The suspension was filtered through a pad of celite, topped with sand, eluting with ethyl acetate. The filtrate was concentrated and purified by column chromatography (15% EtOAc/hex). Colorless solid, 26.9 g, 74.1 mmol, 99% yield. $^1$H NMR (500 MHz, CDCl$_3$) δ 8.60 (s, 1H), 7.46 (s, 1H), 7.10 (s, 1H), 4.62 (s, 2H), 3.86 (s, 6H), 2.15 (s, 3H), 0.95 (s, 9H), 0.18 (s, 6H); $^1$H NMR (500 MHz, CDCl$_3$) δ 160.5, 159.8, 149.5, 132.8, 122.5, 110.3, 101.9, 96.2, 78.2, 61.0, 55.9, 52.6, 26.0, 18.5, 9.3, −5.0; IR (thin film, NaCl): 3270.1, 3092.6, 2997.3, 1953.8, 2932.4, 2896.1, 2857.0, 2221.2, 1611.1, 1591.7, 1560.0, 1463.8, 1402.9, 1383.9, 1331.8, 1281.5, 1255.3, 1217.9, 1191.5, 1164.3, 1136.9, 1121.1, 1101.2, 1080.0, 1034.8, 977.1, 903.5, 837.9, 779.7, 722.1, 704.2, 671.8; HRMS (ESI-TOF) calc'd for [M$^+$] C$_{19}$H$_{29}$NO$_4$Si=363.1866, found 363.1939.

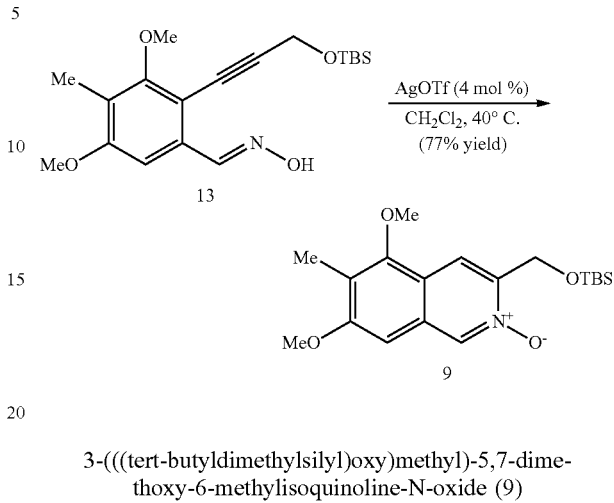

3-(((tert-butyldimethylsilyl)oxy)methyl)-5,7-dimethoxy-6-methylisoquinoline-N-oxide (9)

Oxime 13 (15.92 g, 45.7 mmol, 1 equiv) was dissolved in CH$_2$Cl$_2$ (460 mL, 0.1 M) and the flask was vacuum purged and refilled with nitrogen five times, then heated to reflux. AgOTf (235 mg, 0.91 mmol, 0.02 equiv) was added in one portion to the refluxing solution, resulting in a rapid and mildly exothermic reaction. The reaction flask was shielded from light and maintained at reflux for 15 min, at which time LCMS indicated full conversion to the product. The solution was filtered through a 1 inch pad of silica with 500 mL CH$_2$Cl$_2$ and 1 L 10% MeOH/EtOAc. Silica gel (40 mL) was added to the second portion of filtrate, which was then concentrated. The product was purified by column chromatography using a 6 inch pad of silica (30-50-100% EtOAc/CH$_2$Cl$_2$; then 2-5-10-20% MeOH/EtOAc+1% NEt$_3$). Colorless solid, 12.27 g, 33.8 mmol, 77% yield. The product is initially isolated as a black solid that is spectroscopically pure, and can be recrystallized to a colorless solid from minimal boiling heptanes. Very little mass is lost during this process (less than 50 mg from a 12 g batch), indicating the presence of very minor yet highly colored impurities. $^1$H NMR (400 MHz, CDCl$_3$) δ 8.65 (s, 1H), 8.02 (s, 1H), 6.71 (s, 1H), 5.01 (d, J=1.4 Hz, 2H), 3.92 (s, 3H), 3.87 (s, 3H), 2.27 (s, 3H), 1.00 (s, 9H), 0.15 (s, 6H); $^{13}$C NMR (101 MHz, CDCl$_3$) δ 159.4, 153.7, 145.9, 135.2, 128.4, 123.6, 120.1, 115.0, 97.4, 61.7, 60.1, 55.9, 26.0, 18.4, 9.8, −5.3; IR (thin film, NaCl): 3390.3, 3073.7, 2998.1, 2953.8, 2892.2, 2857.2, 1637.3, 1613.4, 1567.8, 1470.6, 1390.6, 1371.6, 1341.4, 1308.3, 1254.2, 1209.7, 1185.3, 1148.0, 1116.4, 1020.7, 1007.1, 957.4, 899.7, 838.8, 808.0, 777.9, 701.7, 669.8, 637.7; HRMS (ESI-TOF) calc'd for [M$^+$] C$_{19}$H$_{29}$NO$_4$Si=363.1866, found 363.1863.

Example 2: Synthesis of Isoquinoline Triflate 10

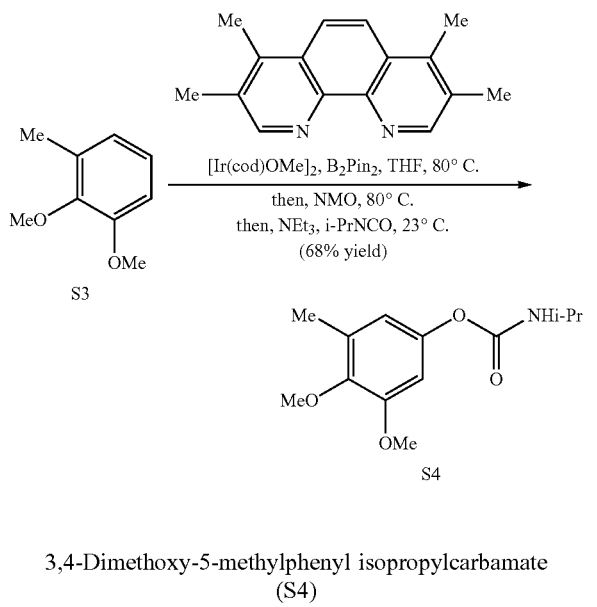

3,4-Dimethoxy-5-methylphenyl isopropylcarbamate (S4)

In a nitrogen-filled glovebox, [Ir(cod)OMe]$_2$ (22.3 mg, 0.034 mmol, 0.005 equiv) and 3,4,7,8-tetramethyl-1,10-phenanthroline (15.9 mg, 0.067 mmol, 0.01 equiv) were dissolved in 5 mL THF and stirred 30 min. In the meantime, 2,3-dimethoxytoluene (1.00 mL, 6.73 mmol, 1 equiv) and B$_2$Pin$_2$ (1.28 g, 5.05 mmol, 0.75 equiv) were weighed into a 20 mL sealable microwave vial (also in the glovebox) with a teflon-coated stir bar and 5 mL THF was added. Upon complete dissolution, the catalyst solution was transferred to the microwave vial, which was sealed prior to removing from the glovebox. The vial was then placed in a preheated 80° C. oil bath and stirred 48 h, at which time TLC (20% EtOAc/hex) revealed complete conversion to a single borylated product. The vial was cooled to room temperature and the cap was removed. N-methylmorpholine-N-oxide (2.37 g, 20.2 mmol, 3 equiv) was added in a few small portions and the vial was resealed and returned to the 80° C. oil bath for 3 h, at which time TLC (20% EtOAc/hex) indicated complete oxidation to the intermediate phenol. Triethylamine (4.7 mL, 33.7 mmol, 5 equiv) and isopropyl isocyanate (2.6 mL, 26.9 mmol, 4 equiv) were added at 23° C. and the solution was stirred 16 h, at which time TLC (50% EtOAc/hex) indicated complete conversion to carbamate S4. The contents of the vial were transferred to a 100 mL roundbottom flask and 10% aq. Na$_2$S$_2$O$_3$ was added to quench the remaining oxidant and citric acid hydrate (4.5 g, >3 equiv) was added to chelate the boron. This solution was stirred 1 h, and concentrated HCl was added 1 mL at a time until an acidic pH was achieved. The layers were separated and the aqueous phase was extracted with EtOAc. The combined organic phases were then washed with aqueous K$_2$CO$_3$, dried over MgSO$_4$ and concentrated. The product was purified by column chromatography (25% EtOAc/hex). Colorless solid, 1.16 g, 4.6 mmol, 68% yield. NMR spectra were identical to the previously reported compound.[iv] $^1$H NMR (400 MHz, CDCl$_3$) δ 6.55 (d, J=2.6 Hz, 1H), 6.52 (d, J=2.8 Hz, 1H), 4.84 (d, J=7.8 Hz, 1H), 3.88 (ddd, J=16.1, 13.9, 7.6 Hz, 1H), 3.82 (s, 3H) 3.76 (s, 3H), 2.24 (s, 3H), 1.23 (s, 3H), 1.21 (s, 3H); $^{13}$CH NMR (101 MHz, CDCl$_3$) δ 154.0, 153.0, 146.8, 144.7, 132.3, 115.4, 104.3, 60.3, 55.9, 43.6, 23.0, 16.0.

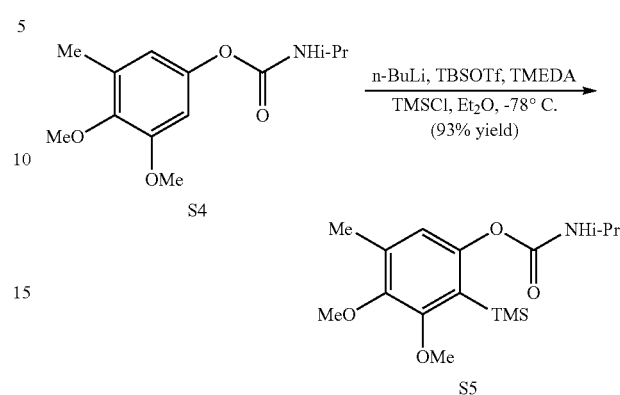

3,4-Dimethoxy-5-methyl-2-(trimethylsilyl)phenyl isopropylcarbamate (S5)

Vigorous stirring was required throughout the course of the reaction due to the formation of insoluble triflate salts. Carbamate S4 (17.30 g, 68.2 mmol, 1 equiv) was dissolved in Et$_2$O (340 mL, 0.2 M) N,N,N',N'-tetramethylethylenediamine (TMEDA, 11.3 mL, 75.1 mmol, 1.1 equiv) was added and the solution was cooled to 0° C. before tert-butyldimethylsilyl triflate (TBSOTf, 17.25 mL, 75.1 mmol, 1.1 equiv) was added in a slow stream. The solution was stirred 10 min at 0° C., removed from the ice bath and stirred at 23° C. for 30 min. A second portion of TMEDA (41 mL, 273 mmol, 4 equiv) was added and the solution was cooled to −78° C. n-Butyllithium (2.4 M, 114 mL, 274 mmol, 4 equiv) was added in a dropwise fashion through a flame-dried addition funnel over the course of 1 h, being sure to not let the temperature rise significantly. The resulting yellow suspension was stirred vigorously for 4 h at −78° C., taking care not to let the temperature rise. Trimethylsilyl chloride (61 mL, 478 mmol, 7 equiv) was then added dropwise via the addition funnel over the course of 30 min and the suspension was stirred at −78° C. for 30 min, then was removed from the dry ice bath and stirred at 23° C. for 16 h. The reaction was quenched by the addition of 300 mL aqueous NH$_4$Cl (30 mL saturated solution diluted to 300 mL) through an addition funnel, the first 50 mL of which were added dropwise, followed by the addition of the remainder in a slow stream. The aqueous phase was then further acidified by the addition of small portions of concentrated HCl until an acidic pH was achieved (~30 mL required). The layers were separated and the aqueous phase was extracted twice with Et$_2$O. The combined organic phases were washed with saturated aqueous NH$_4$Cl, dried over MgSO$_4$ and concentrated. The product was purified by column chromatography (20-30% Et$_2$O/hex). Colorless solid, 20.61 g, 63.3 mmol, 93% yield. NMR spectra were identical to the previously reported compound.[5] $^1$H NMR (300 MHz, CDCl$_3$) δ 6.63 (s, 1H), 4.69 (d, J=8.1 Hz, 1H), 3.96-3.85 (m, 1H), 3.83 (s, 3H), 3.76 (s, 3H), 2.23 (s, 3H), 1.23 (s, 3H), 1.21 (s, 3H), 0.28 (s, 9H); 157.9, $^{13}$C NMR (126 MHz, CDCl$_3$) δ 157.9, 154.2, 150.5, 148.5, 134.6, 123.0, 120.1, 60.5, 59.8, 43.5, 23.1, 16.1, 1.3.

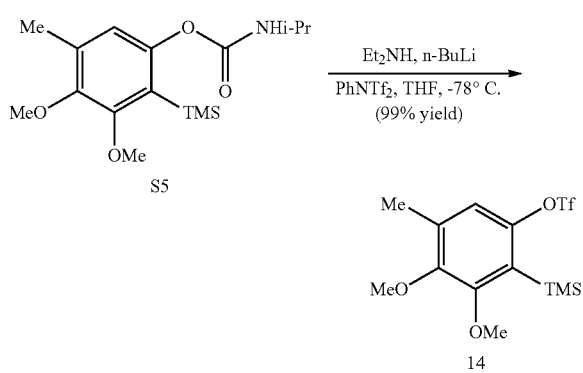

3,4-Dimethoxy-5-methyl-2-(trimethylsilyl)phenyl trifluoromethanesulfonate (14)

Carbamate S5 (8.08 g, 24.8 mmol, 1 equiv) was dissolved in THF (100 mL, 0.25 M) and diethylamine (3.85 mL, 37.2 mmol, 1.5 equiv) was added and the solution was cooled to −78° C. n-Butyllithium (2.5 M, 15 mL, 37.5 mmol, 1.5 equiv) was added slowly over the course of 15 min. The solution was stirred at that temperature for 30 min, then removed from its bath and stirred at 23° C. for 30 min. N-Phenyl triflimide (10.6 g, 29.8 mmol, 1.2 equiv) was added in one portion and the solution was stirred 30 min. A second portion of diethylamine (4.6 mL, 44.7 mmol, 1.8 equiv) was added and the solution was stirred 2 h. The solution was filtered through a 1 inch pad of silica gel with 50% Et$_2$O/hex and concentrated. The product was purified by column chromatography (10% Et$_2$O/hex). Arene 14 can be isolated as a colorless oil, but undergoes decomposition and should be used within the day of its isolation. Colorless oil, 9.15 g, 24.6 mmol, 99% yield. NMR spectra were identical to the previously reported compound.[5] $^1$H NMR (400 MHz, CDCl$_3$) δ 6.87 (s, 1H), 3.86 (s, 3H), 3.77 (s, 3H), 2.27 (d, J=0.7 Hz, 3H), 0.36 (s, 9H); $^{13}$C NMR (101 MHz, CDCl$_3$) δ 158.5, 150.4, 149.0, 135.6, 124.2, 118.7 (q, J=320.6 Hz), 117.7, 60.6, 59.8, 16.3, 1.2; $^{19}$F NMR (282 MHz, CDCl$_3$) δ −73.1 (s, 3F).

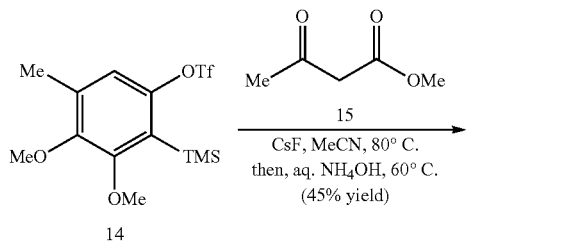

7,8-Dimethoxy-1,6-dimethyl-3-hydroxyisoquinoline (16)

Cesium fluoride (204 mg, 1.34 mmol, 2.5 equiv) was dissolved in acetonitrile (5.4 mL, 0.1 M) in a 20 mL microwave vial and water (9.7 μL, 0.537 mmol, 1.0 equiv) and methyl acetoacetate (58 μL, 0.537 mmol, 1.0 equiv) were added. Aryne precursor 14 (250 mg, 0.671 mmol, 1.25 equiv) was added neat via syringe, and the vial was placed in a preheated 80° C. oil bath. After 2 h, TLC revealed complete consumption of 14, so NH$_4$OH (28-30%, 5.4 mL) was added in one portion. The vial was moved to a preheated 60° C. oil bath and stirred 8 h. The solution was poured into brine inside a separatory funnel and the solution was extracted with EtOAc (2×30 mL). The aqueous phase was brought to pH 7 by the addition of concentrated HCl and was extracted with EtOAc (2×30 mL). The aqueous phase was discarded. The organic phase was then extracted with 2M HCl (5×20 mL). The organic phase was checked by LCMS to confirm that all of product 16 had transferred to the aqueous phase and was subsequently discarded. The aqueous phase was then brought back to pH 7 by the addition of 100 mL 2M NaOH and was extracted with EtOAc (5×20 mL). The combined organic phases were washed with brine, dried over Na$_2$SO$_4$ and concentrated, providing the product. Yellow solid, 56.9 mg, 0.243 mmol, 45% yield. $^1$H NMR (300 MHz, CDCl$_3$) δ 6.95 (d, J=0.7 Hz, 1H), 6.53 (s, 1H), 3.93 (s, 3H), 3.84 (s, 3H), 3.05 (d, J=0.7 Hz, 3H), 2.31 (d, J=1.0 Hz, 3H); $^{13}$C NMR (126 MHz, CDCl$_3$) δ 161.7, 149.4, 145.8, 142.5, 140.3, 121.3, 113.0, 104.7, 60.4, 60.1, 21.0, 17.2; IR (thin film, NaCl): 3327.0, 2937.6, 2608.7, 1651.7, 1455.4, 1324.2, 1226.8, 1177.9, 1147.2, 1089.5, 1062.3, 1034.8, 1000.5, 960.0, 937.7, 892.4, 861.7, 813.2, 724.1, 682.8, 662.3; HRMS (ESI-TOF) calc'd for [M$^+$] C$_{13}$H$_{15}$NO$_3$=233.1052, found 233.1057.

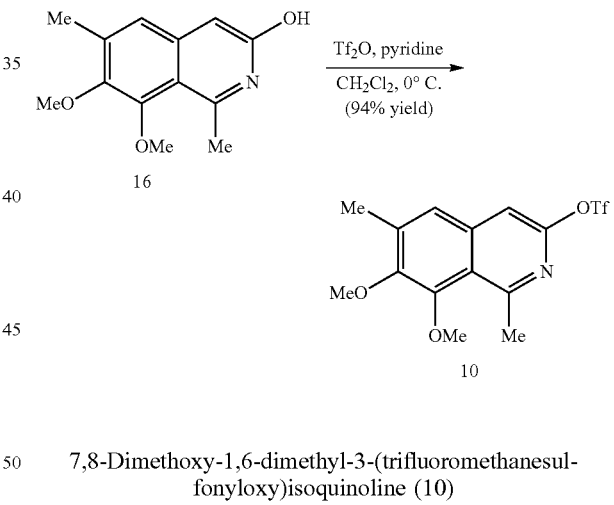

7,8-Dimethoxy-1,6-dimethyl-3-(trifluoromethanesulfonyloxy)isoquinoline (10)

Hydroxyisoquinoline 16 (2.60 g, 11.1 mmol, 1 equiv) was dissolved in CH$_2$Cl$_2$ (70 mL, 0.16 M) and pyridine (11.4 mL, 140.6 mmol, 12.7 equiv) was added and the solution was cooled to 0° C. Trifluoromethanesulfonic anhydride (Tf$_2$O, 3.00 mL, 17.8 mmol, 1.6 equiv) was added dropwise, causing the yellow solution to turn dark red. After 30 min TLC (10% EtOAc/hex) revealed complete conversion, so the reaction was quenched by the addition of saturated aqueous NaHCO$_3$ (70 mL). The solution was stirred vigorously until bubbling ceased, at which time the layers were separated. The organic phase was extracted with CH$_2$Cl$_2$ and the combined organic phases were dried over Na$_2$SO$_4$ and concentrated. The product was purified by column chromatography (10% Et$_2$O/hex). Yellow oil, 3.82 g, 10.5 mmol, 94% yield. $^1$H NMR (400 MHz, CDCl$_3$) δ 7.39 (d, J=1.0 Hz, 1H), 7.21 (s, 1H), 3.98 (s, 3H), 3.93 (s, 3H), 3.07 (d, J=0.7 Hz, 3H), 2.44 (d, J=1.0 Hz, 3H); $^{13}$C NMR (101 MHz, CDCl$_3$) δ 158.6, 151.0, 150.5, 149.9, 139.2, 136.8, 123.6, 122.9, 118.8 (q, J=320.5 Hz), 107.6, 60.8, 60.2, 26.7, 17.0; $^{19}$F NMR (282 MHz, CDCl$_3$) δ −72.99; IR (thin film, NaCl): 3436.0, 2939.4, 1605.5, 1553.6, 1493.7, 1415.9, 1381.0, 1351.9, 1332.9, 1248.8, 1209.3, 1133.6, 1097.0, 1059.9, 1009.8, 983.4, 966.2, 940.7, 892.0, 834.7, 768.1, 695.0, 649.3, 608.2; HRMS (ESI-TOF) calc'd for [M$^+$] C$_{14}$H$_{14}$F$_3$NO$_5$S=365.0545, found 365.0547.

Example 3: Fagnou Cross-Coupling Reaction

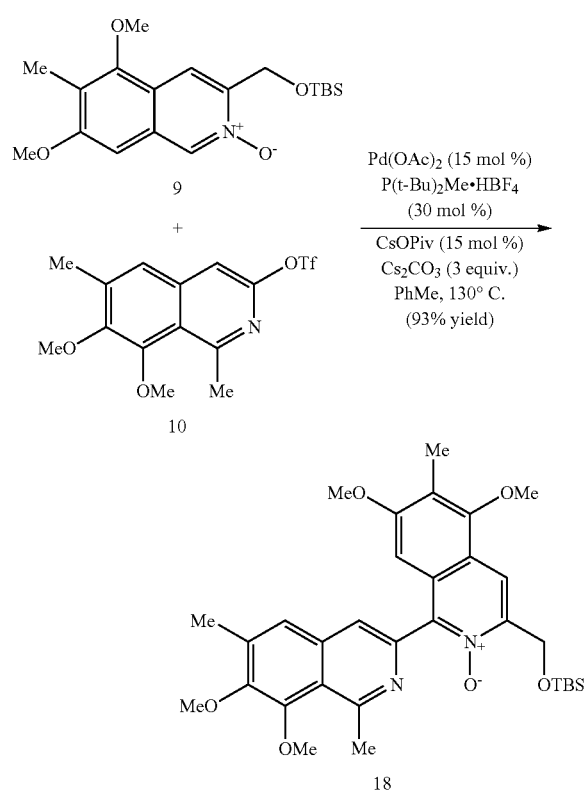

3-(((tert-butyldimethylsilyl)oxy)methyl)-5,7,7',8'-tetramethoxy-1',6,6'-trimethyl-[1,3'-biisoquinoline] 2-oxide (18)

Palladium acetate (347 mg, 1.54 mmol, 0.20 equiv), di-tert-butyl(methyl)phosphonium tetrafluoroborate (957 mg, 3.86 mmol, 0.50 equiv), and cesium carbonate (1.26 g, 3.41 mmol, 0.50 equiv) were weighed into a 100 mL pear-shaped flask and brought into a nitrogen-filled glovebox and cesium pivalate (CsOPiv, 722 mg, 3.09 mmol, 0.40 equiv) was added to the flask. In the glovebox, degassed toluene (80 mL) was added, the flask was sealed with a rubber septum and removed from the glovebox, to be placed in a 60° C. preheated oil bath, where it was stirred for 30 min and allowed to cool to room temperature. In the meantime, N-oxide 9 (8.42 g, 23.1 mmol, 3 equiv) and cesium carbonate (7.54 g, 23.1 mmol, 3 equiv) were weighed into a 250 mL sealable flask equipped with a Kontes valve, to which 50 mL toluene was added, and this suspension was sparge-degassed with nitrogen for 10 min. Isoquinoline triflate 10 (2.77 g, 6.82 mmol, 1.00 equiv) was dissolved in 10 mL toluene, which was sparge-degassed with nitrogen for 10 min. The solution of isoquinoline triflate 10 was then added via cannula to the cooled catalyst solution, rinsing the flask with 5 mL degassed toluene. The catalyst/triflate solution was then added via cannula to the 250 mL sealable flask, rinsing with 10 mL degassed toluene. The flask was sealed and placed in a 130° C. preheated oil bath for 4.5 h. The flask was then allowed to cool to room temperature and Celite (10 g) was added. This suspension was then filtered through a 1 inch pad of Celite that was topped with sand, rinsing with CH$_2$Cl$_2$ and acetone (500 mL each). The solution was concentrated, providing the crude product. $^1$H NMR of the crude reaction mixture showed a 2:1 mixture of bis-isoquinoline 18 and N-oxide 9 at this point, indicating complete conversion to product. The product was purified by column chromatography (10-20% EtOAc/hex, then 20-50-100% EtOAc/hex+1% NEt$_3$, then 10-20% MeOH/EtOAc+1% NEt$_3$. bis-Isoquinoline 18 elutes during the 50-100% EtOAc/hex portion, and remaining N-oxide 9 elutes during the 10-20% MeOH/EtOAc portion). Colorless foam, 3.88 g, 6.70 mmol, 98% yield. An analogous coupling performed with 2.39 g isoquinoline triflate 10 provided 3.30 g of product (87% yield), together providing 7.18 g bis-isoquinoline 18 in 93% average yield. $^1$H NMR (400 MHz, CDCl$_3$) δ 8.13 (d, J=0.9 Hz, 1H), 7.81 (s, 1H), 7.42 (d, J=1.1 Hz, 1H), 6.60 (s, 1H), 5.06 (d, J=1.4 Hz, 2H), 4.01 (s, 3H), 3.97 (s, 3H), 3.90 (s, 3H), 3.65 (s, 3H), 3.17 (s, 3H), 2.45 (d, J=0.9 Hz, 3H), 2.28 (s, 3H), 1.03 (s, 9H), 0.17 (s, 6H); $^{13}$C NMR (101 MHz, CDCl$_3$) δ 158.9, 157.8, 153.8, 151.3, 149.6, 146.0, 143.7, 142.0, 137.6, 134.8, 128.2, 124.3, 122.7, 122.5, 121.5, 120.4, 114.5, 98.6, 61.8, 60.9, 60.4, 60.3, 27.2, 25.7, 18.5, 17.1, 9.7, −5.2; IR (thin film, NaCl): 3417.9, 2954.4, 2856.9, 1614.6, 1567.0, 1463.4, 1392.7, 1328.6, 1255.0, 1213.2, 1189.5, 1139.2, 1117.7, 1089.2, 1057.0, 1008.0, 961.2, 936.5, 897.0, 839.1, 815.5, 778.4, 734.4, 701.8, 634.2; HRMS (ESI-TOF) calc'd for [M$^+$] C$_{32}$H$_{42}$N$_2$O$_6$Si=578.2812, found 578.2796.

Example 4: First-Generation Synthesis of Bis-Isoquinoline 22

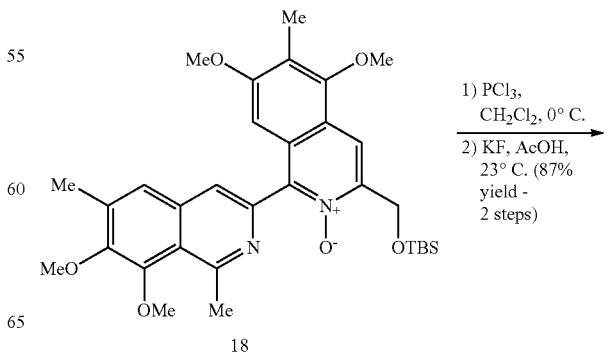

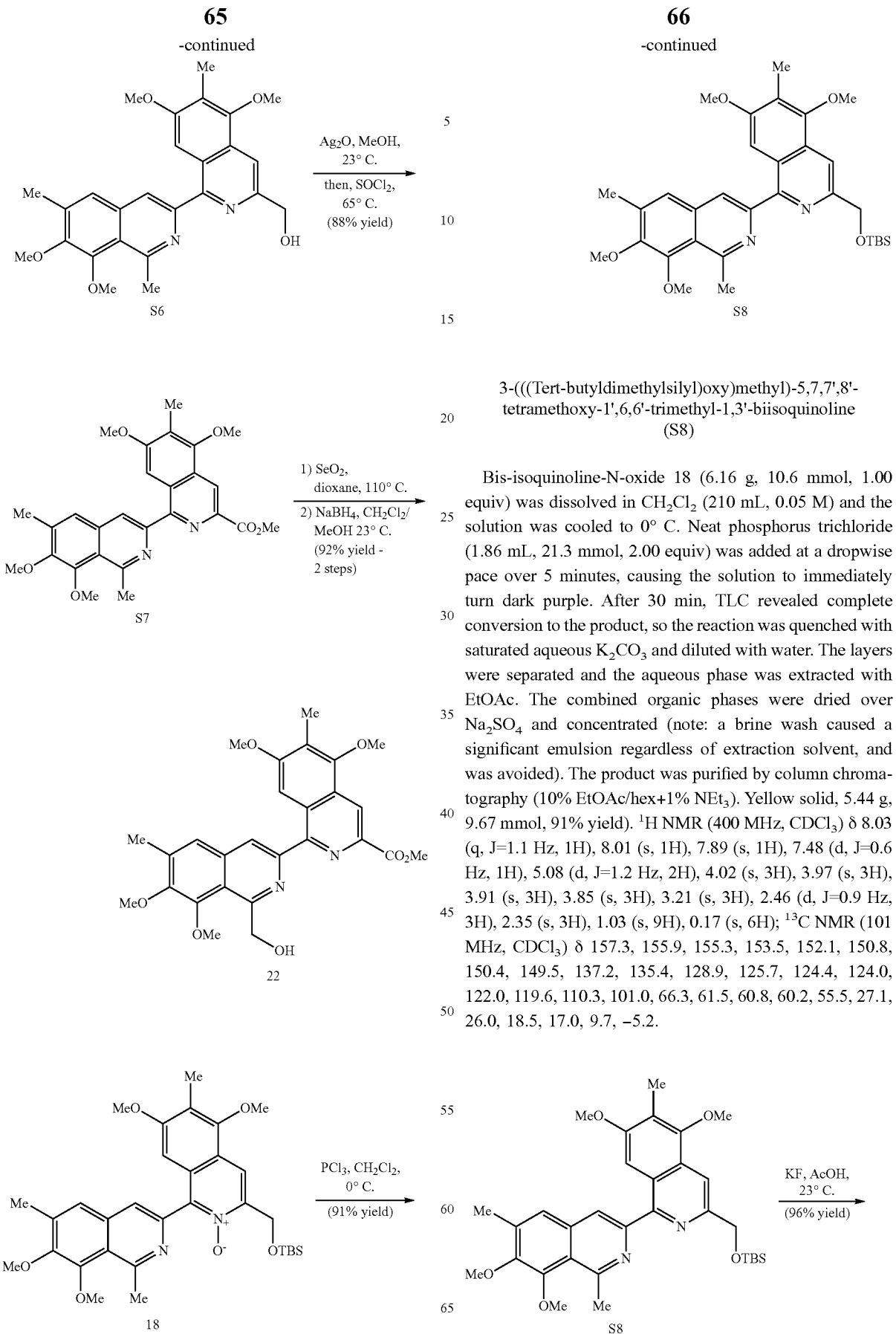

3-(((Tert-butyldimethylsilyl)oxy)methyl)-5,7,7',8'-tetramethoxy-1',6,6'-trimethyl-1,3'-biisoquinoline (S8)

Bis-isoquinoline-N-oxide 18 (6.16 g, 10.6 mmol, 1.00 equiv) was dissolved in $CH_2Cl_2$ (210 mL, 0.05 M) and the solution was cooled to 0° C. Neat phosphorus trichloride (1.86 mL, 21.3 mmol, 2.00 equiv) was added at a dropwise pace over 5 minutes, causing the solution to immediately turn dark purple. After 30 min, TLC revealed complete conversion to the product, so the reaction was quenched with saturated aqueous $K_2CO_3$ and diluted with water. The layers were separated and the aqueous phase was extracted with EtOAc. The combined organic phases were dried over $Na_2SO_4$ and concentrated (note: a brine wash caused a significant emulsion regardless of extraction solvent, and was avoided). The product was purified by column chromatography (10% EtOAc/hex+1% $NEt_3$). Yellow solid, 5.44 g, 9.67 mmol, 91% yield). $^1$H NMR (400 MHz, $CDCl_3$) δ 8.03 (q, J=1.1 Hz, 1H), 8.01 (s, 1H), 7.89 (s, 1H), 7.48 (d, J=0.6 Hz, 1H), 5.08 (d, J=1.2 Hz, 2H), 4.02 (s, 3H), 3.97 (s, 3H), 3.91 (s, 3H), 3.85 (s, 3H), 3.21 (s, 3H), 2.46 (d, J=0.9 Hz, 3H), 2.35 (s, 3H), 1.03 (s, 9H), 0.17 (s, 6H); $^{13}$C NMR (101 MHz, $CDCl_3$) δ 157.3, 155.9, 155.3, 153.5, 152.1, 150.8, 150.4, 149.5, 137.2, 135.4, 128.9, 125.7, 124.4, 124.0, 122.0, 119.6, 110.3, 101.0, 66.3, 61.5, 60.8, 60.2, 55.5, 27.1, 26.0, 18.5, 17.0, 9.7, −5.2.

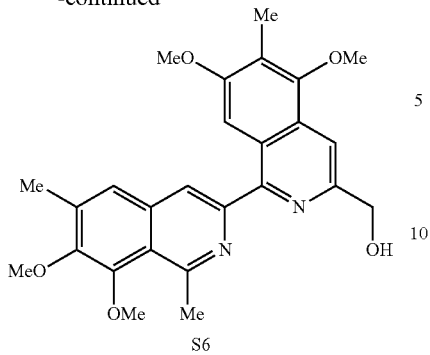

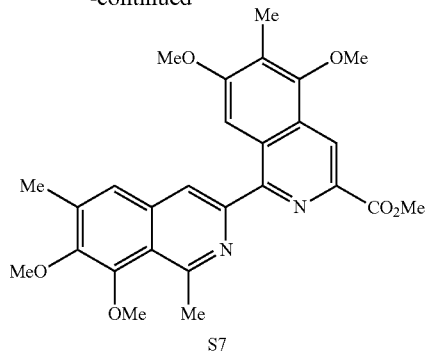

(5,7,7',8'-Tetramethoxy-1',6,6'-trimethyl-[1,3'-biisoquinolin]-3-yl)methanol (S6)

Bis-isoquinoline S8 (5.44 g, 9.7 mmol, 1.00 equiv) was dissolved in acetic acid (40 mL, 0.25 M) and solid potassium fluoride (2.81 g, 48.0 mmol, 5.00 equiv) was added in one portion. The solution was stirred 30 min at room temperature, at which time LCMS showed complete conversion to the product. The solution was diluted with $CH_2Cl_2$ and ice and the solution was stirred vigorously as a solution of sodium hydroxide (25 g, 0.625 mol, 0.9 equiv relative to 40 mL AcOH) in 70 mL water was added slowly. The rest of the acetic acid was quenched by the addition of saturated aqueous $K_2CO_3$. The layers were separated and the aqueous phase was extracted with $CH_2Cl_2$. The combined organic phases were washed with brine, dried over $Na_2SO_4$ and concentrated. The product was purified by column chromatography (1-2-3-4-5% MeOH/$CH_2Cl_2$+1% $NEt_3$). Colorless solid, 4.17 g, 9.31 mmol, 96% yield. $^1$H NMR (400 MHz, $CDCl_3$) δ 8.09 (s, 1H), 8.03 (s, 1H), 7.79 (d, J=0.9 Hz, 1H), 7.49 (d, J=1.1 Hz, 1H), 4.94 (s, 2H), 4.03 (s, 3H), 3.97 (s, 3H), 3.89 (s, 3H), 3.87 (s, 3H), 3.22 (s, 3H), 2.47 (d, J=1.0 Hz, 3H), 2.35 (s, 4H); $^{13}$C NMR (101 MHz, $CDCl_3$) δ 157.8, 156.0, 155.2, 153.5, 151.1, 150.3, 149.7, 149.6, 137.6, 135.4, 129.0, 126.2, 124.7, 124.6, 122.2, 119.9, 111.3, 101.3, 65.0, 61.7, 60.9, 60.3, 55.6, 27.2, 17.1, 9.9; IR (thin film, NaCl): 3352.3, 3128.9, 2936.6, 2855.0, 1620.4, 1594.1, 1556.8, 1484.4, 1462.2, 1454.9, 1416.4, 1392.3, 1355.0, 1331.4, 1303.1, 1243.0, 1218.0, 1195.9, 1133.0, 1117.1, 1090.7, 1059.8, 1008.2, 963.5, 906.0, 884.5, 841.2, 795.7, 732.6, 645.8; HRMS (ESI-TOF) calc'd for [M+] $C_{26}H_{28}N_2O_5$=448.1998, found 448.1992.

Methyl 5,7,7',8'-tetramethoxy-1',6,6'-trimethyl-[1,3'-biisoquinoline]-3-carboxylate (S7)

bis-Isoquinoline S6 (1.50 g, 3.34 mmol, 1.00 equiv) and silver(I) oxide (3.88 g, 16.7 mmol, 5.00 equiv) were slurried in MeOH (35 mL, 0.1 M). After 30 min, the solution appeared to be fully homogeneous and deep red in color. After 4 h, LCMS showed full conversion to a mixture of methyl ester S7 and the corresponding carboxylic acid. Thionyl chloride (1.21 mL, 16.7 mmol, 5.00 equiv) was added through the top of a reflux condenser, and following the complete addition the solution was heated to reflux After 1.5 LCMS showed complete conversion to methyl ester S7. The solution was cooled to room temperature and celite was added, and the solution was filtered through more celite, rinsing with EtOAc. The solution was concentrated, then redissolved in $CH_2Cl_2$ and was washed with dilute aqueous $K_2CO_3$ and brine. The layers were separated and the aqueous phase was extracted with $CH_2Cl_2$. The combined organic phases were washed with brine, dried over $Na_2SO_4$ and concentrated. The product was purified by column chromatography (25% EtOAc/hex+1% $NEt_3$). White solid, 1.40 g, 2.94 mmol, 88% yield. $^1$H NMR (400 MHz, $CDCl_3$) δ 8.75 (d, J=0.9 Hz, 1H), 8.19 (s, 1H), 8.13 (s, 1H), 7.52 (d, J=1.1 Hz, 1H), 4.05 (s, 3H), 4.01 (s, 3H), 3.97 (s, 3H), 3.94 (s, 3H), 3.90 (s, 3H), 3.20 (s, 3H), 2.46 (d, J=1.0 Hz, 3H), 2.36 (s, 3H); $^1$H NMR (400 MHz, $CDCl_3$) δ 167.0, 160.0, 156.0, 155.8, 154.9, 151.1, 149.9, 149.5, 139.0, 137.5, 135.6, 128.6, 128.0, 125.0, 124.7, 122.3, 120.5, 118.6, 101.9, 62.3, 60.9, 60.3, 55.8, 52.8, 27.1, 17.1, 9.9; IR (thin film, NaCl): 3443.0, 2948.7, 1714.1, 1614.7, 1454.4, 1407.2, 1384.3, 1330.3, 1304.7, 1270.1, 1226.4, 1136.9, 1088.6, 1057.2, 1008.0, 870.5, 786.0, 733.2; HRMS (ESI-TOF) calc'd for [M$^+$] $C_{27}H_{28}N_2O_6$=476.1947, found 476.1952.

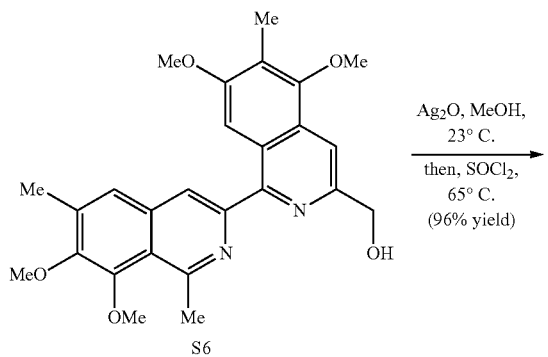

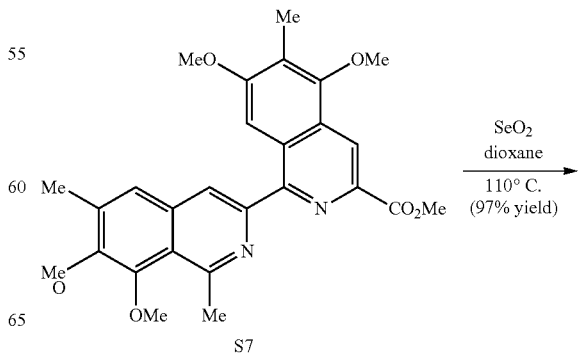

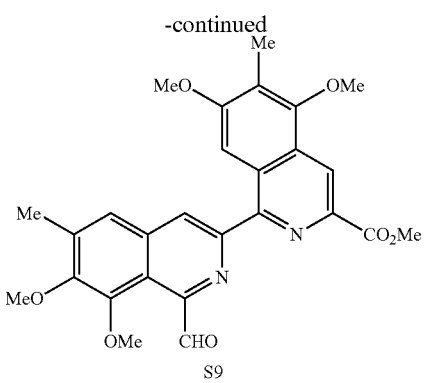

S9

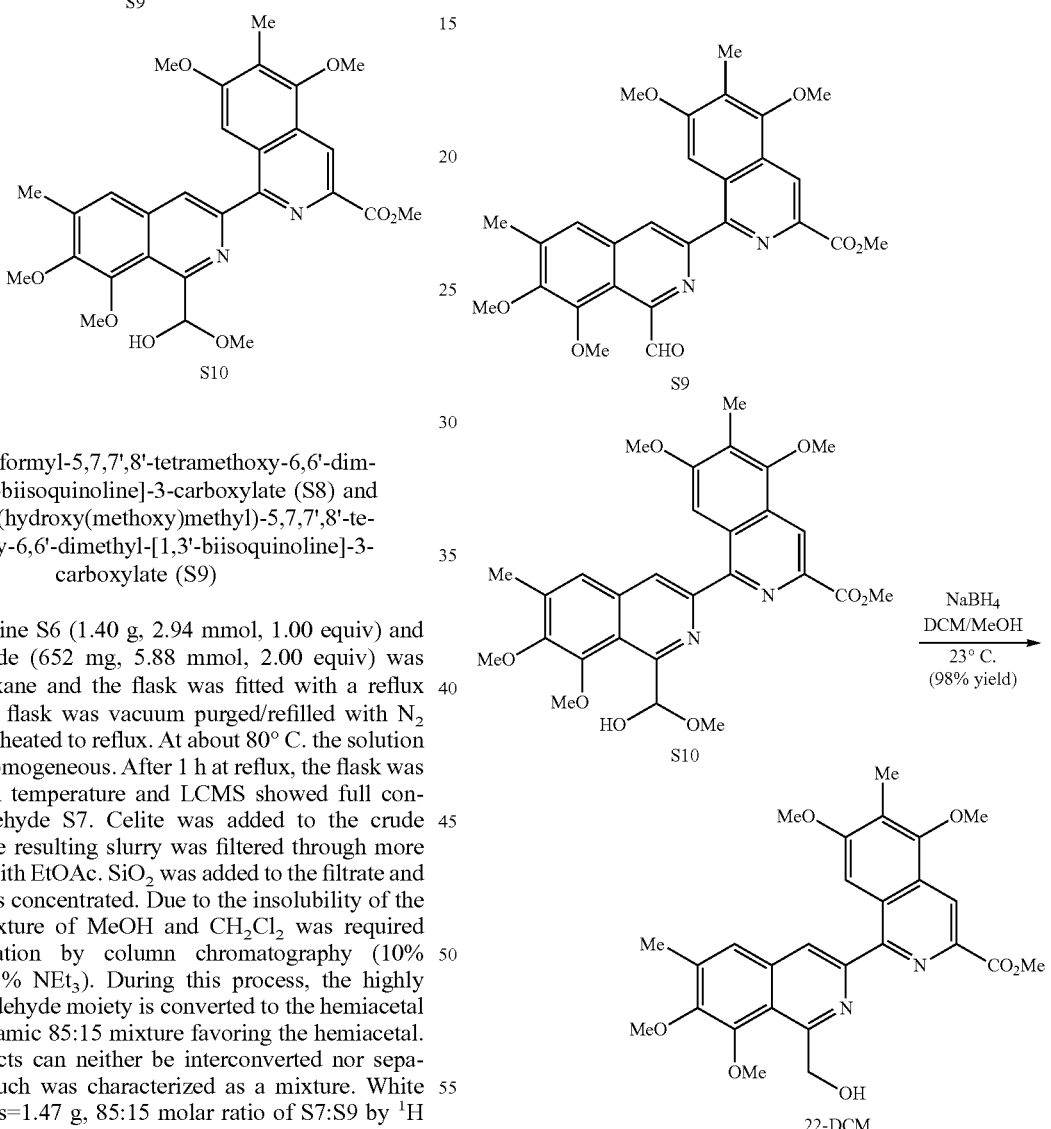

Methyl 1'-formyl-5,7,7',8'-tetramethoxy-6,6'-dimethyl-[1,3'-biisoquinoline]-3-carboxylate (S8) and methyl 1'-(hydroxy(methoxy)methyl)-5,7,7',8'-tetramethoxy-6,6'-dimethyl-[1,3'-biisoquinoline]-3-carboxylate (S9)

bis-Isoquinoline S6 (1.40 g, 2.94 mmol, 1.00 equiv) and selenium dioxide (652 mg, 5.88 mmol, 2.00 equiv) was slurried in dioxane and the flask was fitted with a reflux condenser. The flask was vacuum purged/refilled with $N_2$ five times, then heated to reflux. At about 80° C. the solution became fully homogeneous. After 1 h at reflux, the flask was cooled to room temperature and LCMS showed full conversion to aldehyde S7. Celite was added to the crude reaction and the resulting slurry was filtered through more celite, rinsing with EtOAc. $SiO_2$ was added to the filtrate and the solution was concentrated. Due to the insolubility of the products, a mixture of MeOH and $CH_2Cl_2$ was required during purification by column chromatography (10% MeOH/DCM+1% $NEt_3$). During this process, the highly electrophilic aldehyde moiety is converted to the hemiacetal in a thermodynamic 85:15 mixture favoring the hemiacetal. The two products can neither be interconverted nor separated, and as such was characterized as a mixture. White solid, total mass=1.47 g, 85:15 molar ratio of S7:S9 by $^1H$ NMR, corresponding to 1.25 g hemiacetal S9 (2.39 mmol, 82% yield) and 220 mg S7 (0.45 mmol, 15% yield), 2.84 mmol total, 97% combined yield. Aldehyde S7: $^1H$ NMR (400 MHz, $CDCl_3$) δ 10.92 (s, 1H), 8.78 (s, 1H), 8.72 (s, 1H), 8.56 (s, 1H), 7.68 (d, J=1.2 Hz, 1H), 4.07 (s, 3H), 4.04 (s, 3H), 4.02 (s, 3H), 3.95 (s, 3H), 3.70 (s, 3H), 2.51 (d, J=1.0 Hz, 3H), 2.37 (s, 3H); $^{13}C$ NMR (101 MHz, $CDCl_3$) δ 193.4, 160.6, 154.8, 154.1, 151.8, 151.3, 151.0, 147.1, 139.2, 135.8, 128.7, 128.1, 125.3, 125.0, 124.1, 121.6, 119.1, 102.0, 67.2, 60.7, 60.6, 56.3, 46.1, 17.4. Hemiacetal S9: $^1H$ NMR (400 MHz, $CDCl_3$) δ 8.78 (d, J=0.8 Hz, 1H), 8.44 (s, 1H), 7.97 (s, 1H), 7.61 (d, J=1.1 Hz, 1H), 6.52 (d, J=10.6 Hz, 1H), 6.41 (d, J=10.6 Hz, 1H), 4.10 (s, 3H), 4.06 (s, 3H), 3.98 (s, 3H), 3.98 (s, 3H), 3.92 (s, 3H), 3.63 (s, 3H), 2.48 (d, J=1.0 Hz, 3H), 2.37 (s, 3H); $^{13}C$ NMR (101 MHz, $CDCl_3$) δ 166.8, 160.3, 155.2, 154.9, 152.9, 151.5, 148.6, 148.2, 138.9, 138.6, 136.5, 128.5, 127.9, 125.2, 124.9, 123.4, 120.1, 118.9, 101.5, 95.2, 62.3, 60.8, 60.3, 56.0, 55.2, 52.8, 17.3, 10.0. IR (thin film, NaCl): 3436.7, 2948.9, 2846.9, 1737.7, 1711.2, 1619.9, 1462.1, 1386.6, 1304.0, 1272.2, 1228.6, 1136.2, 1086.2, 1001.8, 900.5, 734.1; HRMS (ESI-TOF) for aldehyde S7 calc'd for $[M^+]$ $C_{27}H_{26}N_2O_7$=490.1740, found 490.1742; HRMS (ESI-TOF) for hemiacetal S9 calc'd for $[M^+]$ $C_{28}H_{30}N_2O_8$=522.2002, found 522.2005.

Methyl 1'-(hydroxymethyl)-5,7,7',8'-tetramethoxy-6,6'-dimethyl-[1,3'-biisoquinoline]-3-carboxylate dichloromethane solvate (22.$CH_2Cl_2$)

A mixture of bis-isoquinolines S7 and S9 (2.84 mmol in total, 1.00 equiv) was dissolved in $CH_2Cl_2$ (24 mL) and MeOH (6 mL, 0.1 M) and sodium borohydride (36.0 mg, 0.946 mmol, 0.33 equiv) was added. The solution immediately bubbled in a controlled fashion for ~1 minute, then stopped. 5 minutes after the addition of sodium borohydride LCMS showed complete and selective reduction to desired product 22. The reaction was quenched by the addition of citric acid monohydrate (594 mg, 2.84 mmol, 1.00 equiv) and water and the solution was stirred at 1500 rpm for 10 min, then is basified by the addition of saturated aqueous NaHCO$_3$. The layers were separated and the aqueous phase was extracted with CH$_2$Cl$_2$. The combined organic phases were dried over Na$_2$SO$_4$ and concentrated. The product was purified by column chromatography using a 1:1 mixture of CH$_2$Cl$_2$:EtOAc as the polar solvent (20-30-40-50-60-100% polar solvent/hex+1% NEt$_3$). Colorless solid, 1.55 g, 2.68 mmol, 98% yield. A stoichiometric amount of dichloromethane could not be removed from the product despite extensive time on high vacuum (10 mTorr), leading to the conclusion that the product is isolated as a stoichiometric dichloromethane solvate. Aldehyde S7 and hemiacetal S9 appear to be in thermal equilibrium at 23° C. in a 4:1 v/v mixture of CH$_2$Cl$_2$:MeOH in a 1:3 ratio of S7:S9. When excess NaBH$_4$ is utilized, competitive reduction of the methyl ester was observed; however, when NaBH$_4$ was employed in substoichiometric fashion, selective reduction of S7 was observed. $^1$H NMR (400 MHz, CDCl$_3$) δ 8.79 (d, J=0.8 Hz, 1H), 8.30 (s, 1H), 7.90 (s, 1H), 7.59 (d, J=0.5 Hz, 1H), 5.55 (t, J=3.5 Hz, 1H), 5.39 (d, J=3.5 Hz, 2H), 5.30 (s, 2H), 4.06 (s, 3H), 4.06 (s, 3H), 3.99 (s, 3H), 3.96 (s, 3H), 3.90 (s, 3H), 2.49 (d, J=0.9 Hz, 3H), 2.38 (s, 3H); $^1$H NMR (400 MHz, CDCl$_3$) δ 166.9, 160.2, 155.8, 155.6, 155.0, 151.1, 149.1, 148.5, 139.0, 138.4, 135.5, 128.5, 127.9, 125.3, 124.8, 121.6, 120.3, 118.8, 101.3, 64.7, 62.4, 60.9, 60.3, 56.1, 53.4, 52.9, 17.2, 10.0; IR (thin film, NaCl): 3364.8, 3130.4, 2930.2, 2856.2, 1690.6, 1620.8, 1594.3, 1556.6, 1462.3, 1413.2, 1391.8, 1356.6, 1330.7, 1302.1, 1258.7, 1196.3, 1130.7, 1088.7, 1058.5, 1010.1, 964.2, 885.9, 838.1, 801.9, 777.4, 734.0; HRMS (ESI-TOF) calc'd for [M$^+$] C$_{27}$H$_{28}$N$_2$O$_7$=492.1897, found 492.1894.

Example 5: Synthesis of Intermediate S8

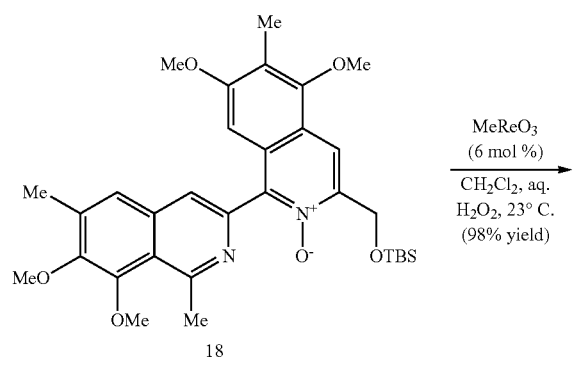

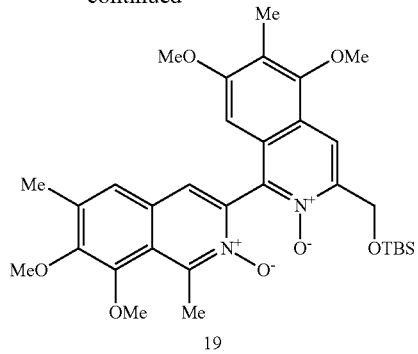

3-(((tert-butyldimethylsilyl)oxy)methyl)-5,7,7',8'-tetramethoxy-1',6,6'-trimethyl-[1,3'-biisoquinoline] 2,2'-dioxide (19)

Bis-isoquinoline-N-oxide 18 (100 mg, 0.173 mmol, 1 equiv) and methyl trioxorhenium (0.8 mg, 0.0032 mmol, 0.02 equiv) were dissolved in CH$_2$Cl$_2$ (1.7 mL, 0.1 M) and 35% aqueous hydrogen peroxide (26.5 μL, 0.86 mmol, 5 equiv) was added. Addition of the catalyst in a single portion resulted in rapid over-oxidation, but addition in 3 portions, at least 20 minutes apart resulted in clean conversion. The solution was stirred at 1300 rpm for 30 min, at which point a second portion of MeReO$_3$ (0.8 mg, 0.0032 mmol, 0.02 equiv) was added. After 30 min, a third and final portion of MeReO$_3$ (0.8 mg, 0.0032 mmol, 0.02 equiv) was added. After a further 30 min, LCMS showed complete conversion to the bis-N-oxide, so the reaction was quenched with aqueous sodium thiosulfate. The layers were separated and the aqueous phase was extracted with CH$_2$Cl$_2$ until no red color remained. bis-N-oxide 19 was not stable to Na$_2$SO$_4$, MgSO$_4$, or SiO$_2$, and as such it was neither dried nor purified by column chromatography. The solution was concentrated, providing the analytically pure bis-N-oxide. Red solid, 100.7 mg, 0.169 mmol, 98% yield. $^1$H NMR (400 MHz, CDCl$_3$) δ 8.18 (q, J=1.3 Hz, 1H), 7.57 (s, 1H), 7.31 (d, J=1.0 Hz, 1H), 6.41 (s, 1H), 5.13 (dd, J=17.0, 1.5 Hz, 1H), 5.02 (dd, J=17.0, 1.4 Hz, 1H), 3.99 (s, 3H), 3.95 (s, 3H), 3.91 (s, 3H), 3.68 (s, 3H), 3.21 (s, 3H), 2.41 (d, J=1.0 Hz, 3H), 2.27 (s, 3H), 1.03 (s, 9H), 0.17 (s, 3H), 0.17 (s, 3H); $^1$H NMR (101 MHz, CDCl$_3$) δ 159.4, 153.4, 153.0, 147.6, 146.1, 145.4, 138.9, 137.8, 135.5, 128.3, 126.3, 124.5, 124.5, 123.7, 122.8, 120.0, 115.2, 96.8, 61.8, 61.1, 60.6, 60.2, 55.7, 26.0, 18.4, 16.9, 15.4, 9.7, −5.2, −5.2; IR (thin film, NaCl): 2933.0, 2857.5, 2218.5, 1614.0, 1547.6, 1469.0, 1324.3, 1237.2, 1216.5, 1139.8, 1118.3, 1083.2, 1049.6, 1007.5, 975.3, 911.7, 838.9, 778.8, 730.6, 666.0, 642.6; HRMS (ESI-TOF) calc'd for [M$^+$] C$_{32}$H$_{42}$N$_2$O$_7$Si=594.2761, found 594.2757.

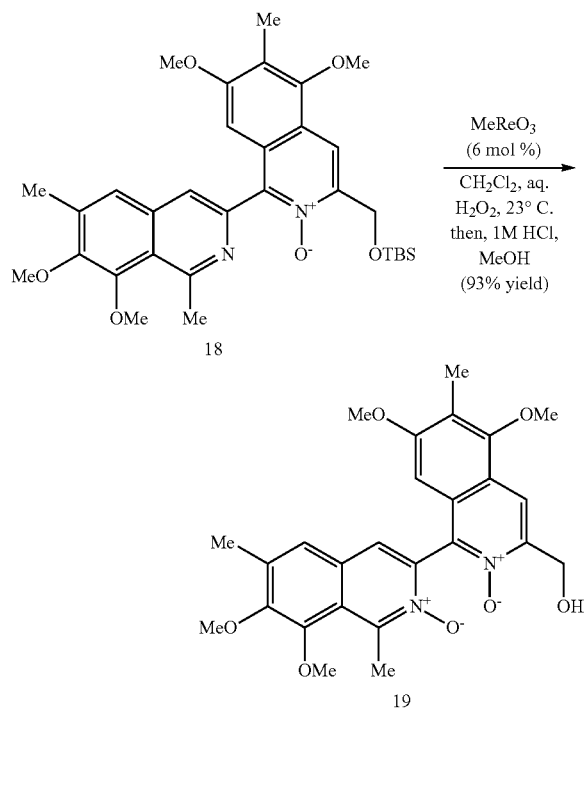

3-(hydroxymethyl)-5,7,7',8'-tetramethoxy-1',6,6'-trimethyl-[1,3'-biisoquinoline] 2,2'-dioxide (19)

Bis-isoquinoline-N-oxide 18 (500 mg, 0.86 mmol, 1 equiv) and methyl trioxorhenium (MTO, 4.3 mg, 0.017 mmol, 0.02 equiv) were dissolved in $CH_2Cl_2$ (8.6 mL, 0.1 M) and 35% aqueous hydrogen peroxide (132 µL, 1.5 mmol, 1.75 equiv) was added. Addition of the catalyst in a single portion resulted in rapid over-oxidation, but addition in 3 portions, 20 minutes apart resulted in clean conversion. The solution was stirred at 750 rpm for 20 min, at which point a second portion of MTO (4.3 mg, 0.017 mmol, 0.02 equiv) was added. After 20 min, a third and final portion of MTO (4.3 mg, 0.017 mmol, 0.02 equiv) was added. After a further 20 min (for a total of 1 h), LCMS showed complete conversion to the bis-N-oxide, so the reaction was diluted with 8.6 mL 1M HCl and 17 mL methanol was added to achieve phase mixing. After 16 h, LCMS showed complete conversion to the free alcohol. Any remaining oxidant was quenched with aqueous sodium thiosulfate, the layers were separated, and the aqueous phase was extracted with $CH_2Cl_2$ until no yellow color persisted. The combined organic phases were concentrated in vacuo and dried azeotropically with benzene, providing the analytically pure bis-N-oxide. bis-N-oxide 19 was not stable to $Na_2SO_4$, $MgSO_4$, or $SiO_2$, and as such it was neither dried nor purified by column chromatography. Yellow solid, 368 mg, 0.765 mmol, 89% yield. $^1$H NMR (500 MHz, $CDCl_3$) δ 8.19 (s, 1H), 7.91 (s, 1H), 7.58 (s, 1H), 6.71 (s, 1H), 5.09 (d, J=14.4 Hz, 1H), 4.87 (d, J=14.4 Hz, 1H), 4.05 (s, 3H), 4.03 (s, 3H), 3.94 (s, 3H), 3.80 (s, 3H), 3.47 (s, 3H), 2.51 (s, 3H), 2.30 (s, 3H); 160.7, 154.2, 154.1, 150.0, 143.9, 141.8, 138.3, 135.5, 129.9, 128.7, 128.5, 126.6, 126.0, 125.0, 123.8, 122.1, 118.8, 98.4, 62.3, 61.5, 61.2, 60.7, 56.4, 17.4, 17.0, 10.2; IR (thin film, NaCl): 3227.3, 2949.2, 2854.4, 1607.8, 1456.6, 1332.2, 1235.5, 1113.3, 1001.4, 896.5, 816.4, 728.6; HRMS (ESI-TOF) calc'd for [M+] $C_{26}H_{28}N_2O_7$=480.1897, found 480.1902.

Example 6: Synthesis of Compound 6

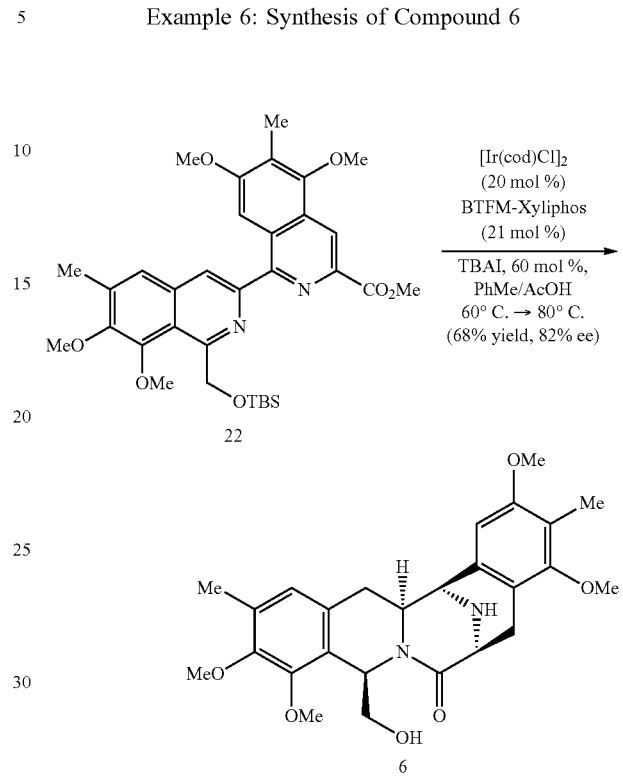

(6S,9R,14aS,15R)-9-(hydroxymethyl)-2,4,10,11-tetramethoxy-3,12-dimethyl-5,6,9,14,14a,15-hexahydro-7H-6,15-epiminobenzo[4,5]azocino[1,2-b]isoquinolin-7-one (6)

bis-Isoquinoline 22 (620 mg, 1.07 mmol, 1 equiv) was weighed in air into a 100 mL roundbottom flask with a teflon-coated stir bar and the flask was brought into a nitrogen-filled glovebox. Tetra-n-butylammonium iodide (238 mg, 0.644 mmol, 0.6 equiv, 3 equiv relative to Ir) was added to the flask, and this solution was added to the bis-isoquinoline slurry, resulting in a yellow solution of protonated 22, was suspended in 20 mL PhMe (22 is not fully soluble in PhMe alone). [Ir(cod)Cl]$_2$ (72.1 mg, 0.107 mmol, 0.1 equiv, 20 mol % Ir) and BTFM-Xyliphos (a.k.a. SL-J008-2, 205 mg, 0.225 mmol, 0.21 equiv) were dissolved in 10 mL PhMe in a scintillation vial and the resulting solution was allowed to stand for 10 min. 38.3 mL of toluene was added to the flask containing bis-isoquinoline 22, followed by the addition of 5.4 mL AcOH, resulting in a yellow solution of protonated 22. The iridium-ligand solution was then added to the flask with two 5 mL rinses, bringing the final volume to 53.7 mL of 9:1 PhMe:AcOH (0.02 M in 22). The flask was sealed with a rubber septum that was then pierced with three 16 gauge (purple) needles, each bent at a 90° angle. The flask was placed inside a pressure bomb, which was then sealed prior to removal from the glovebox via the large antechamber. At this stage, the tape was removed from the top of the bomb and the pressure gauge was quickly screwed in place and tightened. With 200 rpm stirring, the bomb was charged to 10 bar of H$_2$ and slowly released. This process was repeated twice, before charging the bomb to 60 bar of H₂, at which time it was placed in a preheated 60° C. oil bath. The bath was maintained at this temperature for 18 h, then raised to 80° C. for 24 h. At this time, the bomb was removed from the oil bath and the hydrogen pressure was vented. The flask was removed from the bomb and the solution was transferred to a 250 mL roundbottom flask and basified by the careful addition of saturated aqueous K₂CO₃ and water until pH >7. The solution was transferred to a separatory funnel and the layers were separated. The aqueous phase was extracted 5× with EtOAc, and the combined organic phases were washed twice with water and once with brine, dried over Na₂SO₄, and concentrated. The product was purified by column chromatography (15×1", 1% MeOH/DCM+1% NEt₃). At this stage, ¹H NMR determined the purity of the product to be 90% as a brown foam. 469 mg, 422 mg adjusted for purity, 0.899 mmol, 83% yield, 87% ee. Enantiomeric excess was determined by chiral HPLC analysis [AD, 20% IPA, 280 nm, 1.0 mL/min: t$_R$(minor)=21.6 min, t$_R$(minor)=26.9 min]. The product could then be crystallized to analytical and optical purity (>99% ee) by dissolving the brown foam in acetonitrile and allowing the solution to slowly evaporate under a stream of N₂. The crystals were washed 3× with 500 µL portions of −40° C. acetonitrile. The resulting crystals were dried in vacuo, providing 203 mg of enantiopure (>99% ee) bis-tetrahydroisoquinoline 6. The mother liquor could be purified by preparative SFC (AD-H, 20% IPA/CO₂, flow rate=40 mL/min, t$_R$(minor)=25.0 min, t$_R$(major)=30 min) to provide the remaining material in enantiopure fashion. The crystals isolated above were used to collect the following characterization data. ¹H NMR (500 MHz, CDCl₃) δ 6.73 (s, 1H), 6.35 (s, 1H), 5.79 (dd, J=6.7, 3.8 Hz, 1H), 4.12-4.10 (m, 2H), 3.93 (dt, J=12.7, 2.9 Hz, 1H), 3.91 (s, 3H), 3.83 (s, 3H), 3.78 (s, 3H), 3.70 (s, 3H), 3.43 (d, J=10.6 Hz, 1H), 3.22-3.10 (m, 3H), 3.03 (dd, J=17.2, 6.6 Hz, 1H), 2.74 (dd, J=14.5, 2.6 Hz, 1H), 2.67-2.60 (m, 1H), 2.25 (s, 3H), 2.15 (s, 3H); ¹³C NMR (126 MHz, CDCl₃) δ 172.9, 157.7, 156.6, 150.0, 149.7, 131.8, 131.2, 130.9, 125.0, 124.4, 119.8, 119.7, 106.1, 69.0, 61.7, 60.7, 60.4, 60.0, 55.9, 55.0, 54.4, 52.8, 33.2, 30.1, 15.9, 9.2; IR (thin film, NaCl): 3301.7, 3052.7, 2940.2, 2859.4, 2835.6, 1621.9, 1614.0, 1486.0, 1463.1, 1455.0, 1410.0, 1352.8, 1324.3, 1273.8, 1233.6, 1190.8, 1124.8, 1082.0, 1000.5, 957.7, 925.7, 894.4, 849.2, 816.5, 788.5, 734.8, 703.2; HRMS (ESI-TOF) calc'd for [M⁺] C₂₆H₃₂N₂O₆=468.2260, found 468.2255; [α]$_D$=−56.9° (c=0.5, CHCl₃).

Example 7: Synthesis of Compound 28

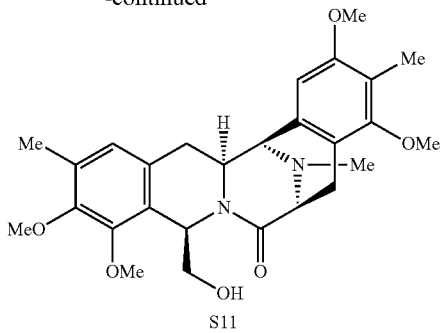

(6S,9R,14aS,15R)-9-(hydroxymethyl)-2,4,10,11-tetramethoxy-3,12,16-trimethyl-5,6,9,14,14a,15-hexahydro-7H-6,15-epiminobenzo[4,5]azocino[1,2-b]isoquinolin-7-one (S6)

Enantiopure bis-tetrahydroisoquinoline 6 (125 mg, 0.267 mmol, 1 equiv) was dissolved in 1,2-dichloroethane (1,2-DCE, 5.3 mL, 0.05 M) and 37% aqueous formaldehyde (100 µL, 1.33 mmol, 5 equiv) was added. The solution was stirred at 800 rpm for 10 min, before sodium triacetoxyborohydride (565 mg, 2.67 mmol, 10 equiv) was added. This solution was stirred at 23° C. for 30 min, at which time LCMS showed full conversion to the product. Citric acid monohydrate (840 mg, 4.00 mmol, 15 equiv) was added to the solution, followed by 20 mL water. This solution was stirred for 10 min before the slow addition of saturated aqueous K₂CO₃ until pH >7. The layers were separated and the aqueous phase was extracted with CH₂Cl₂. The combined organic phases were washed with brine, dried over Na₂SO₄ and concentrated. The product was purified by column chromatography (1% MeOH/DCM+1% NEt₃). Colorless solid, 118.5 mg, 0.246 mmol, 92% yield. ¹H NMR (500 MHz, CDCl₃) δ 6.72 (s, 1H), 6.34 (s, 1H), 5.77 (dd, J=6.5, 3.8 Hz, 1H), 4.00 (dt, J=12.4, 3.0 Hz, 1H), 3.90 (s, 3H), 3.83 (s, 3H), 3.80-3.76 (m, 2H), 3.78 (s, 3H), 3.70 (s, 3H), 3.44 (ddd, J=8.6, 7.1, 6.0 Hz, 1H), 3.22-3.15 (m, 2H), 3.14 (dd, J=17.6, 6.5 Hz, 1H), 2.96 (br s, 1H), 2.94 (dd, J=17.6, 1.2 Hz, 1H), 2.67 (dd, J=14.5, 2.6 Hz, 1H), 2.62-2.53 (m, 1H), 2.47 (s, 3H), 2.24 (s, 3H), 2.15 (s, 3H); ¹³C NMR (126 MHz, CDCl₃) δ 173.4, 157.4, 156.7, 150.0, 149.7, 131.7, 131.5, 128.8, 125.0, 124.4, 119.7, 119.0, 106.9, 69.1, 61.4, 60.7, 60.4, 60.3, 60.0, 58.4, 55.9, 52.8, 46.1, 40.1, 33.0, 24.2, 15.9; IR (thin film, NaCl): 3382.5, 2938.3, 2862.0, 1633.4, 1608.1, 1485.1, 1462.9, 1445.8, 1410.0, 1359.5, 1325.2, 1271.9, 1232.7, 1189.7, 1123.5, 1080.0, 1015.0, 1001.3, 962.6, 910.0, 847.7, 803.5, 646.4; HRMS (ESI-TOF) calc'd for [M⁺] C₂₇H₃₄N₂O₆=482.2417, found 482.2414; [α]$_D$=−76.2° (c=0.5, CHCl₃).

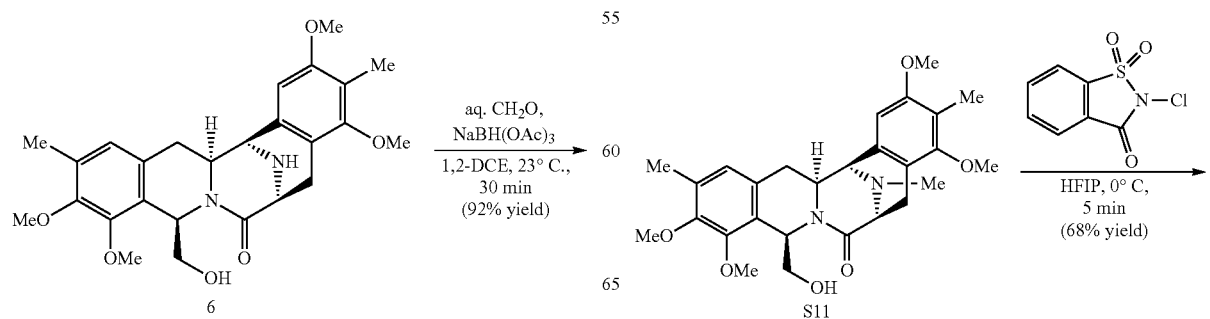

77

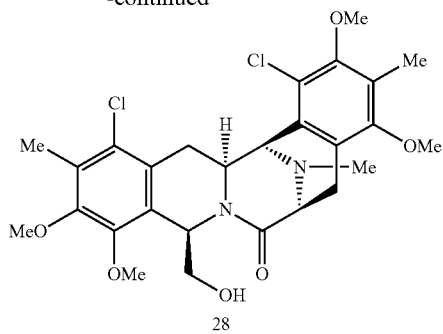

(6S,9R,14aS,15R)-1,13-dichloro-9-(hydroxymethyl)-2,4,10,11-tetramethoxy-3,12,16-trimethyl-5,6,9,14,14a,15-hexahydro-7H-6,15-epiminobenzo[4,5]azocino[1,2-b]isoquinolin-7-one (28)

bis-Tetrahydroisoquinoline S11 (88.6 mg, 0.183 mmol, 1.00 equiv) was dissolved in HFIP (8.2 mL, 0.02 M after complete addition) and the solution was cooled to 0° C. N-Chlorosaccharine (87.7 mg, 0.403 mmol, 2.20 equiv) was dissolved in 1 mL HFIP and this solution was added at a slow dropwise pace, allowing the orange color to dispel after each addition, and the resulting yellow solution was stirred at 0° C. An LCMS sample taken 5 min after complete addition showed complete dichlorination, so the reaction was quenched by the addition of saturated aqueous $Na_2S_2O_3$. The resulting mixture was transferred to a separatory funnel with and diluted with $CH_2Cl_2$, creating a triphasic system with HFIP on bottom, $CH_2Cl_2$ on the bottom, and the aqueous phase on top. The bottom two phases were collected directly in a 250 mL roundbottom flask. The aqueous phase was basified with $K_2CO_3$ and extracted with $CH_2Cl_2$, draining the organic phase directly into the flask. Excess acetic acid (100 μL) was added and the solution was concentrated, removing excess acetic acid by azeotropic drying with toluene, and the resulting foam was dried at <1 torr for 1 h. The crude product was dissolved in $CH_2Cl_2$ and washed with dilute aqueous $K_2CO_3$ and the layers were separated. The aqueous phase was extracted with $CH_2Cl_2$ and the combined organic phases were dried over $Na_2SO_4$ and concentrated. The product was purified by column chromatography (1% $MeOH/CH_2Cl_{2+1}\%$ $NEt_3$). White solid, 69.0 mg, 0.125 mmol, 68% yield. H NMR (500 MHz, $CDCl_3$) δ 5.85 (dd, J=7.2, 4.1 Hz, 1H), 4.47 (dd, J=3.7, 1.1 Hz, 1H), 4.04 (ddd, J=12.8, 3.7, 2.6 Hz, 1H), 3.90 (s, 3H), 3.82 (dd, J=15.6, 2.6 Hz, 1H), 3.82 (s, 3H), 3.78-3.76 (m, 1H), 3.77 (s, 3H), 3.72 (s, 3H), 3.42 (dt, J=10.8, 4.8 Hz, 1H), 3.18 (dd, J=7.0, 4.8 Hz, 1H), 3.13 (dd, J=18.2, 6.7 Hz, 1H), 3.13-3.08 (m, 1H), 3.00 (dd, J=18.1, 1.3 Hz, 1H), 2.45 (s, 3H), 2.31 (s, 3H), 2.27 (s, 3H), 2.17 (dd, J=15.6, 12.8 Hz, 1H); 173.3, 156.1, 153.8, 150.4, 148.3, 130.7, 129.8, 128.0, 127.9, 126.2, 125.6, 124.5, 123.9, 69.1, 60.9, 60.5, 60.4, 60.4, 59.5, 58.8, 57.6, 52.1, 40.3, 29.5, 24.7, 13.8, 10.1; IR (thin film, NaCl): 3417.7, 2939.6, 1643.6, 1633.8, 1462.1, 1454.8, 1403.6, 1360.5, 1329.7, 1272.2, 1236.1, 1224.0, 1191.6, 1146.7, 1105.6, 1081.9, 1004.6, 951.2, 931.7, 833.0, 793.8, 767.9, 736.2, 702.5; HRMS (ESI-TOF) calc'd for [M+] $C_{27}H_{32}N_2O_6Cl_2$=550.1637, found 550.1637; $[\alpha]_D$=−119.0° (c=0.5, $CHCl_3$).

78

Example 8: Synthesis of Compound S13

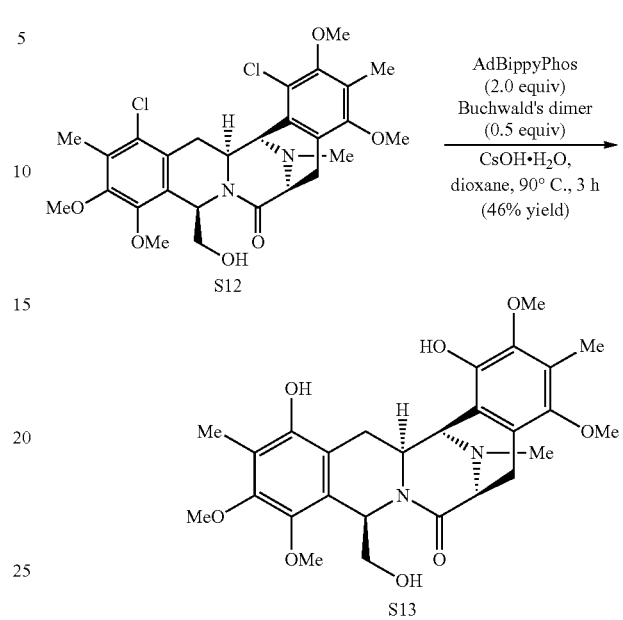

(6S,9R,14aS,15R)-1,13-dihydroxy-9-(hydroxymethyl)-2,4,10,11-tetramethoxy-3,12,16-trimethyl-5,6,9,14,14a,15-hexahydro-7H-6,15-epiminobenzo[4,5]azocino[1,2-b]isoquinolin-7-one (S13)

7-one (S13). In a nitrogen-filled glovebox, (2'-Amino-1,1'-biphenyl-2-yl)methanesulfonatopalladium(II) dimer (Buchwald's dimer, 33.5 mg, 0.0453 mmol, 0.500 equiv) and 5-[di(1-adamantyl)phosphino]-1',3',5'-triphenyl-1'H-[1,4']bipyrazole (AdBippyPhos, 120.2 mg, 0.181 mmol, 2.00 equiv) were weighed into a scintillation vial and dioxane (8.1 mL) was added. The vial was sealed with electrical tape and removed from the glovebox, sonicated briefly, and returned to the glovebox. The resulting tan solution was then transferred to a 20 mL microwave vial containing bis-tetrahydroisoquinoline 28 (50.0 mg, 0.0907 mmol, 1.00 equiv) and $CsOH.H_2O$ (152.3 mg, 0.907 mmol, 10.0 equiv), followed by a 1 mL rinse (9.1 mL total volume, 0.01 M in 28). The vial was sealed, removed from the glovebox, and placed in a preheated 90° C. oil bath. After 3 h, the vial was removed and allowed to cool fully to room temperature prior to removing the seal. If the reaction vessel is prematurely exposed to air at elevated temperature, aerobic oxidation leads to the formation of quinones, which undergo hydrolysis of the vinylogous ester in the presence of CsOH. The solution must be fully cooled to room temperature prior to breaking the seal. The bisphenol product is not sensitive to aerobic oxidation, in the solid state or in solution. Acetic acid (46.5 μL, 0.813 mmol, 9 equiv) was added to quench remaining CsOH and the contents of the vial were transferred to a roundbottom flask, to which silica gel was added directly to dry load onto a silica gel column. The solution was concentrated, and the product was purified by column chromatography (2-4-6-8-10% $MeOH+CH_2Cl_2$: 200 mL portions, no $NEt_3$ added, product elutes in the 6% portion). Tan solid, 17.2 mg, 0.0334 mmol, 37% yield. $^1$H NMR (500 MHz, $CDCl_3$) δ 5.80 (dd, J=7.2, 4.2 Hz, 1H), 4.34 (d, J=2.0 Hz, 1H), 3.96 (dt, J=12.3, 2.5 Hz, 1H), 3.81 (s, 3H), 3.80

(dd, J=6.0, 1.0 Hz, 1H), 3.77 (s, 3H), 3.75 (s, 3H), 3.65 (s, 3H), 3.52 (br s, 1H), 3.46 (dd, J=15.7, 2.6 Hz, 1H), 3.42 (dd, J=11.0, 4.5 Hz, 1H), 3.23 (dd, J=10.8, 7.2 Hz, 1H), 3.14 (dd, J=18.1, 6.7 Hz, 1H), 3.02 (d, J=18.0 Hz, 1H), 2.45 (s, 3H), 2.21 (s, 3H), 2.14 (s, 3H), 2.09 (dd, J=15.2, 12.2 Hz, 1H); $^{13}$C NMR (126 MHz, CDCl$_3$) δ 173.6, 150.0, 149.7, 146.8, 144.1, 143.5, 143.4, 124.6, 123.7, 122.6, 118.6, 118.3, 115.9, 69.2, 61.0, 60.9, 60.4, 60.3, 59.6, 59.0, 55.3, 52.5, 40.1, 25.2, 24.5, 9.7, 9.3, 1.2; IR (thin film, NaCl): 3332.3, 2937.3, 1613.3, 1462.2, 1453.3, 1413.6, 1353.2, 1302.2, 1191.4, 1108.8, 1068.0, 1005.9, 910.3, 836.1, 806.3, 730.6; HRMS (ESI-TOF) calc'd for [M$^+$] C$_{27}$H$_{34}$N$_2$O$_8$=514.2315, found 514.2311; [α]$^D$=91.6° (c=0.5, CHCl$_3$).

Example 9: Synthesis of Compound S14

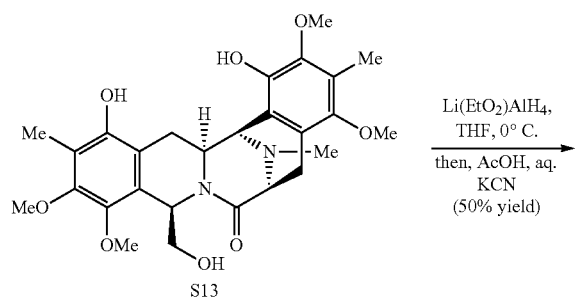

S13

6S,7R,9R,14aS,15R)-1,13-dihydroxy-9-(hydroxymethyl)-2,4,10,11-tetramethoxy-3,12,16-trimethyl-6,7,9,14,14a,15-hexahydro-5H-6,15-epiminobenzo[4,5]azocino[1,2-b]isoquinoline-7-carbonitrile (S14)

In an oven-dried vial, LiAlH$_4$ solution (1.0 M in THF, 2 mL, 2.0 mmol) was cooled to 0° C. A solution of ethyl acetate (230 μL, 2.35 mmol) in 2 mL THF was added slowly, and the resulting solution was stirred 30 min at 0° C., providing a 0.47 M solution of Li(EtO)$_2$AlH$_2$ in THF. bis-Tetrahydroisoquinoline S13 (49.0 mg, 0.095 mmol, 1.0 equiv) was dissolved in THF (4.8 mL, 0.02 M) and the resulting solution was cooled to 0° C. A solution of Li(EtO)$_2$AlH$_2$ (0.47 M in THF, 3.0 mL, 1.43 mmol, 15.0 equiv) was added slowly, resulting in extensive evolution of H$_2$. After stirring 45 min, the reaction was quenched with acetic acid (115 μL, 2.00 mmol, 21 equiv) and aqueous potassium cyanide (4.8 M, 120 μL, 0.571 mmol, 6.0 equiv) was added, followed by celite and anhydrous Na$_2$SO$_4$ (roughly 1 g each). The solution was diluted with 8 mL THF and stirred 10 h, warming to room temperature. More celite was added, and the suspension was filtered through celite, rinsing with EtOAc. The filtrate was transferred to a roundbottom flask and was concentrated. At this stage, LCMS revealed a ~4:1 mixture of product S14 and starting material S13, so the crude mixture was resubjected to the reduction conditions, using 3 mL THF as the reaction solvent and 1 mL of freshly prepared Li(EtO)$_2$AlH$_2$ solution. After 10 min, LCMS showed very little conversion of the remaining starting material, with some over-reduced product (m/z=501). The reaction mixture was quenched and worked up as described above. The product was purified by column chromatography (50-75-100% EtOAc/hex, 200 mL each; product elutes in the 75% portion). Colorless solid, 25.2 mg, 0.0479 mmol, 50% yield $^1$H NMR (400 MHz, CDCl$_3$) δ 4.19 (dD, J=2.7, 1.1 Hz, 1H), 4.00-4.05 (m, 2H), 3.81 (s, 3H), 3.751 (s, 3H), 3.749 (s, 3H), 3.70 (s, 3H), 3.56 (dd, J=10.9, 4.4 Hz, 1H), 3.40 (ddd, J=7.5, 2.5, 1.2 Hz, 1H), 3.31 (dt, J=12.1, 2.7 Hz, 1H), 3.18 (d, J=9.4 Hz, 1H), 3.13 (dd, J=15.6, 2.7 Hz, 1H), 3.10 (dd, J=18.6, 7.8 Hz, 1H), 2.51 (d, J=18.6 Hz, 1H), 2.34 (s, 3H), 2.22 (s, 3H), 2.09 (s, 3H), 1.85 (dd, J=15.6, 12.0 Hz, 1H); $^{13}$C NMR (101 MHz, CDCl$_3$) δ 149.6, 148.7, 146.6, 143.7, 143.4, 143.1, 125.4, 123.5, 122.7, 118.1, 118.0, 117.1, 116.7, 66.2, 61.2, 61.0, 60.8, 60.4, 60.2, 58.5, 57.1, 56.7, 55.2, 41.9, 25.4, 21.7, 9.8, 9.0; IR (thin film, NaCl): 3427.6, 2936.1, 2832.7, 2228.1, 1606.8, 1463.2, 1412.1, 1384.5, 1349.9, 1319.9, 1300.9, 1251.3, 1218.1, 1191.3, 1150.7, 1107.7, 1070.1, 1001.7, 981.7, 907.7, 875.4, 829.8, 754.4; HRMS (ESI-TOF) calc'd for [M$^+$] C$_{28}$H$_{35}$N$_3$O$_7$=525.2475, found 525.2471; [α]$_D$=+22.9° (c=0.5, CHCl$_3$).

Example 10: Synthesis of (−)-Jorunnamycin A (S15)

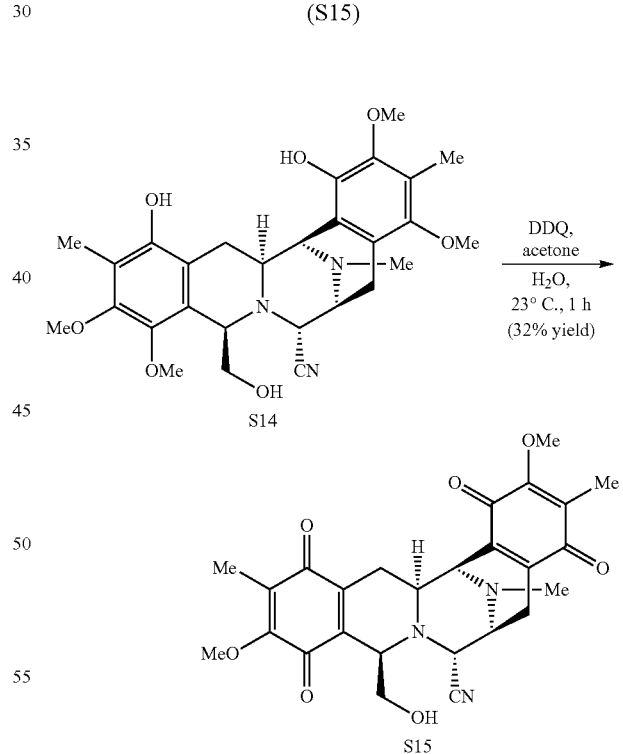

bis-Tetrahydroisoquinoline S14 (22.0 mg, 41.9 μmol, 1.0 equiv) and 4,5-dichloro-3,6-dioxocyclohexa-1,4-diene-1,2-dicarbonitrile (DDQ, 38.0 mg, 167 μmol, 4.0 equiv) were weighed into a roundbottom flask and 8.4 mL of a 9:1 mixture of acetone and water was added (0.005 M). The purple solution gradually turned blood red. After 1 h, the reaction was quenched with saturated aqueous NaHCO$_3$. The phases were separated and the aqueous phase was extracted with ethyl acetate. The combined organic phases were washed with brine, dried over Na$_2$SO$_4$ and concentrated. The product was purified using reverse phase (C$_{18}$) preparative HPLC (MeCN/0.4% acetic acid in water, 5.0 mL/min, monitor wavelength=254 nm, 20-70% MeCN over 5 min, hold at 70% for 3 min, hold at 95% for 2 min. Product has t$_R$=7.2 min). Yellow film, 6.6 mg, 13.4 μmol, 32% yield. $^1$H NMR (500 MHz, CDCl$_3$) δ 4.11 (d, J=2.6 Hz, 1H), 4.08 (dd, J=3.0, 1.0 Hz, 1H), 4.03 (s, 3H), 3.99 (s, 3H), 3.90 (q, J=3.1 Hz, 1H), 3.71 (dd, J=11.3, 3.4 Hz, 1H), 3.50 (s, 1H), 3.42 (ddd, J=7.4, 2.6, 1.5 Hz, 1H), 3.18 (dt, J=11.4, 2.9 Hz, 1H), 2.93 (ddd, J=17.4, 2.8, 0.9 Hz, 1H), 2.83 (dd, J=21.0, 7.5 Hz, 1H), 2.31 (s, 3H), 2.26 (d, J=21.0 Hz, 1H), 1.95 (s, 3H), 1.94 (s, 3H), 1.41 (ddd, J=17.5, 11.5, 2.7 Hz, 1H); IR (thin film, NaCl): 3508.5, 2943.0, 2226.8, 1651.8, 1620.8, 1447.2, 1373.6, 1310.6, 1277.4, 1236.0, 1190.6, 1151.1, 1098.1, 1077.8, 963.7, 886.8, 775.3; HRMS (ESI-TOF) calc'd for [M$^+$] C$_{28}$H$_{27}$N$_3$O$_7$=493.1849, found 493.1848; [α]$_D$=−94.3° (c=0.35, CHCl$_3$).

Example 11: Synthesis of (−)-Jorumycin (1)

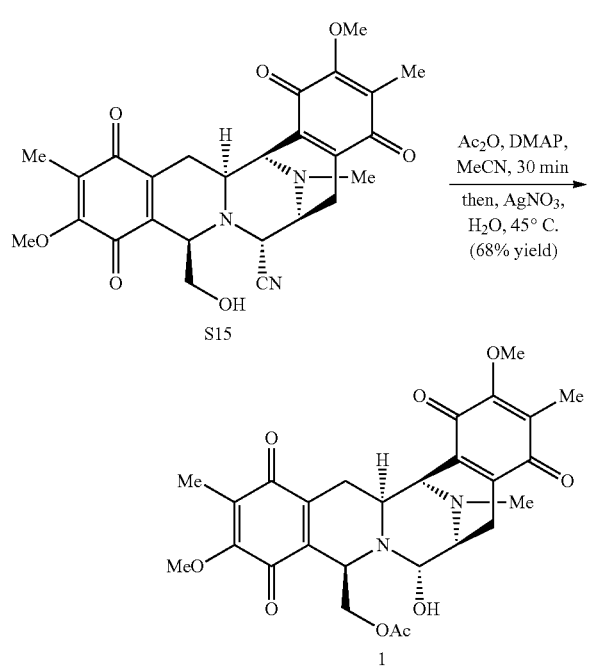

In a 1-dram vial, Jorunnamycin A (S15, 6.6 mg, 13.4 μmol, 1.0 equiv) and 4-dimethylaminopyridine (DMAP, 4.9 mg, 40.1 μmol, 3.0 equiv) were dissolved in acetonitrile (400 μL, 0.03 M) and acetic anhydride (3.8 μL, 40.1 μmol, 3.0 equiv) was added neat. The brown solution immediately turned yellow. After 30 minutes, LCMS showed complete conversion to the acetylated intermediate. At this stage, silver nitrate (57.0 mg, 334 μmol, 25.0 equiv) and water (260 μL) were added in rapid succession. The vial was resealed and placed in a preheated 45° C. heating block, then protected from light with aluminum foil. After 30 minutes, LCMS showed complete conversion to (−)-jorumycin (1), so the solution was filtered to remove AgCN and silver black, and the crude reaction mixture was purified directly using preparative HPLC (MeCN/0.4% acetic acid in water, 5.0 mL/min, monitor wavelength=265 nm, 10-55% MeCN over 7 min, ramp to 95% MeCN over 0.2 min, hold at 95% for 1.8 min for a total run time of 9 min. Product has t$_R$=6.6 min). Yellow film, 4.8 mg, 9.12 μmol, 68% yield. $^1$H NMR (500 MHz, CDCl$_3$) δ 4.44 (dd, J=11.2, 3.5 Hz, 1H), 4.44 (br s, 1H), 4.37 (d, J=3.1 Hz, 1H), 4.01 (s, 3H), 3.99 (s, 3H), 3.92 (br s, 1H), 3.82 (dd, J=11.3, 3.4 Hz, 1H), 3.21-3.16 (m, 1H), 3.14 (dd, J=7.3, 4.7 Hz, 1H), 2.84 (dd, J=16.6, 2.4 Hz, 1H), 2.66 (dd, J=21.1, 7.6 Hz, 1H), 2.27 (s, 3H), 2.23 (d, J=21.0 Hz, 1H), 1.96 (s, 3H), 1.94 (s, 3H), 1.76 (s, 3H), 1.24 (ddd, J=16.6, 11.3, 2.6 Hz, 1H); $^{13}$C NMR (126 MHz, CDCl$_3$) δ 186.0, 181.4, 170.2, 155.8, 155.4, 142.1, 142.0, 137.4, 128.9, 128.5, 83.1, 64.4, 61.19, 61.17, 57.6, 54.4, 52.9, 51.1, 41.6, 25.7, 20.74, 20.69, 8.9, 8.8; IR (thin film, NaCl): 3478.3, 2923.5, 2850.7, 1738.4, 1651.6, 1620.8, 1449.0, 1373.6, 1309.4, 1260.4, 1233.9, 1188.7, 1149.6, 1096.2, 1083.0, 1013.2, 901.9, 871.7, 839.6, 801.2, 730.2; HRMS (ESI-TOF) calc'd for [M$^+$] C$_{27}$H$_{30}$N$_2$O$_9$=526.1951, found 526.1956.

Example 12: Monoisoquinoline Hydrogenation

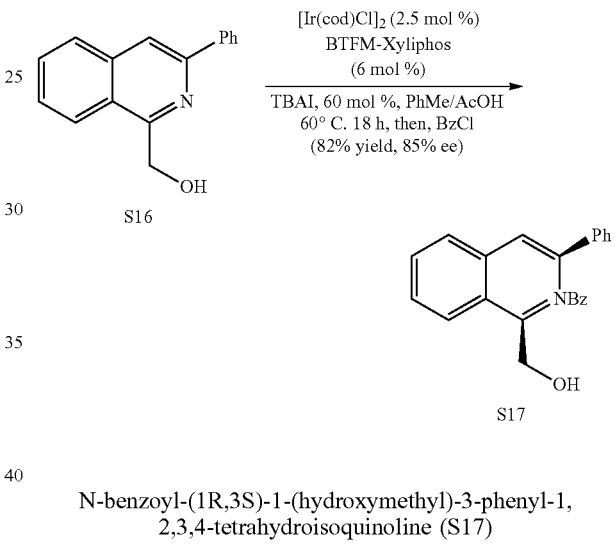

N-benzoyl-(1R,3S)-1-(hydroxymethyl)-3-phenyl-1,2,3,4-tetrahydroisoquinoline (S17)

bis-Isoquinoline S16 (85 mg, 0.36 mmol, 1 equiv) was weighed in air into a 100 mL roundbottom flask with a teflon-coated stir bar and the flask was brought into a nitrogen-filled glovebox. Tetra-n-butylammonium iodide (19.9 mg, 0.054 mmol, 0.15 equiv, 3 equiv relative to Ir) was added to the flask. [Ir(cod)Cl]$_2$ (6.0 mg, 0.009 mmol, 0.025 equiv, 5 mol % Ir) and BTFM-Xyliphos (SL-J008-2, 19.7 mg, 0.0216 mmol, 0.06 equiv) were dissolved in 6.2 mL PhMe in a scintillation vial and the resulting solution was allowed to stand for 10 min. 10.2 mL of toluene was added to the flask containing bis-isoquinoline S16 and TBAI, followed by the addition of 5.4 mL AcOH, resulting in a yellow solution of protonated S16. The iridium-ligand solution was then added to the flask (0.02 M in S16). The flask was sealed with a rubber septum that was then pierced with three 16 gauge (purple) needles, each bent at a 90° angle. The flask was placed inside the bomb, which was then sealed prior to removal from the glovebox via the large antechamber. At this stage, the tape was removed from the top of the bomb and the pressure gauge was quickly screwed in place and tightened. With 200 rpm stirring, the bomb was charged to 10 bar of H$_2$ and slowly released. This process was repeated twice, before charging the bomb to 60 bar of H$_2$, at which time it was placed in a preheated 60° C. oil bath. The bath was maintained at this temperature for 18 h, then raised to 80° C. for 24 h. At this time, the bomb was removed from the oil bath and the hydrogen pressure was vented. The flask was removed from the bomb and the solution was transferred to a 250 mL roundbottom flask and basified by the careful addition of saturated aqueous K₂CO₃ and water until pH >7. The solution was transferred to a separatory funnel and the layers were separated. The aqueous phase was extracted 5× with EtOAc, and the combined organic phases were washed twice with water and once with brine, dried over Na₂SO₄, and concentrated. The crude tetrahydroisoquinoline was dissolved in 3 mL THF and triethylamine (3 equiv), DMAP (0.1 equiv), and benzoyl chloride (3 equiv) were added. The solution was stirred at 23° C. for 45 min. Methanol (1 mL) and water (1 mL) were then added, followed by lithium hydroxide monohydrate (10 equiv). The solution was stirred 1 h at 23° C., at which time the solution was diluted with saturated aqueous NaHCO₃. The layers were separated and the aqueous layer was extracted with EtOAc. The combined organic phases were washed with brine, dried with Na₂SO₄, and concentrated. The product was purified by column chromatography (1% MeOH in DCM). Colorless solid, 101.4 mg, 0.30 mmol, 82% yield, 85% ee. Enantiomeric excess was determined by chiral SFC analysis [AD, 20% IPA, 254 nm, 3.0 mL/min: $t_R$(minor)= 3.78 min, $t_R$(minor)=5.15 min]. ¹H NMR (500 MHz, CDCl₃) δ 7.53-7.51 (m, 2H), 7.42-7.38 (m, 2H), 7.36-7.27 (m, 5H), 7.25-7.19 (m, 2H), 7.08-7.05 (m, 1H), 5.51-5.48 (m, 1H), 4.76 (td, J=2.0, 0.9 Hz, 1H), 4.25-4.21 (m, 1H), 4.04-4.01 (m, 1H), 3.59 (ddd, J=14.7, 3.6, 0.9 Hz, 1H), 2.95-2.89 (m, 2H); ¹H NMR (500 MHz, CDCl₃) δ 169.3, 140.0, 136.8, 135.8, 132.9, 131.5, 128.5, 128.2, 128.2, 128.1, 127.8, 127.7, 126.9, 126.0, 123.6, 63.3, 61.7, 59.7, 37.4; HRMS (ESI-TOF) calc'd for [M⁺] C₂₃H₂₁NO₂=344.1645, found 344.1646.

Example 13: Synthesis of BTFM-Xyliphos (27)

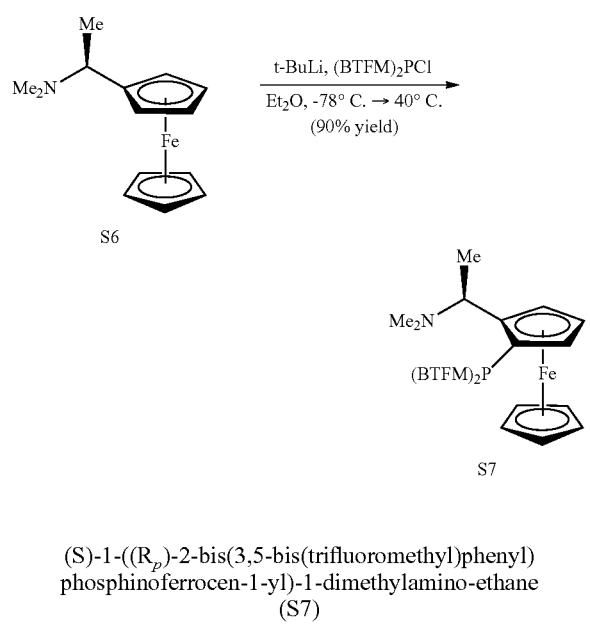

(S)-1-((R$_p$)-2-bis(3,5-bis(trifluoromethyl)phenyl)phosphinoferrocen-1-yl)-1-dimethylamino-ethane (S7)

In a flame-dried 2-neck roundbottom flask equipped with a reflux condenser, (S)-1-ferrocenyldimethylaminoethane (S6) (2.18 g, 8.46 mmol, 1 equiv) was dissolved in diethyl ether (85 mL, 0.1 M) and the solution was cooled to −78° C. t-Butyllithium in pentane (1.81 M, 5.85 mL, 10.6 mmol, 1.25 equiv) was added at a dropwise pace over 20 min, causing the yellow solution to turn orange. The solution was stirred 10 min at −78° C., then removed from its bath and stirred for 1.5 h at 23° C., turning red. A solution of bis(3,5-bistrifluoromethylphenyl)chloro-phosphane [(BTFM)₂PCl, 5.0 g, 10.1 mmol, 1.2 equiv) dissolved in 5 mL diethyl ether was added at a dropwise pace, followed by a 5 mL rinse. The solution quickly turned brown and eventually precipitated LiCl, and the solution was heated to reflux. After 1 h LCMS showed full conversion to product, so the reaction was quenched by the addition of ice followed by saturated aqueous NaHCO₃. The layers were separated and the aqueous phase was extracted once with diethyl ether. The combined organic phases were washed with brine, dried over Na₂SO₄ and concentrated. The product was purified by column chromatography (10% EtOAc/hex+0.5% NEt₃) as the major orange band. Dark orange oil, 5.46 g, 7.65 mmol, 90% yield. NMR spectra were identical to the previously reported compound.$^v$ ¹H NMR (300 MHz, CDCl₃) δ 7.97 (br s, 1H), 7.95 (br s, 1H), 7.91 (br s, 1H), 7.75 (br s, 1H), 7.63 (br s, 1H), 7.61 (br s, 1H), 4.49 (q, J=2.2 Hz, 1H), 4.36 (t, J=2.6 Hz, 1H), 4.13 (qd, J=6.8, 2.4 Hz, 1H), 4.02 (s, 5H), 3.65 (dt, J=2.4, 1.1 Hz, 1H), 1.70 (s, 6H), 1.21 (d, J=6.7 Hz, 3H); ¹⁹F NMR (282 MHz, CDCl₃) δ −62.8, −62.9; ³¹P NMR (121 MHz, CDCl₃) δ −19.8.

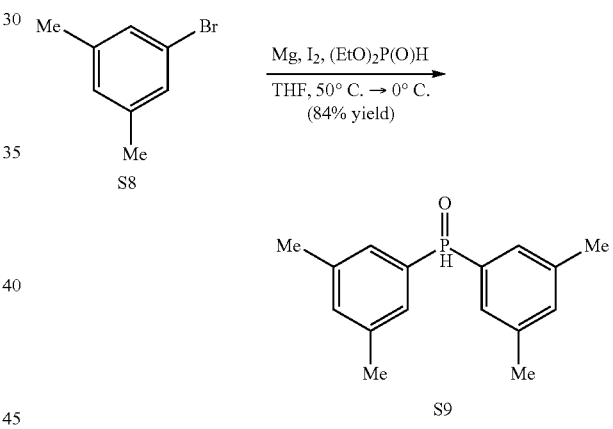

Bis(3,5-dimethylphenyl)phosphine oxide (S9)

Magnesium turnings (5.10 g, 210 mmol, 6 equiv) were washed with hexanes and dried in a 120° C. oven for 1 h. The turnings were placed in a 500 mL 3-neck roundbottom flask and flame dried under vacuum. Upon cooling to room temperature, a small amount of iodine (50 mg) was added to the flask, and the solids were suspended in THF (120 mL). The flask was fitted with a reflux condenser, then vacuum purged/backfilled with nitrogen three times, and warmed to 50° C. in an oil bath. A vent needle was added at the top of the reflux condenser to allow rapid gas release during the initiation of Grignard formation. Neat 3,5-dimethylbromobenzene (14.3 mL, 105 mmol, 3 equiv) was then added at a slow dropwise pace. Formation of the Grignard reagent was indicated by the disappearance of the dark brown THF-iodine adduct, at which point the addition was halted until a controlled, gentle reflux was obtained, and the vent needle was removed. Dropwise addition of the bromide was resumed so as to maintain a gentle reflux. After the addition was complete, the solution was stirred at 50° C. for 30 min, then removed from its bath and cooled to 0° C. in an ice/water bath. Diethyl phosphite (4.5 mL, 35 mmol, 1 equiv) was added at a fast dropwise pace, and the solution was stirred at 0° C. for 1 h. At this time, the reflux condenser was replaced with an addition funnel, and ice cold 6M HCl (40 mL, prepared by mixing 20 g ice with 20 mL concentrated HCl) was added at a slow dropwise pace. 300 mL water was added and the solution was stirred vigorously for 1 h. The layers were separated and the aqueous phase was thrice extracted with EtOAc. The combined organic layers were washed with brine, dried over $Na_2SO_4$ and concentrated. The product was purified by column chromatography (1-3-5% MeOH/DCM). White solid, 7.58 g, 29.3 mmol, 84% yield. NMR spectra were identical to the previously isolated compound.[vi] $^1$H NMR (300 MHz, $CDCl_3$) δ 7.94 (d, J=477 Hz, 1H), 7.32 (dt, J=1.5, 0.7 Hz, 2H), 7.28 (dt, J=1.6, 0.7 Hz, 2H), 7.17 (tp, J=1.7, 0.8 Hz, 2H), 2.34 (p, J=0.6 Hz, 12H); $^{31}$P NMR (121 MHz, $CDCl_3$) δ 22.71.

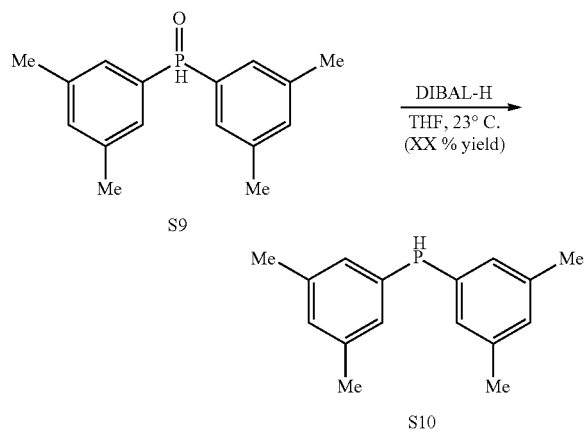

S9

Bis(3,5-dimethylphenyl)phosphane (S10)

The phosphine oxide was reduced using the procedure of Busacca et al.[vii] Colorless oil. NMR spectra were identical to the previously isolated compound.[41] $^1$H NMR (300 MHz, $C_6D_6$) δ 7.23 (dh, J=1.8, 0.6 Hz, 2H), 7.21 (dh, J=1.8, 0.6 Hz, 2H), 6.70 (dtq, J=1.8, 1.3, 0.7 Hz, 2H), 5.32 (d, J=214.7 Hz, 1H), 2.02 (q, J=0.7 Hz, 12H); $^{31}$P NMR (121 MHz, $C_6D_6$) δ −39.9.

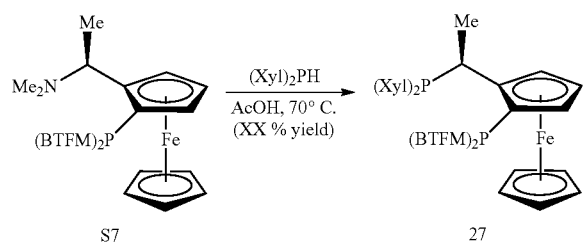

BTFM-Xyliphos (27)

The ligand was synthesized by adapting the procedure from Dorta et al. for the synthesis of Xyliphos.[41] Orange solid. NMR spectra were identical to the previously isolated compound.[6] $^1$H NMR (300 MHz, $C_6D_6$) δ 8.12 (dt, J=1.9, 0.6 Hz, 1H), 8.11-8.09 (m, 1H), 7.95 (dq, J=1.8, 0.6 Hz, 1H), 7.93-7.91 (m, 1H), 7.70 (dh, J=1.5, 0.7 Hz, 1H), 7.61-7.58 (m, 1H), 7.24 (dt, J=1.4, 0.7 Hz, 1H), 7.23-7.21 (m, 1H), 7.14 (dd, J=1.6, 0.8 Hz, 1H), 7.11 (dd, J=1.6, 0.8 Hz, 1H), 6.83 (tq, J=1.6, 0.8 Hz, 1H), 6.67 (dp, J=1.7, 0.8 Hz, 1H), 4.07 (dtd, J=9.8, 6.9, 2.8 Hz, 1H), 3.97 (tt, J=2.6, 0.6 Hz, 1H), 3.83-3.74 (m, 1H), 3.80-3.71 (m, 1H), 3.60 (s, 5H), 2.17 (q, J=0.6 Hz, 6H), 2.05 (d, J=0.7 Hz, 6H), 1.50 (dd, J=6.8, 5.4 Hz, 3H); $^{13}$C NMR (101 MHz, $C_6D_6$) δ 144.1 (d, J=14.4 Hz), 142.5 (dd, J=16.7, 3.2 Hz), 138.2 (d, J=4.9 Hz), 137.5 (d, J=7.4 Hz), 137.1 (d, J=18.1 Hz), 135.2 (d, J=23.4 Hz), 134.3 (dd, J=21.5, 1.7 Hz), 133.4 (d, J=20.0 Hz), 132.8 (d, J=16.9 Hz), 132.1 (d, J=7.6 Hz), 131.9-131.7 (m), 131.5 (d, J=4.7 Hz), 131.2 (d, J=4.9 Hz), 130.2, 129.8 (d, J=15.6 Hz), 125.1 (d, J=24.1 Hz), 122.4 (d, J=24.2 Hz), 121.2 (dp, J=121, 3.6 Hz), 100.5 (d, J=20.8 Hz), 100.2 (d, J=20.9 Hz), 71.4 (dd, J=9.0, 3.6 Hz), 70.6 (d, J=4.3 Hz), 70.3 (d, J=4.5 Hz), 69.8, 30.5 (dd, J=19.8, 9.5 Hz), 21.3 (d, J=10.7 Hz), 15.9 (d, J=1.1 Hz); $^{19}$F NMR (282 MHz, $C_6D_6$) δ −62.66 (d, J=1.6 Hz); $^3$P NMR (121 MHz, $C_6D_6$) δ 11.62 (d, J=38.2 Hz), −22.86 (d, J=38.4 Hz).

REFERENCES

1. D. J. Newman, G. M. Cragg, *J. Nat. Prod.* 79, 629-661 (2016).
2. J. D. Scott, R. M. Williams, *Chem. Rev.* 102, 1669-1730 (2002).
3. M. Chrzanowska, M. D. Rozwadowska, *Chem. Rev.* 104, 3341-3370 (2004).
4. M. Chrzanowska, A. Grajewska, M. D. Rozwadowska, *Chem. Rev.* 116, 12369-12465 (2016).
5. C. Cuevas, A. Francesch, *Nat. Prod. Rep.* 26, 322-337 (2009).
6. C. Cuevas, et al., *Org. Lett.* 2, 2545-2548 (2000).
7. E. J. Corey, D. Y Gin, R. S. Kania, *J. Am. Chem. Soc.* 118, 9202-9203 (1996).
8. A. G. Myers, D. W. Kung, *J. Am. Chem. Soc.* 121, 10828-10829 (1999).
9. C. M. Rath, et al., *ACS Chem. Biol.* 6, 1244-1256 (2011).
10. L.-Q. Song, Y.-Y. Zhang, J.-Y. Pu, M.-C. Tang, C. Peng, G.-L. Tang, *Angew. Chem., Int. Ed.* 56, DOI: 10.1002/anie.201704726
11. E. J. Martinez, T. Owa, S. L. Schreiber, E. J. Corey, *Proc. Natl. Acad. Sci. USA* 96, 3496-3501 (1999).
12. A. G. Myers, A. T. Plowright, *J. Am. Chem. Soc.* 123, 5114-5115 (2001).
13. A. G. Myers, B. A. Lanman, *J. Am. Chem. Soc.* 124, 12969-12971 (2002).
14. E. M. Ocio, et al., *Blood* 113, 3781-3791 (2009).
15. A. Fontana, P. Cavaliere, S. Wahidulla, C. G. Naik, G. Cimino, *Tetrahedron* 56, 7305-7308 (2000).
16. J. W. Lane, Y. Chen, R. M. Williams, *J. Am. Chem. Soc.* 127, 12684-12690 (2005).
17. Y.-C. Wu, J. Zhu, *Org. Lett.* 11, 5558-5561 (2009).
18. W. Liu, X. Liao, W. Dong, Z. Yan, N. Wang, Z. Liu, *Tetrahedron* 68, 2759-2764 (2012).
19. R. Chen, H. Liu, X. Chen, *J. Nat. Prod.* 76, 1789-1795 (2013).
20. N. Saito, C. Tanaka, Y.-i. Koizumi, K. Suwanborirux, S. Amnuoypol, S. Pummangura, A. Kubo, *Tetrahedron* 60, 3873-3881 (2004).
21. S. Xu et al., *Eur. J. Org. Chem.* 975-983 (2017).
22. J. W. Lown, A. V. Joshua, J. S. Lee, *Biochemistry* 21, 419-428 (1982).

23. J. J. Perez-Ruixo, et al., *Clin. Pharmacokinet.* 46, 867-884 (2007).
24. U.S. Food and Drug Administration, Center for Drug Evaluation and Research (2015). Retrieved from https://www.fda.gov/aboutfda/centersoffices/officeofmedicalproductsandtobacco/cder/Identification No. 207953 Orig 1s000, Pharmacology Reviews).
25. J. R. Spencer, et al., *Bioorg. Med. Chem. Lett.* 16, 4884-4888 (2006).
26. J. M. Reid, M. J. Kuffel, S. L. Ruben, J. J. Morales, K. L. Rinehart, D. P. Squillace, M. M. Ames, *Clin. Cancer. Res.* 8, 2952-2962 (2002).
27. H.-S. Yeom, S. Kim, S. Shin, *Synlett* 924-928 (2008).
28. U. K. Tambar, B. M. Stoltz, *J. Am. Chem. Soc.* 127, 5340-5341 (2005).
29. K. M. Allan, B. D. Hong, B. M. Stoltz, *Org. Biomol. Chem.* 7, 4960-4964 (2009).
30. P. M. Tadross, C. D. Gilmore, P. Bugga, S. C. Virgil, B. M. Stoltz, *Org. Lett.* 12, 1224-1227 (2010).
31. L.-C. Campeau, D. J. Schipper, K. Fagnou, *J. Am. Chem. Soc.* 130, 3266-3267 (2008).
32. Y. Tan, F. Barrios-Landeros, J. F. Hartwig, *J. Am. Chem. Soc.* 134, 3683-3686 (2012).
33. V. Boekelheide, W. J. Linn, *J. Am. Chem. Soc.* 76, 1286-1291 (1954).
34. A. A. Tabolin, S. L. Ioffe, *Chem. Rev.* 114, 5426-5476 (2014).
35. C. Copéret, H. Adolfsson, T.-A. V. Khuong, A. K. Yudin, K. B. Sharpless, *J. Org. Chem.* 63, 1740-1741 (1998).
36. D.-S. Wang, Q.-A. Chen, S.-M. Lu, Y.-G. Zhou, *Chem. Rev.* 112, 2557-2590 (2012).
37. S.-M. Lu, Y.-Q. Wang, X.-W. Han, Y.-G. Zhou, *Angew. Chem., Int. Ed.* 45, 2260-2263 (2006).
38. L. Shi, Z.-S. Ye, L.-L. Cao, R.-N. Guo, Y. Hu, Y.-G. Zhou, *Angew. Chem., Int. Ed.* 51, 8286-8289 (2012).
39. Y. Kita, K. Yamaji, K. Higashida, K. Sathaiah, A. Iimuro, K. Mashima, *Angew. Chem., Int. Ed.* 52, 2046-2050 (2013).
40. J. Wen, R. Tan, S. Liu, Q. Zhao, X. Zhang, *Chem. Sci.* 7, 3047-3051 (2016).
41. R. Dorta, D. Broggini, R. Stoop, H. Riiegger, F. Spindler, A. Togni, *Chem. Eur. J.* 10, 267-278 (2004).
42. S,R$_p$-BTFM-Xyliphos (27) is produced and sold by Solvias AG and is licensed to Sigma-Aldrich Co., and Strem Chemicals under the name SL-J008-2. For a scalable synthesis of 27, see Supplementary Materials.
43. E. J. Martinez, E. J. Corey, *Org. Lett.* 2, 993-996 (2000).
i. A. B. Pangborn, M. A. Giardello, R. H. Grubbs, R. K. Rosen, F. J. Timmers, *Organometallics*, 15, 1518-1520 (1996).
ii. D. L. Comins, J. D. Brown, *J. Org. Chem.* 49, 1078-1083 (1984).
iii. M. Harmata, W. Yang, C. L. Barnes, *Tetrahedron Lett.* 50, 2326-2328 (2009).
iv. K. C. Nicolau, D. Rhoades, M. Lamani, M. R. Pattanayak, S. M. Kumar, *J. Am. Chem. Soc.* 138, 7532-7535 (2016).
v. P. M. Tadross, C. D. Gilmore, P. Bugga, S. C. Virgil, B. M. Stoltz, *Org. Lett.* 12, 1224-1227 (2010).
vi. F. Spindler, Patent Number EP 0646590 A1.
vii. M. Jin, M. Nakamura, *Chem. Lett.* 42, 1035-1037 (2013).
viii C. A. Busacca, J. C. Lorenz, N. Grinberg, N. Haddad, M. Hrapchak, B. Latli, H. Lee, P. Sabila, A. Saha, M. Sarvestani, S. Shen, R. Varsolona, X. Wei, C. H. Senanayake, *Org. Lett.* 7, 4277-4280 (2005).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:
1. A method for preparing a compound of Formula (I):

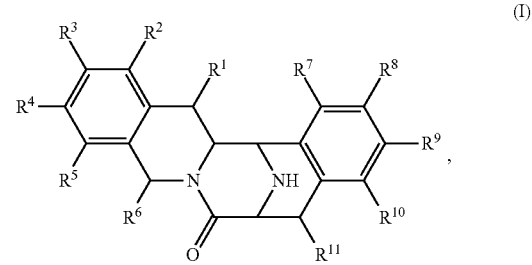

comprising contacting a compound of Formula (II):

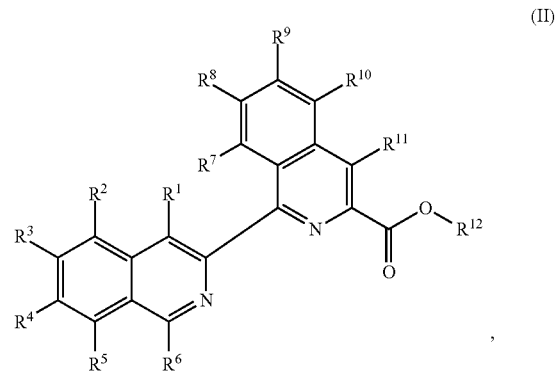

with a transition metal catalyst (preferably a chiral transition metal catalyst) under hydrogenation conditions, wherein, as valence and stability permit:
$R^1$ and $R^7$ are each independently hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, trialkylsilyloxy, or acylamino;
each instance of $R^2$, $R^3$, $R^4$, $R^5$, $R^8$, $R^9$, $R^{10}$, and $R^{11}$ is independently hydrogen, hydroxyl, halogen, nitro, alkyl, alkenyl, alkynyl, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, trialkylsilyloxy, acylamino, aryl, heteroaryl, carbocyclyl, heterocyclyl aralkyl, aralkyloxy, hetaralkyl, carbocyclylalkyl, or heterocyclylalkyl;

$R^6$ is hydrogen, hydroxyl, halogen, nitro, cyano, carboxyl, sulfate, alkyl, alkenyl, alkynyl, amino, alkoxy, alkylamino, alkylthio, ether, thioether, ester, amide, thioester, carbonate, carbamate, urea, sulfonate, sulfone, sulfoxide, sulfonamide, acyl, acyloxy, trialkylsilyloxy, or acylamino; or any two of $R^1$, $R^2$, $R^3$, $R^4$, $R^5$, and $R^6$, together with the carbon atoms to which they are attached, form an aryl, heteroaryl, carbocyclyl, or heterocyclyl; or any two of $R^7$, $R^8$, $R^9$, $R^{10}$, and $R^{11}$, together with the carbon atoms to which they are attached, form an aryl, heteroaryl, carbocyclyl, or heterocyclyl; and $R^{12}$ is H, alkyl or aralkyl.

2. The method of claim 1, wherein the compound of Formula (I) has the formula IA:

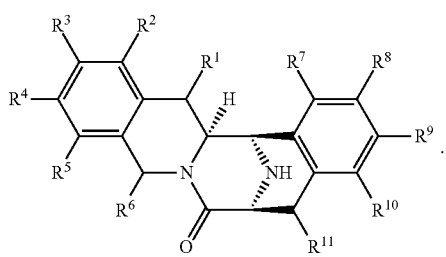

(IA)

3. The method of claim 1, wherein the compound of Formula (I) has the formula IB:

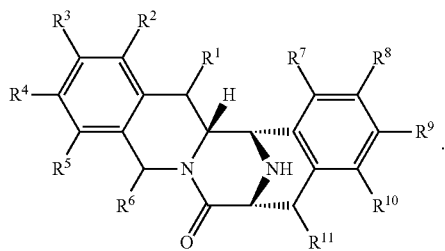

(IB)

4. The method of claim 1, wherein the transition metal catalyst comprises an iridium complex.

5. The method of claim 4, wherein the iridium catalyst is prepared by combining an iridium source and a chiral ligand.

6. The method of claim 5, wherein the iridium source is selected from (acetylacetonato)(1,5-cyclooctadiene)iridium (I), (acetylacetonato)(1,5-cyclooctadiene)iridium(I), (acetylacetonato)dicarbonyliridium(I), bis[1,2-bis(diphenylphosphino)ethane]carbonyl chloroiridium(I), bis(1,5-cyclooctadiene)diiridium(I) dichloride, bis(1,5-cyclooctadiene)iridium(I) tetrafluoroborate, bis (cyclooctadiene)iridium(I) tetrakis(3,5-bis(trifluoromethyl)phenyl)borate, chlorobis(cyclooctene)iridium(I)dimer, (1,5-cyclooctadiene)bis(methyldiphenylphosphine)iridium(I) hexafluorophosphate, (1,5-cyclooctadiene)(hexafluoroacetylacetonato)iridium(I), (1,5-cyclooctadiene)-η5-indenyl)iridium(I), (1,5-cyclooctadiene)(methoxy)iridium(I) dimer, (1,5-cyclooctadiene)(pyridine)(tricyclohexylphosphine)-iridium(I) hexafluorophosphate, (1,5-cyclooctadiene)(pyridine)(tricyclohexylphosphine)-iridium(I) hexafluorophosphate, and (1,5-cyclooctadiene)(pyridine)(tricyclohexylphosphine)iridium(I) tetrakis[3,5-bis(trifluoromethyl)phenyl]borate.

7. The method of claim 5, wherein the iridium source is bis(1,5-cyclooctadiene)diiridium(I) dichloride.

8. The method of claim 5, wherein the chiral ligand is a diphosphine ligand.

9. The method of claim 8, wherein the diphosphine ligand is selected from S—(CF$_3$)-t-BuPHOX, S,S-Et-FerroTANE, S,R$_p$-xyliphos, or S,R$_p$-BTFM-xyliphos, R—(CF$_3$)-t-BuPHOX, R,R-Et-FerroTANE, R,S$_p$-xyliphos, and R,S$_p$-BTFM-xyliphos.

10. The method of claim 5, wherein the chiral ligand is S,R$_p$-BTFM-xyliphos or R,S$_p$-BTFM-xyliphos.

11. The method of claim 1, wherein the transition metal catalyst is a chiral transition metal catalyst and is used in an amount from about 0.1 mol % to about 100 mol % relative to the compound of formula (II) or (VII).

12. The method of claim 1, wherein the transition metal catalyst is a chiral transition metal catalyst and is used in an amount from about 5 mol % to about 30 mol % relative to the compound of formula (II) or (VII).

13. The method of claim 1, wherein the iridium catalyst is used in an amount of about 20 mol % relative to the compound of formula (II) or (VII).

* * * * *